(12) United States Patent
Wasserstrom et al.

(10) Patent No.: US 9,458,503 B2
(45) Date of Patent: Oct. 4, 2016

(54) METHODS FOR DISTINGUISHING BETWEEN NATURAL AND ARTIFICIAL DNA SAMPLES

(75) Inventors: Adam Wasserstrom, Nes-Ziona (IL); Danny Frumkin, Rehovot (IL)

(73) Assignee: Nucleix, Herzelya (IL)

( * ) Notice: Subject to any disclaimer, the term of this patent is extended or adjusted under 35 U.S.C. 154(b) by 38 days.

(21) Appl. No.: 13/381,565

(22) PCT Filed: Jul. 1, 2010

(86) PCT No.: PCT/IB2010/001620
§ 371 (c)(1),
(2), (4) Date: Apr. 10, 2012

(87) PCT Pub. No.: WO2011/001274
PCT Pub. Date: Jan. 6, 2011

(65) Prior Publication Data
US 2012/0190023 A1    Jul. 26, 2012

Related U.S. Application Data

(60) Provisional application No. 61/222,753, filed on Jul. 2, 2009, provisional application No. 61/285,758, filed on Dec. 11, 2009.

(51) Int. Cl.
| | |
|---|---|
| *C12P 19/34* | (2006.01) |
| *C12Q 1/68* | (2006.01) |
| *C07H 21/02* | (2006.01) |
| *C07H 21/04* | (2006.01) |
| *C07H 21/00* | (2006.01) |

(52) U.S. Cl.
CPC ....... *C12Q 1/6876* (2013.01); *C12Q 2600/154* (2013.01)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

| | | |
|---|---|---|
| 6,764,822 B1 | 7/2004 | Butler et al. |
| 6,812,339 B1 | 11/2004 | Venter et al. |
| 2002/0152035 A1 | 10/2002 | Perlin |
| 2004/0181048 A1 | 9/2004 | Wang |
| 2005/0153316 A1* | 7/2005 | Jeddeloh et al. ............ 435/6 |
| 2007/0092883 A1 | 4/2007 | Schouten |
| 2007/0178506 A1 | 8/2007 | Martiensen et al. |
| 2007/0202526 A1 | 8/2007 | Nakami et al. |
| 2007/0207195 A1 | 9/2007 | Yarosh |
| 2007/0275402 A1 | 11/2007 | Lo |
| 2008/0286773 A1 | 11/2008 | Bender |

FOREIGN PATENT DOCUMENTS

| | | |
|---|---|---|
| EP | 1748080 A2 | 1/2007 |
| WO | WO 02/12328 A2 | 2/2002 |
| WO | 2005/040399 | 5/2005 |
| WO | 2007/018601 | 2/2007 |
| WO | WO 2008/104002 A2 | 8/2008 |
| WO | WO 2009/083989 A1 | 7/2009 |

OTHER PUBLICATIONS

Fantappié et al., Lack of DNA methylation in Schistosoma mansoni. Experimental Parasitology, 98, 162-166, 2001.*
International Search Report received in the related application No. PCT/IB2010/003397, dated Sep. 11, 2012.
Frumkin, et al., "DNA methylation-based forensic tissue identification", *Forensic Science International: Genetics*, 2010, vol. 5, No. 5, pp. 517-524.
Frumkin, et al., "Authentication of forensic DNA samples", *Forensic Science International: Genetics*, 4, 95-103, 2010.
International Search Report received in the corresponding PCT application PCT/IB2010/01620, dated Mar. 10, 2011.
Herman et al., "Methylation-specific PCT: A novel PCR assay for methylation status of CpG islands", *Proc. Natl. Acad. Sci.*, 1996, vol. 93, No. 18, pp. 9821-9826.
Martin-Magniette, et al., "Evaluation of the gene-specific dye bias in cDNA microarray experiments", Bioinformatics, 2005, vol. 21, No. 9, pp. 1995-2000.
Touchman, et al., Genebank accession No. G54325.1 CBS16 Human EGreen *Homo sapiens* STS genomic, sequence tagged site, Aug. 23, 1999 [online], internet: <URL: http://ncbi.nlm.nih.gov/nuccore/G54325.1>.
Yamagata et al., (2009) Aberrant DNA methylation status in human uterine leiomyoma. Mol Hum Reprod 15(4): 259-67.
Lowe et al., "A computer program for selection of oligonucleotide primers for polymerase chain reactions," Nucleic Acids Res, 18(7): 1757-1761 (1990).
Rubin et al., "Alu repeated DNAs are differentially methylated in primate germ cells," Nucleic Acids Res, 22(23): 5121-5127 (1994).
Zeschnigk et al., "IGF2/H19 hypomethylation in Silver-Russell syndrome and isolated hemihypoplasia," European Journal of Human Genetics, 16: 328-334 (2008).
Zhao et al., "Study on the application of parent-of-origin specific DNA methylation markers to forensic genetics," Forensic Sciences International, 154: 122-127 (2005).
U.S. Appl. No. 13/029,719, Final Office Action, Mar. 19, 2015.
Wittenberg et al., (2005) Validation of the high-throughput marker technology DArT using the model plant *Arabidopsis thaliana*. Mol Genet Genomics 274(1): 30-9.

* cited by examiner

*Primary Examiner* — Frank Lu
(74) *Attorney, Agent, or Firm* — Winston & Strawn LLP

(57) ABSTRACT

The present invention provides methods for distinguishing between natural and artificial DNA in samples containing nucleic acid molecules. In addition, the present invention provides methods for verifying that DNA profiles obtained from samples represent natural DNA. In various embodiments, the methods employ an array of nucleic acid based procedures for verifying that a DNA sample originates from a natural source. The invention further provides kits for verifying that a DNA sample originates from a natural source employing the methods and reagents described in the disclosure.

5 Claims, 15 Drawing Sheets

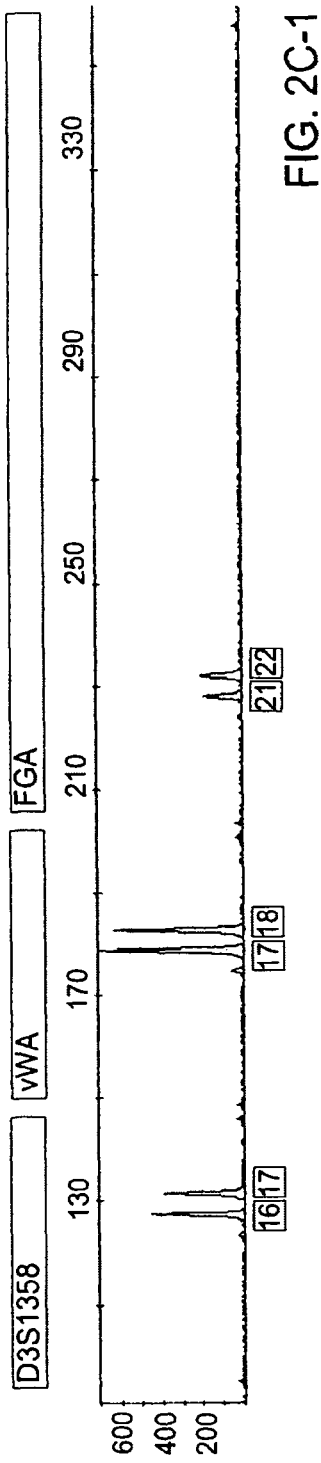
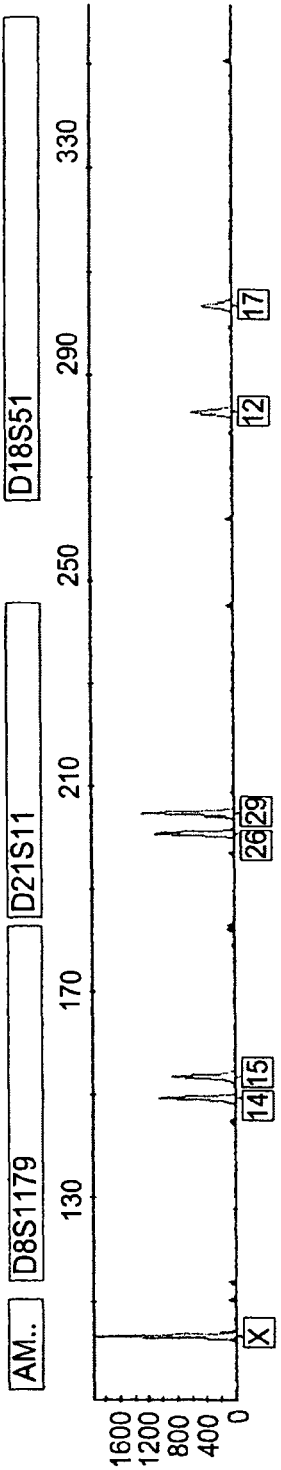
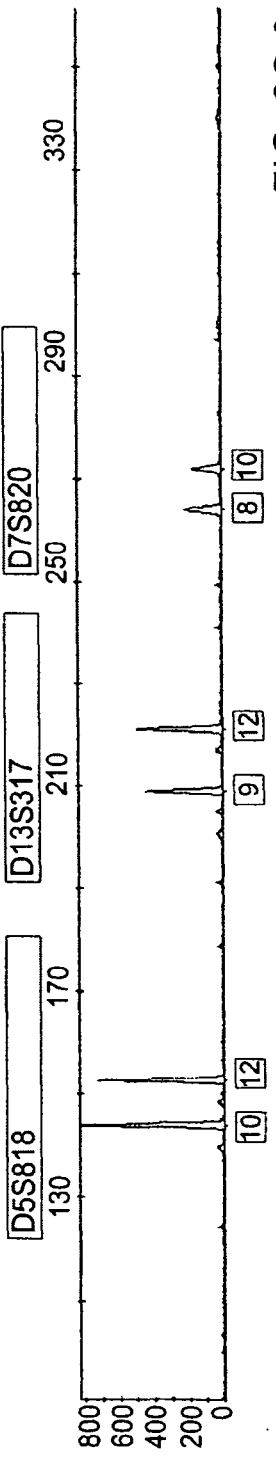
FIG. 2C-1
FIG. 2C-2
FIG. 2C-3

SEQUENCE LISTING

<160> NUMBER OF SEQ ID NOS: 66

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttcgttctaa actatgacaa gtgt                                              24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtcaggctg actatggagt t                                                 21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctcggtgcc aagcagctc                                                    19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggagctgatg caggctcttc c                                                 21

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggcgccat cttcggtaaa                                                    20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgttaacaaa gaccaagcag cgta                                               24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagaggttg aaaggttttg gtt                                                23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgagactcag ggcactgagc                                                    20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgtgacgat ggagacagga g                                                  21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccagagctg aatgcagtag g                                                  21
```

```
<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acacgggcaa gagtaagact cca                                            23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcgggtggg ggcaagggat c                                              21

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taagaataat cagtatgtga cttgg                                          25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atacatagga tggatggata gatg                                           24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttaaactcac aaattaaact ataacc                                         26

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagtgatttg tttgtaattg ttagtaa                                        27
```

```
<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgggaagggt tttagtatta aaag                                          24

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttcaacaaa atcaacattt tactac                                        26

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgaggtgat gaggaagggg t                                             21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
attctcaacc caaactcctt tca                                           23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21 cacccttttaa aaatttttcct taaa                                        24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
attgtgagaa gaggaagtta aaagt                                         25
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtgagggag gaagggatag                                                  20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttaatcccac ttccaatcca ct                                               22

<210> SEQ ID NO 25
<211> LENGTH: 501
<212> TYPE: DNA
<213> ORGANISM: Homo sapiens

<400> SEQUENCE: 25
cccagaaggc atgtgggctg gctcaataaa atattaagca gctctttcca acgatgtggc      60
tgatggtttg tgtggttgtt agagagccca ggagacaggc agaaaggaag gcatgtgacc     120
ggatcacaat catcagctct ctgctgtcct ctttgggaag ggttttagta ttaaaaggac     180
atttattctc attaatgcaa aattaaggag ttttaaaagc ttttacaacc tagactccct     240
ctgagaggtt agccttgaca ccctaatcgc cttctgctcc cgccactgct cggtgccaag     300
cagctcccac ggccccggcg ggtctgatga tagccggaca ggaggagga aggggaggag      360 gaagagcctg catcagctcc tacgattgcc cagccccatc ctgggagtga ttaaacggtg     420
catcaccaaa tgccagtccc actgacaggc aggtcaccgt gcacttcagg gcactctaaa     480
ttgccgactc tccatgtaga g                                              501

<210> SEQ ID NO 26
<211> LENGTH: 600
<212> TYPE: DNA
<213> ORGANISM: Homo sapiens

<400> SEQUENCE: 26
aattgcaagt ccattagaga cctgggcttc tgacctgata ctgccaccta ctatctctat      60
ttccttgagc tagttctgta accttttcaa ttctcagtgt tctcctcttc aaaatgggga     120
tcatagtctc tgactcataa ataggaagat aaataaattc atccaaggaa aaagcatgg      180 tacccagcaa ataggaagca cttcattaag tgtttgctat tattattact ttttttttt      240 ttttttttgag atagagtctc tctctgttgc ccaggttgga gtgcaattgt gcaatcttgc    300
ctcactgcac cctccacctc ccggtttcaa gtgattctcc tgcttcagcc tcccaaatag    360
ctgggatcac aggcacgcac caccgtgccc agctagctaa ttttttgtatt tttagtagag    420 acatggtttt gccatgttgg tcaggccggt ctcaaactcc tgacctcagg tgatccaaag    480
tggatcctca gcctcccaaa gtgctggaat tacagccgtg agccaccgca cccagcctgt    540
tattactatt actatcatta ttgctcctcc tcctcctata ctacagcaag agcgcttgaa    600

<210> SEQ ID NO 27
<211> LENGTH: 360
<212> TYPE: DNA
<213> ORGANISM: Homo sapiens

<400> SEQUENCE: 27

| | | | | | | |
|---|---|---|---|---|---|---|
| ctcttccttc | actctctccc | ttcctctctc | tttctattct | cctcccctcc | tccctgtaaa | 60 |
| agctaccacc | tcatcctggg | caccctggtt | atatcaactt | cagctatgag | gtaattttc | 120 |
| tctttactaa | ttttgaccat | tgtttgcgtt | aacaatgccc | tgggctctgt | aaagaatagt | 180 |
| gtgttgattc | tttatcccag | atgtttctca | gtggtcctg | attttacagt | tcctaccacc | 240 |
| agcttcccag | tttaagctct | gatggttggc | ctcaagcctg | tgtcgtccca | gcagcctccc | 300 |
| gcctggccac | tctgactcag | tctgtcctcc | taaatatggc | cgtaagctta | cccatcatga | 360 |

<210> SEQ ID NO 28
<211> LENGTH: 420
<212> TYPE: DNA
<213> ORGANISM: Homo sapiens

<400> SEQUENCE: 28

| | | | | | | |
|---|---|---|---|---|---|---|
| cttcctgagc | agtggttcat | gaatgaataa | acttacagcc | atatttagga | ggaaagagtc | 60 |
| aatccgaatg | gtcaggcagg | agggtgctgg | agcaacacag | gcttgaggcc | aaccatcaga | 120 |
| gcttaaactg | ggaagctgat | ggtaggaact | gtaaaattgg | gaccacttga | gaaaccactt | 180 |
| tatttgggat | gaagaatcca | cccactattc | tttacagagc | caggggact | gctaatgcaa | 240 |
| acagtgatca | aaattagtaa | agagaaaaat | tacctcatag | ctgaagttga | tataaccagg | 300 |
| gtgcccagga | tgaggtggta | gcttttatag | ggaggagggg | aggagaagag | aaagagagag | 360 |
| gaagggagag | tgtgaaggaa | gggaagagag | agtaagagat | taagtcaata | tgcaattgtt | 420 |

<210> SEQ ID NO 29
<211> LENGTH: 480
<212> TYPE: DNA
<213> ORGANISM: Homo sapiens

<400> SEQUENCE: 29

| | | | | | | |
|---|---|---|---|---|---|---|
| cagctgggat | gtggagtggt | gtgaggagtg | gccacagggg | agcagaggag | gtggcagaag | 60 |
| ccggaggtaa | aggtgtctta | aagtgagaaa | gaataactgc | atcttaacct | attgggaggt | 120 |
| cattgtaaag | aggagagtga | tggggtcaga | ttgtacagag | gaggcacttc | gtggtggtca | 180 |
| ggagcacaca | ctccagggca | gtgttccaac | ctgagtctgc | caaggactag | caggttgcta | 240 |
| accaccctgt | gtctcagttt | tcctacctgt | aaaatgaaga | tattaacagt | aactgccttc | 300 |
| atagatagaa | gatagataga | ttagatagat | agatagatag | atagatagat | agatagatag | 360 |
| atagatagat | aggaagtact | tagaacaggg | tctgacacag | gaaatgctgt | ccaagtgtgc | 420 |
| accaggagat | agtatctgag | aaggctcagt | ctggcaccat | gtgggttggg | tgggaacctg | 480 |

<210> SEQ ID NO 30
<211> LENGTH: 480
<212> TYPE: DNA
<213> ORGANISM: Homo sapiens

<400> SEQUENCE: 30

| | | | | | | |
|---|---|---|---|---|---|---|
| cgttcatttc | ttcctagcac | ttagaactgt | ttcttgttga | tacatttgct | ggcttcttcc | 60 |
| ctgtctcacc | ccttttccta | ccagaatgcc | agtcccagag | gcccttgtca | gtgttcatgc | 120 |
| ctacatccct | agtacctagc | atggtacctg | caggtggccc | ataatcatga | gttattcagt | 180 |

| | |
|---|---|
| aagttaaagg attgcaggag ggaaggaagg acggaaggaa ggaaggaagg aaggaaggaa | 240 |
| ggaaggaagg aaggaaggaa ggaaggcagg caggcaggca ggcaggcagg caaggccaag | 300 |
| ccatttctgt ttccaaatcc actggctccc tcccacagct ggattatggg ccagtaggaa | 360 |
| ttgccatttt cagggttttg ctgtcactgt agtcaggacc atgaagtctt taggcacctc | 420 |
| cactccacac accccctggt gagagctccc atctccctgt tctgaaacag ctccccaata | 480 |

<210> SEQ ID NO 31
<211> LENGTH: 480
<212> TYPE: DNA
<213> ORGANISM: Homo sapiens

<400> SEQUENCE: 31

| | |
|---|---|
| ttggaaggct gagatgggag gatcacttga ggccaggagt ttaagacaag gctggggaac | 60 |
| acagcgagac cccatctctt aaaaaaaaaa attagccgga catggtggct catgcctata | 120 |
| atcccaggta cttgggaggc tgaggcagga ggactgcttg agcccaggag tttgaggctg | 180 |
| tagtgagcta tgattccccc actgcagtcc aatctgggtg acagagcaag accctgtctc | 240 |
| atagatagat agatagatag atagatagat agatagatag atagatagat agatagacag | 300 |
| atagatacat gcaagcctct gttgatttca tgagtataag agatgccccc aaaggcacag | 360 |
| ggaatacaca ccacagaaaa atagatccct gggcagaagt gggcaagtga atatggccag | 420 |
| catgcccatt ctggagcagt gccctggcag ctgcagtcct cacctgggaa tagcttttcc | 480 |

<210> SEQ ID NO 32
<211> LENGTH: 1260
<212> TYPE: DNA
<213> ORGANISM: Homo sapiens

<400> SEQUENCE: 32

| | |
|---|---|
| acaatggcac aatctcagct cactgcagcc tccgcctcct gggttcaagt gattctcctg | 60 |
| cctcagcctc ccaagtagct gggattacag gcacacacca ccatgcccag ctaattttg | 120 |
| tatttttagt acagataggg tttcaccatg ttggtcaggc tggtctcaaa ctcctgacct | 180 |
| caggtgatcc acctgcctca gcttcccaaa gtgctgggat taccgcgtg agccaccgca | 240 |
| cctggccgtc aacacacaat taaatcttaa acacaaacct gcatattggc tgaccacgtg | 300 |
| cacctgcaaa acccttacct cccaccccca ggaagagggg gttctcgtcc ccacctctca | 360 |
| ttcccaccct tgaaattgcg aagaggatta taggtaacct gcaggcaccc tcgccagagc | 420 |
| gtctgtgctt ccagacactt ctccccattg ccggcaaccc ggctccactg ccgcgcccag | 480 |
| cctcctctgt tcactgctct ggcctcggcg cctggaaacc gcgtgtccat caaaacgtga | 540 |
| aggtgaacct cgtaagttta tgcaaactgg acaggaggga gagcagaggc agagatcacc | 600 |
| gtgtccactc gacgtcctga gcgaaaagcc acgtgtgccc acgtgacgat ggagacagga | 660 |
| ggaccagggc tctgcctgcc ccctttttctg agccctact gcattcagct ctggggcctg | 720 |
| ggccctcgac ggccaccacc tcctcacctg ggctcctgcg cagccaagcg cagtcccgca | 780 |
| cgctcatctt ccacgtcagc tcctgcagcg agagcttggc atgcttcccc agggagatga | 840 |
| acttcttggt gttcctgagg aagcggcgtt cgttgtgcct ggagcccag aggcctgggg | 900 |
| gcaccagccg gcgcaggcag gcccgcacga agccgtacac ctgccagggg ctgctgtgct | 960 |
| ggcggagcag ctgcaccagg cgacgggggt ctgtgtcctc ctcctcgggg gccgccacag | 1020 |
| agccctgggg cttctcccgg gcacagacac cggctgctgg ggtgaccgca gctcgcagcg | 1080 |
| ggcagtgcgt cttgaggagc accccgtagg ggcactgcgc gtggttccca agcagctcca | 1140 |

| | |
|---|---|
| gaaacagggg ccgcatttgc cagtagcgct ggggcaggcg ggcaacctg cggggagtcc | 1200 |
| ctggcatcca gggcctggaa cccagaaaga tggtctccac gagcctccga gcgccagtca | 1260 |

<210> SEQ ID NO 33
<211> LENGTH: 840
<212> TYPE: DNA
<213> ORGANISM: Homo sapiens

<400> SEQUENCE: 33

| | |
|---|---|
| agggaattt ctaactttga actacacaac acgcctttcc tctgaagtga agctggttaa | 60 |
| cttttcaccat attttcttgt ttctttacct ttaactttga gctattaggc atgggagagg | 120 |
| gagagggtct ggcttacccc ctcatttga aaatacatgg gagaaaataa tacatagcca | 180 |
| catttgtaat tttctaattc aaaggagtat ataattatgt aataatttta aaattaaata | 240 |
| ctgagacatg catatgcttt taaagcttct aattaaagtg gtgtcccaga taatctgtac | 300 |
| taataaaagt atattttaat agcaagtatg tgacaagggt gatttttcctc ttttggtatcc | 360 |
| ttatgtaata ttttgaagat agatagatag atagatagat agatagatag atagatagat | 420 |
| agaggtataa ataaggatac agataaagat acaaatgttg taaactgtgg ctatgattgg | 480 |
| aatcacttgg ctaaaaagca ctaaagcatt cctctgagag agacaattac ttttttgctt | 540 |
| aggaaactac ctcaacagcc tattagcatc tgaaatatga ggtccactat ccagatggga | 600 |
| gaggtttaga aaagaagac ttatattact ctgtataatg aaatgatgga gtatttggag | 660 |
| ttattcacca gtgctttgag aaaggaattg ggatcctgaa agaggaaact ggaagaagta | 720 |
| gctagaggga gagaacctca caatgtggca catagccagg ctacacagag ggacatgact | 780 |
| atacaggcgt tgtagataac atttccaata atgttgctat aatttaaaga tgtttcctac | 840 |

<210> SEQ ID NO 34
<211> LENGTH: 600
<212> TYPE: DNA
<213> ORGANISM: Homo sapiens

<400> SEQUENCE: 34

| | |
|---|---|
| aaaacaaaac aaaacaaaat actgaaacca gtgtgaacaa gagttacacg atggaaggca | 60 |
| tcagttttca caccagaagg aataaaaaca ggcaaaaata ccataagttg atcctcaaaa | 120 |
| tatgattgat tttaagcctt atgagataat tgtgaggtct taaaatctga ggtatcaaaa | 180 |
| actcagaggg aatatatat cttaagaatt ataacgattc cacatttatc ctcattgaca | 240 |
| gaattgcacc aaatattggt aattaaatgt ttactataga ctatttagtg agattaaaaa | 300 |
| aaactatcaa tctgtctatc tatctatcta tctatctatc tatctatcta tctatctatc | 360 |
| tatctatcgt tagttcgttc taaactatga caagtgttct atcatacct ttatatatat | 420 |
| taaccttaaa ataactccat agtcagcctg accaacatgg tgaaaccccg tctctaaaaa | 480 |
| aaatacaaaa attagctgga tgcagtagca catgcctgta gtcccagcta ctcaggaggc | 540 |
| tggggcagga gaaccacttg acccaagaag cggaggttgc agtgagccga gatcgcacca | 600 |

<210> SEQ ID NO 35
<211> LENGTH: 1320
<212> TYPE: DNA
<213> ORGANISM: Homo sapiens

<400> SEQUENCE: 35

| | |
|---|---|
| ccagatgtag gggagatagc agctggagag cataacagag gcactgacat gtgagcagct | 60 |
| aacgaggcct tttacaagac atctgtgacc acacggccaa gtagaagaaa gccgttaaaa | 120 |

| | |
|---|---|
| gcatcaaggt agttaggtaa agctgagtct gaagtaagta aaacattgtt acaggatcct | 180 |
| tgggggtgtcg cttttctggc cagaaacctc tgtagccagt ggcgcctttg cctgagtttt | 240 |
| gctcaggccc actgggctct ttctgcccac acggcctggc aacttatatg tattttgta | 300 |
| tttcatgtgt acattcgtat ctatctgtct atctatctat ctatctatct atctatctat | 360 |
| ctatctatct attccccaca gtgaaaataa tctacaggat aggtaaataa attaaggcat | 420 |
| attcacgcaa tgggatacga tacagtgatg aaaatgaact aattatagct acgtgaaact | 480 |
| atactcatga acacaatttg gtaaaagaaa ctggaaacaa gaatacatac ggttttgac | 540 |
| agctgtacta ttttacattc ccaacaacaa tgcacagggt ttcagtttct ccacatcctt | 600 |
| gtcaacattt gttattttct gggttttga taatagctgt gaaaggaaaa taaaaacttg | 660 |
| ggccgggcgc ggtggctcac gcctgtaatc ccagcacttt gggaggccaa ggcgggcaga | 720 |
| tctcaaggtc gggagattga gaccatcctg gctaacatgg tgaaaaccca tctctactaa | 780 |
| aaatacaaaa acaaaaaatt agccgggcgt ggtgacgggc gcggtggcgg gcgcatgtag | 840 |
| ttccggctac tcgggaggct gaggcaggaa aacagcatca acccgggagg cggcgcttgc | 900 |
| agtgagccaa gatcgcacca ctgcactcca gcctgggcga cagagcaaga cacggtctca | 960 |
| aaagaaaaaa agaaaaaaaa aacttggtac cccagttcct tctgccaaaa ggaaacaatt | 1020 |
| aagctgaaag ctgagtcatg caagaagttg ccttttcttt tgtccctaag cagagagcta | 1080 |
| ttaaaagtta tggcaaaaac cgcgattact tttgcaccaa ctaaataat agctgatgac | 1140 |
| ctaagacatc tctctgcact cactttctgt ctcggctgtg cttttcactc ttcctccttc | 1200 |
| ctccaaatgt taggaaaatg agtccaacaa gaaatacatc cataaagcaa aggcattctg | 1260 |
| gtgactcctg tacacatcat gactgtccac ccaaagcctg gcattgcctc taggaagtcc | 1320 |

```
<210> SEQ ID NO 36
<211> LENGTH: 540
<212> TYPE: DNA
<213> ORGANISM: Homo sapiens

<400> SEQUENCE: 36
```

| | |
|---|---|
| ttatttgggt aggaaaaaga gtggaggagt tttaactcac agataacagt ctgaaagtac | 60 |
| aagtggggaa atttgtacat tcattaatat acattatttt caaaacatat tcagagagct | 120 |
| tgaattgttg gtcaaatctc ctccttcaac ttgggttgag ccataggcag cccaaaaaga | 180 |
| cagacagaaa gatagataga tgattgattg atagatagat agatagatag atagatagat | 240 |
| agatagatag ataatgtatt tgtaaataca gataggcgtt agatgggtca gagtccagag | 300 |
| agtcacggat gcccactaaa gaaatgaact ctcctccaca tcccagactt ctgtgatacc | 360 |
| atgtccagca acccatccca atattcacat tggctgtagg cagaattacc atttgttcat | 420 |
| gtcaaaatat ttattgatca tgtgttatat gctagaaatg taactaagtg cttgcaatac | 480 |
| atcaataaat aatgcagtga acagaagagt cttactatgg cagctttcca atgagtcagc | 540 |

```
<210> SEQ ID NO 37
<211> LENGTH: 780
<212> TYPE: DNA
<213> ORGANISM: Homo sapiens

<400> SEQUENCE: 37
```

| | |
|---|---|
| ggggaactga gaggctactt tttgacccag gaccctaagc ctgtgtacgg agagagcatg | 60 |
| agctgggtga gctgcttgcc aaggagtggc atctgccctc atcagtggac acaaaaagcc | 120 |
| ccaggggtta agtggccatg gctgccctca tggctgcacc gggaggatga ctgtgttccc | 180 |

```
actctcagtc ctgccgaggt gcctgacagc cctgcaccca ggagctgggg ggtctaagag    240
cttgtaaaaa gtgtacaagt gccagatgct cgttgtgcac aaatctaaat gcagaaaagc    300
actgaaagaa gaatcccgaa accacagtt cccatttta tatgggagca aacaaaggca      360
gatcccaagc tcttcctctt ccctagatca atacagacag acagacaggt ggatagatag    420
atagatagat agatagatag atagatagat agatatcatt gaaagacaaa acagagatgg    480
atgatagata catgcttaca gatgcacaca caaacgctaa atggtataaa aatgaaatca    540
ctctgtaggc tgttttacca cctactttac taaattaatg agttattgag tataatttaa    600
ttttatatac taatttgaaa ctgtgtcatt aggttttta gtctatggca tcactttcgc     660
ttgtattttt ctattgattt cttttctttt cttttctttt tttgagacag agtctcactc    720
tcacccaggc tggagtaccg tggcacgatc ttggctcatt gcaaccacca cctcccgggt    780

<210> SEQ ID NO 38
<211> LENGTH: 660
<212> TYPE: DNA
<213> ORGANISM: Homo sapiens

<400> SEQUENCE: 38
ctactatgga ctaatattag tttggtcttg accagaagaa atccttgtgc gtatttatgt     60
tgaaagatga ataacttac tgaaattgtt aatgaagtat tggataagct actttaaaaa    120
taacaaaccc gactaccagc aacaacacaa ataaacaaac cgtcagccta aggtggacat    180
gttggcttct ctctgttctt aacatgttaa aattaaaatt aacttctctg gtgtgtggag    240
atgtcttaca ataacagttg ctactatttc ttttctttt ctcttcttt cctctctctt      300 tttctttctt tctttctttc tttctttct tctttctttc tttctttctt tctttctttc    360
tttctttctt tctgagacaa ggtctcaatt tgtcactcag agtgaagtgc agtggcatga    420
acatggctca ctgcagcctt aaccttctgg gctcaagaac tcctcctgcc tcagccctgc    480
aagtagctga gactacaggc acgtgccacc atgcccaact aattttttgta ttttttgta    540 gagacagggg tctcactgtg ttacccaggc tggtctcaaa ctcctgagct caattgatcc    600
acctgtctca gcctcccaaa gtgctgggat tacaggtgtg agccatcacg cttggcctat    660

<210> SEQ ID NO 39
<211> LENGTH: 1020
<212> TYPE: DNA
<213> ORGANISM: Homo sapiens

<400> SEQUENCE: 39
tttcttttaa ccttgtactg cagtttaaca catatgcaga aaagtgcaca aatccttagc     60
gaattttcac aaagtgagca atcctgtata tccagctctc aggtcaagaa acagaacatt    120
tctaaggctg ggtgaggtgg ctcatgcctg caatcccagc actttggaag actgatgcag    180
aaagatcact tgagggaagg agttcaagtc tagtctgggc aacatagtga gacctcttct    240
ctataaaaaa ttttttaaaa ttagccaggc atgttggcac attcctgtag tcctggctac    300
tcaggaggct ggggcaggaa gatcacttga gcccaggagg ttgaggctgc aaaaagctat    360
aattgtacca ctgcactcca gcctgggcaa cagaataaga ttctgttgaa ggaaagaagg    420
taggaaggaa ggaaggaagg aaggaaggaa ggaaggaagg aaggaaggaa ggagagagga    480
agaaagagag aagattttta ttcgggtaat gggtgcacca aatatcaga atcactgct     540 aaagaactta ttcatgtaac caacaccacc tgttccttaa aaacctattg aaataaaaac    600
agaaagaaag agagaaagag gaaggaagga aggaaggaaa gaaggaagat tgattcctag    660
```

```
aaccccagga gccctccaag gtccttttgt tcaccatcca ccatcccttc ctcccccag    720
tcctggtaac cactattcca acttccaatc ctttggacta gtgccatctg tttttaaact    780
tcataccaat ggactcatac ggtatgtgct ctggggtctg gtttctgtgt ccagtttcat    840
gttagttctt gtagcatttt aatcagagcc ggtcacataa tttgtagtgc ccagtgcaaa    900
atgaaagtgt ggaccatccc ctccaacccc accccaaca ccattcaaaa gttattaaga     960
atttcaagat ggcagctgca gagcctaagt cagtcacggg attcttctga gtgcacagcc   1020
```

<210> SEQ ID NO 40
<211> LENGTH: 960
<212> TYPE: DNA
<213> ORGANISM: Homo sapiens

<400> SEQUENCE: 40

```
tctgaatgtc aactcgactg gattaagaga tacctagata gtggtaatgc attctttctg     60
tgtgtatccg tgaattggtg ggctgagtgg agaatatctg ccttcaatgt gggcagatgc    120
cataccgttg gctgggctc agagagaaca aaaaggcaga ggaaaaacaa atttcccctc     180
tcacttctgg agatggaaca ttttcttct gcttttggac atcagaaatc caagttctct    240
ggcctttgga ctttgggact tgtgccagca ccctcctggg ttccctggcc tttggcctca    300
aactgaaggt tacactatca gcttccgttg ttctaagggc ttcagacttg acagccaca    360
ctgccagctt ccctgattct tcagcttgta gatggtctgt tatgggactt ttctcagtct    420
ccataaatat gtgagtcaat tccccaagtg aattgccttc tatctatcta tctatctgtc    480
tgtctgtctg tctgtctgtc tatctatcta tatctatcta tctatcatct atctatccat    540
atctatctat ctatctatct atctatctat ctatctatct atctatcgtc tatctatcca    600
gtctatctac ctcctattag tctgtctctg gagaacattg actaatacaa catctttaat    660
atatcacagt ttaatttcaa gttatatcat accacttcat acattatata aaaccttaca    720
gtgtttctcc cttctcagtg tttatggcta gtaattttt actgggtgcc agacactaat    780
ttttattttg ctaagtggtg aatatttttt atatccttaa aaatattttt gagtgttgat    840
ctgggtaaag ttaagttcaa tattggaaaa atattgattc ttttgaggat agttatcttc    900
taattagtct acctgttgcc ccataaatgg catgattttc cactctgtgt gagtcctcga    960
```

<210> SEQ ID NO 41
<211> LENGTH: 720
<212> TYPE: DNA
<213> ORGANISM: Homo sapiens

<400> SEQUENCE: 41

```
atctatagag ttaaaaagaa aagctcatca gtaagaaaat ccaatatgtt caagtccctt     60
gattaaggat gttataaaat aattgaaatg caatcaaacc aactatttta actccaaatt    120
acacctttaa aattccaaag aaagttcttc ttctatattt cttgggatt actaattgct     180
attaggacat cttaactggc attcatggaa ggctgcaggg cataacatta tccaaaagtc    240
aaatgcccca taggttttga actcacagat taaactgtaa ccaaaataaa attaggcata    300
tttacaagct agtttctttc tttctttttt ctctttcttt cttctttct ttctttcttt    360
ctttctttct ttctttcttt cttctctcctt ccttccttc ttcctttctt ttttgctggc    420
aattacagac aaatcactca gcagctactt caataaccat attttcgatt tcagaccgtg    480
ataataccta caaccgagtg tcagaggatc tgagaagcag aattgaagtc ctgaagcgca    540
aagtcataga aaaagtacag catatccagc ttctgcagaa aaatgttaga gctcagttgg    600
```

| | |
|---|---|
| ttgatatgaa acgactggag gtaagtatgt ggctgtggtc ccgagtgtcc ttgttttga | 660 |
| gtagagggaa aaggaaggcg atagttatgc actgagtgtc tactatatgc agagaaaagt | 720 |

<210> SEQ ID NO 42
<211> LENGTH: 900
<212> TYPE: DNA
<213> ORGANISM: Homo sapiens

<400> SEQUENCE: 42

| | |
|---|---|
| tcgcttgaac ccaggagggg gcgactgcag tgagccgaga tcgtgccact gcactccagc | 60 |
| ctgggtgaca gagcgagact ccatctcaaa aaaaaaaaaa aaaaaacaga atcataggcc | 120 |
| aggcacagtg gctaattgta ccttgggagg ctgagacggg aggatcgaga ccatcctggg | 180 |
| caccatagtg agaccccatc tctacaaaaa aaaaaaaaaa ttttttttaa atagccaggc | 240 |
| atggtgaggc tgaagtagga tcacttgagc ctggaaggtc gaagctgaag tgagccatga | 300 |
| tcacaccact acactccagc ctaggtgaca gagcaagaca ccatctcaag aaagaaaaaa | 360 |
| aagaagaaa agaaaagaaa agaaaagaaa agaaaagaaa agaaaagaaa agaaaagaaa | 420 |
| agaaaagaaa aaacgaaggg gaaaaaaaga gaatcataaa catatgta aatttctca | 480 |
| aaaaatcgt tatgaccata ggttaggcaa atatttctta gatatcacaa aatcatgacc | 540 |
| tattaaaaaa taataataaa gtaagtttca tcaaaactta aaagttctac tcttcaaaag | 600 |
| ataccttata agaaagtaa aaagacacgc cacaggctaa gagaaagtac ttctaatcac | 660 |
| atatctaaaa aaggacttgt gtccagatta aagaattctt acacatcaat aagacaaccc | 720 |
| aattaaaaat gggcaaaaga tttgaagaga tatttaacca agaaaacat ataaatgtgt | 780 |
| ccgggcgcga tggtaatccc agcactttga gaggccgagg caggcggatc acttgaggtc | 840 |
| aggagtttag gaccagtctg gccaacatgg tgaaaccctg tctctaataa aaatacaaaa | 900 |

<210> SEQ ID NO 43
<211> LENGTH: 780
<212> TYPE: DNA
<213> ORGANISM: Homo sapiens

<400> SEQUENCE: 43

| | |
|---|---|
| gttttaaaag ccgaatattt taggacaata tatggtaata atcaatcaat ggtttcagcc | 60 |
| ttagttttac tactggtcta ctttgggctt aaagttgacg tctcattgca ttgaaaatta | 120 |
| tttgataaga gaaataaaa tacattttac caacatgaaa gggtaccaat aacaagaaaa | 180 |
| ttgtggacag gtgcggtgat tcacgcctgc aatcctagca ctttgggagg ccgatgcagg | 240 |
| tgtattacct gagctcagga gatcaagacc agcctgggca acatggtgaa accccgtctc | 300 |
| tactaaaata caaaaaatta gctgggtgtg gtggtaggca cctgtaatcc cagctactct | 360 |
| ggaggctgaa acaggagaat cacttgaacc caggaggtgg agattgaagt gagccgagat | 420 |
| cacgccattg cactccagcc tgggcgactg agcaagactc agtctcaaag aaaagaaaag | 480 |
| aaagaaaag aaaattgtaa ggagttttct caattaataa cccaaataag agaattcttt | 540 |
| ccatgtatca atcatgatac taagcacttt acacacatgt atgttatgta atcattatat | 600 |
| catgcatgca aggtaatgag tattattttc ctcattttat aaaagaggaa actgatgttt | 660 |
| gaggctactt tgcttaagac cacagaacta gcaaggaaa agagaagtga atgtatccct | 720 |
| gatccccttt aacacttctt acacagcctc cccacaatgt ccagtattaa cttcataaat | 780 |

<210> SEQ ID NO 44
<211> LENGTH: 540
<212> TYPE: DNA
<213> ORGANISM: Homo sapiens

<400> SEQUENCE: 44

```
ctacagtgag ccgaggtcat gccattgcac tccaatctgg gcgacaagag tgaaactccg      60
tcaaaagaaa gaaagaaaga gacaaagaga gttagaaaga agaaagagag gagagagaga     120
aaggaaggaa ggaagaaaaa gaaagaaaaa gaaagaaaga gaaagaaaga agagaaaga     180
aagaaagaaa gaaagaaaga agaaagaaa gaaagaaaga aaagaaaga aagaaagaaa      240
gaaagaaaga agaaagaaa gaaagaaaga agaaagaaa ggaaggaaag aaagagcaag      300
ttactatagc ggtaggggag atgttgtaga aatatatata aacctcctta caccgcggag     360
accgcgtcag cccagcgagc acagaaccctt gtccttgccg ctgcgccttg cgtccgcacc    420
cgccgccagc tcaccatgga tgatgctatc accgcgctcg tcgtcgtcga caactgctcc     480
agcatgcgca aggctcccca ggccgtcttc ccctccattg tggggcaccc taggcaccag    540
```

<210> SEQ ID NO 45
<211> LENGTH: 780
<212> TYPE: DNA
<213> ORGANISM: Homo sapiens

<400> SEQUENCE: 45

```
aaatccatcc aaaaaatcca agatggccag aggtccccgg ctgctgcacc cagcccccac      60
cctactccca cctgcccctg cctccctctg ccccagctgc cctagtcagc accccaacca     120
gcctgcctgc ttggggaggc agccccaagg cccttccag gctctagcag cagctcatgg     180
tgggggggtcc tgggcaaata gggggcaaaa ttcaaagggt atctgggctc tggggtgatt   240
cccattggcc tgttcctccc ttatttccct cattcattca ttcattcatt cattcattca     300
ttcattcacc atggagtctg tgttcccttgt gacctgcact cggaagccct gtgtacaggg   360
gactgtgtgg gccaggctgg ataatcggga gcttttcagc ccacaggagg ggtcttcggt   420
gcctccttgg gcactcagaa ccttgggctc cctggcacat ttaaaatggg tttttattta   480
tggaccttga ttgaaatgtg gtgtgagttg tagcagtgtc atttccaggt accttctcag   540
ggacacaggg cgccctcccc cgtcctcccc cgccctcccc taccctcccc caccaggctc     600
cccatcaggc atcccctccc cagggcgccc cggggcccag cctcacaggc tctccgtggc   660
ctggaactgc agccccagct gcatcctaca ccccacccc aagggtaagt aagagggac    720
tctgggaggg gcttctgctg ctcccttca tgttccacaa ccctggaagc tcaggatgaa   780
```

<210> SEQ ID NO 46
<211> LENGTH: 540
<212> TYPE: DNA
<213> ORGANISM: Homo sapiens

<400> SEQUENCE: 46

```
caacccccac cttcctctgc ttcactttc accaactgaa atatggccaa aggcaaaaac      60
ccatgttccc actggcctgt gggtccccc atagatcgta agcccaggag gaagggctgt     120
gtttcagggc tgtgatcact agcacccaga accgtcgact ggcacagaac aggcacttag    180
ggaaccctca ctgaatgaat gaatgaatga atgaatgaat gaatgaatga atgaatgttt   240
gggcaaataa acgctgacaa ggacagaagg gcctagcggg aagggaacag gagtaagacc   300
agcgcacagc ccgacttgtg ttcagaagac ctgggattgg acctgaggag ttcaattttg     360
```

```
gatgaatctc ttaattaacc tgtgtggttc ccagttcctc ccctgagcgc ccaggacagt      420
agagtcaacc tcacgtttga gcgttgggga cgcaaacacg agagtgcttg gtgtgagcac      480
acaggaggag tcacgacaca gcagtgtaag agccgccacg agggtcccac acaggggag       540
```

<210> SEQ ID NO 47
<211> LENGTH: 660
<212> TYPE: DNA
<213> ORGANISM: Homo sapiens

<400> SEQUENCE: 47

```
aatcatataa tcggagaaac ttatttgtac tcgtgaaatt gatcagaaat aaatagaagt       60
cctgtagggg agggagatgt ggcttgagaa caattaatgt aaaggaggtc ttagaatgtt      120
agcagtagag agaactagag ggatcattta cttcaagccc ctcattttat agacattact      180
agtctcctac aatgtgccgg gcactttgcc cttattattt tgtgaactcc tcagactgat      240
cctataaggt agagttccca ccttccagaa gaagaaacag gtctagagga tccaagttga      300
cttggctgag atgtgaaagc cctagtggat gataagaata atcagtatgt gacttggatt      360
gatctatctg tctgtctgtc tgtctatcta tctatctatc tatctatcta tctatctatc      420
tatctatcta tctatccatc tatccatcca tcctatgtat ttatcatctg tcctatctct      480
atctaaccta tgtatctatt tatcatctat cctgtctcta tctatccttt gtatctatca      540
tctatcctat ctctatctaa gctatatatc tatttatcat ctatcctcta tcatctatct      600
atctatctat ctatctatct ctattgtatc tagttatcta tcctatatct atgtatgtat      660
```

<210> SEQ ID NO 48
<211> LENGTH: 601
<212> TYPE: DNA
<213> ORGANISM: Homo sapiens

<400> SEQUENCE: 48

```
gcagcgctag ccggcagtat ttccaaggcg caagttgcgg agtttctgtt tccttttttcc      60 tctggcgagc tttgcgttcc ctgtgcgccg gaagtgatcc cctgcgtggc tgggctgctc     120
gggttagatc gtcaggtgag ggaggaaggg atagccagcg cgaaggaagt gctggagtcg     180
tgtgttttgg ctgcgcgtga tcctgcgtgg gtcgggaggt gtttctgtgt aggtgtctgg     240
ccctttcatc agtcgtgcgg aggaccgcgt gatttccttc cagttctcct cggttttcag     300
gtggtggcgc catcttcggt aaagggtgtc cacctctccc tatggtgtgg ctggctagcc     360
cgggggtctc tacgctgctt ggtctttgtt aacggagatg aaggcagtaa ttttcagta      420 acaggtttca gatataagtc ccttggtgat gctaatattt atggaggcct tactatgcat     480
taagaacttt tttagaagtt tagaaaatgg cagtgaataa agcagataca aatctctgct     540
ctaagggagc ttgcatagta atgaaatttg agaagacagt ggattggaag tgggattaac     600
t                                                                      601
```

<210> SEQ ID NO 49
<211> LENGTH: 600
<212> TYPE: DNA
<213> ORGANISM: Homo sapiens

<400> SEQUENCE: 49

```
cggcccaagc ttgacctaca atttgcgcag gcgcagatcc taactttggc gtccctgtgg       60
gcggcctttg tgtgagacg cgtggtattc tgggaacgtc ggagacggaa gttacttcgt      120
ctttagctcc tggcgctgct ggcttctggg cggttttttgt cttttgattt caagagttag     180
```

```
gagctcgaga accgtttggc aatatgtacg acgcggatga gggtaggtga acgctcaaaa    240
cacacgccgt ggcggtccat ttaagcagga aagcgttggg aactgattgg attgaggatt    300
tggggccttc ccatgcgccg gctgcacagt ccccagcctt gttcccacac ttaccaggcc    360
gggaacgaaa ctggggtagg gagaggcgga gggtgcaggg aacatagtgt taatgttcca    420
ggttacgttc actgctgctc tctgcacttt ctcgttccgt tagatctgat cctcgttttcc   480 tgtggtgaag tagcgtgcag aatcgtaaga taaattacgt ttttgaatttg aagcaaaggg   540 caccctttaa aaattttcct taaagccaca gtcgacttaa cgaatagctc aattgttgag    600
```

<210> SEQ ID NO 50
<211> LENGTH: 1001
<212> TYPE: DNA
<213> ORGANISM: Homo sapiens

<400> SEQUENCE: 50

```
catctcctaa gtaaagaagg gaacccacac ttgttgaggg cctatatagg accatgaact     60
ggggacacaa actcaacctc acgatagcac tgatgaggca tgttctacta agctcatttt    120
acagtgagga aagagaggac cagccgggca cggtggttca cggctgtaat cccagcactt    180
tgggaggccg aggcgggcgg atcacaaggt caggatttgg agaccaacct ggccaagatg    240
gtgaaacccc atctctacta aaaatacaaa aattagccgg gtgtggtggc gcgcgcctgt    300
actcccagct acctgggagg ctgaggcaga agaatcgctt gaacccggga ggcggaggtt    360
gcagtgagcc gagatcacgc cactgcactc cagcctgggc gacagagtga gactccgtct    420
aaaaaaaaaa aagaaaaga atcatattc tcaacgttgg aatcggcctc ccagttgcaa     480
atcccaccac aatacaacag caattacaac tctcaactac aattatgttt gcatagagct    540
tcacggttta caaagcccag gttacgtttt gcaattatcc tgtttcacag attaagaagt    600
tgaactgagg ccgggcgcag tggctcacgt ctataatccc agcactttgg gaggcggggg    660
cgggaggatc acgaggtcag gagttcgaga ccagcctggc caacatggtg aaaccctgtc    720
tctactaaaa atacaaaaat tagccgggcg tggtggcgga cgcctgtaat cccagctact    780
caggaggctg aggcaggaga atcgcttgaa tccgggaggc ggaggttgca gtgaaccgag    840
actccagcct gggcaataag agtgaaactc cgtcttaaaa aaataaataa gttgaactga    900
aagcgtggcc taataagtgg caaggaggaa cacttccccc aaatttcttc ttcttagtgc    960
tttgccagat cagatctggg agatttcccc ctcccgccgg c                       1001
```

<210> SEQ ID NO 51
<211> LENGTH: 31
<212> TYPE: DNA
<213> ORGANISM: Homo sapiens

<400> SEQUENCE: 51

```
aatcgccttc tgctcccgcc actgctcggt g                                    31
```

<210> SEQ ID NO 52
<211> LENGTH: 25
<212> TYPE: DNA
<213> ORGANISM: Homo sapiens

<400> SEQUENCE: 52

```
gaccgaggcc ggagggtgag cgggg                                           25
```

```
<210> SEQ ID NO 53
<211> LENGTH: 23
<212> TYPE: DNA
<213> ORGANISM: Homo sapiens

<400> SEQUENCE: 53
ccccgatatt ctctgtcccg gaa                                            23

<210> SEQ ID NO 54
<211> LENGTH: 40
<212> TYPE: DNA
<213> ORGANISM: Homo sapiens

<400> SEQUENCE: 54
ctccgttaac aaagaccaag cagcgtagag accccngggc                          40

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aatcgccttc tgctcccgcc actgctcggt g                                   31

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gaccgaggcc ggagggtgag cgggg                                          25

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccccgatatt ctctgtcccg gaa                                            23

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctccgttaac aaagaccaag cagcgtagag accccngggc                          40

<210> SEQ ID NO 59
<211> LENGTH: 31
<212> TYPE: DNA
<213> ORGANISM: Homo sapiens
```

<400> SEQUENCE: 59
aatcgttttt tgttttcgtt attgttcggt g                                    31

<210> SEQ ID NO 60
<211> LENGTH: 26
<212> TYPE: DNA
<213> ORGANISM: Homo sapiens

<400> SEQUENCE: 60
aaaccgaaac cgaaaaataa acgaaa                                          26

<210> SEQ ID NO 61
<211> LENGTH: 23
<212> TYPE: DNA
<213> ORGANISM: Homo sapiens

<400> SEQUENCE: 61
ttttgatatt ttttgttttg gaa                                             23

<210> SEQ ID NO 62
<211> LENGTH: 40
<212> TYPE: DNA
<213> ORGANISM: Homo sapiens

<400> SEQUENCE: 62
ctccattaac aaaaaccaaa caacataaaa accccaaac                            40

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aattgttttt tgttttttgtt attgtttggt g                                   31

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aaaccaaaac caaaaaataa acaaaa                                          26

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ttttgatatt ttttgttttg gaa                                             23

<210> SEQ ID NO 66
<211> LENGTH: 40
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 66
ctccattaac aaaaaccaaa caacataaaa acccccaaac                              40
```

METHODS FOR DISTINGUISHING BETWEEN NATURAL AND ARTIFICIAL DNA SAMPLES

CROSS-REFERENCE TO RELATED PATENT APPLICATIONS

This application is the U.S. National Phase of PCT/IB2010/001620, filed Jul. 1, 2010, which claims priority to U.S. Provisional Application 61/222,753, filed Jul. 2, 2009, and U.S. Provisional Application 61/285,758, filed Dec. 11, 2009, all of which are incorporated herein by reference in entirety.

SEQUENCE LISTING

The instant application contains a Sequence Listing which has been submitted in ASCII format via EFS-Web and is hereby incorporated by reference in its entirety. Said ASCII copy, created on Nov. 17, 2010, is named 09528012.txt and is 34,597 bytes in size.

FIELD OF THE INVENTION

The present invention relates to methods for distinguishing between natural and artificial DNA samples. In particular, the invention relates to methods for determining whether DNA samples were generated in vitro or in vivo, and for verifying that a DNA profile represents natural DNA.

BACKGROUND

The following discussion of the background of the invention is merely provided to aid the reader in understanding the invention and is not admitted to describe or constitute prior art to the present invention.

DNA profiling uses a variety of techniques to distinguish between individuals of the same species using only samples of their DNA. Two humans will have the vast majority of their DNA sequence in common. DNA profiling exploits highly variable repeating sequences called short tandem repeats (STRs). Two unrelated humans will be unlikely to have the same numbers of tandem repeats at a given locus. In STR profiling, PCR is used to obtain enough DNA to amplify the number of repeats at several loci. It is possible to establish a match that is extremely unlikely to have arisen by coincidence, except in the case of identical twins, who will have identical genetic profiles.

DNA profiling is used in forensic science, to match suspects to samples of blood, hair, saliva, semen, etc. It has also led to several exonerations of formerly convicted suspects. It is also used in such applications as identifying human remains, paternity testing, matching organ donors, studying populations of wild animals, and establishing the province or composition of foods. It has also been used to generate hypotheses on the pattern of the human diaspora in prehistoric times.

Testing is subject to the legal code of the jurisdiction in which it is performed. Usually the testing is voluntary, but it can be made compulsory by such instruments as a search warrant or court order. Several jurisdictions have also begun to assemble databases containing DNA information of convicts. The United States maintains the largest DNA database in the world: The Combined DNA Index System (CODIS), with over 4.5 million records as of 2007. The United Kingdom, maintains the National DNA Database (NDNAD), which is of similar size. The size of this database, and its rate of growth, is giving concern to civil liberties groups in the UK, where police have wide-ranging powers to take samples and retain them even in the event of acquittal.

SUMMARY

The inventors developed methods for distinguishing between natural and artificial DNA. Furthermore, the inventors developed methods for verifying that DNA profiles obtained from samples represent natural DNA. In one embodiment, the methods accept as input a DNA sample, and output a decision whether the DNA is natural or artificial. In another embodiment, the methods accept as input both a DNA sample and data from profiling of the DNA sample, and output a decision whether the DNA profile represents natural or artificial DNA. In particular, the present inventive methods provide alternative ways to distinguish between natural and different types of artificial DNA, to distinguish between artificial DNA and failure of amplification, and in the presence or absence of a particular genomic locus; all of which methods provide, in combinatorial fashion, a profile of a DNA sample that permits a conclusion to be reached regarding whether the DNA had been synthesized artificially or whether the DNA is natural or whether a DNA profile represents natural DNA. The following embodiments exemplify various aspects of the present invention.

1. Methylated Loci

In one aspect, the invention provides a method for determining whether a DNA sample is natural or artificial, the method comprising:

(a) detecting one or more methylated or partially methylated CG loci in the sample;

(b) determining the methylation level of the CG loci detected in step (a);

wherein the presence of all CG loci with a methylation level of the analyzed CG loci comparable to a methylation reference level is indicative that the DNA is natural, otherwise the DNA is artificial.

2. Methylated and Control Loci

In one aspect, the invention provides a method for determining whether a DNA sample is natural or artificial, the method comprising:

(a) detecting one or more methylated or partially methylated CG loci in the sample;

(b) detecting one or more control loci;

(c) determining the methylation level of the CG loci detected in step (a);

wherein the presence of all loci with a methylation level of the analyzed CG loci comparable to a methylation reference level is indicative that the DNA is natural, otherwise the DNA is artificial.

3. Methylated and Unmethylated Loci

In one aspect, the invention provides a method for determining whether a DNA sample is natural or artificial, the method comprising:

(a) detecting one or more methylated or partially methylated CG loci in the sample;

(b) detecting one or more CG loci in the sample, wherein the CG loci are constitutively unmethylated in natural DNA;

(c) determining the methylation level of the CG loci detected in steps (a) and (b);

wherein the presence of all CG loci with methylation levels of the analyzed CG loci comparable to methylation reference levels is indicative that the DNA is natural, otherwise the DNA is artificial.

4. Methylated, Unmethylated, and Profile Linking as an Indicator of Success of Assay In one aspect, the invention provides a method for determining whether a profiled DNA sample is natural or artificial, the method comprising:
 (a) detecting one or more profile-linking loci in the sample;
 (b) detecting one or more methylated or partially methylated CG loci in the sample;
 (c) detecting one or more CG loci in the sample, wherein the CG loci are constitutively unmethylated in natural DNA;
 (d) determining the methylation level of the CG loci detected in steps (b) and (c);
 wherein absence of all loci is indicative of amplification failure; presence of all loci with methylation levels of the analyzed CG loci comparable to methylation reference levels is indicative that the DNA is natural; otherwise the DNA is artificial.

5. Methylated, Unmethylated, Profile Linking

In one aspect, the invention provides a method for determining whether a profiled DNA sample is natural or artificial, the method comprising:
 (a) detecting one or more profile-linking loci in the sample;
 (b) detecting one or more methylated or partially methylated CG loci in the sample;
 (c) detecting one or more CG loci in the sample, wherein the CG loci are constitutively unmethylated in natural DNA;
 (d) detecting one or more control loci in the sample;
 (e) determining the methylation level of the CG loci detected in steps (b) and (c);
 wherein absence of all loci is indicative of amplification failure; presence of all loci with methylation levels of the analyzed CG loci comparable to methylation reference levels is indicative that the DNA is natural; otherwise the DNA is artificial.

6. Methylated, Unmethylated, Profile Linking, and Representation Bias

In one aspect, the invention provides a method for determining whether a profiled DNA sample is natural or artificial, the method comprising:
 (a) detecting one or more profile-linking loci in the sample;
 (b) detecting one or more methylated or partially methylated CG loci in the sample;
 (c) detecting one or more CG loci in the sample, wherein the CG loci are constitutively unmethylated in natural DNA;
 (d) determining the methylation level of the CG loci detected in steps (b) and (c);
 (e) determining a representation bias level in the set of loci comprising of the profiling-linking loci, CG loci, and the loci used in the profiling of the DNA sample;
 wherein absence of all loci is indicative of amplification failure; presence of all loci with methylation levels of the analyzed CG loci comparable to methylation reference levels, and a representation bias level comparable to a representation bias reference level is indicative that the DNA is natural; otherwise the DNA is artificial.

7. Methylated, Unmethylated, Profile Linking, Control, and Representation Bias

In one aspect, the invention provides a method for determining whether a profiled DNA sample is natural or artificial, the method comprising:
 (a) detecting one or more profile-linking loci in the sample;
 (b) detecting one or more methylated or partially methylated CG loci in the sample;
 (c) detecting one or more CG loci in the sample, wherein the CG loci are constitutively unmethylated in natural DNA;
 (d) detecting one or more control loci in the sample;
 (e) determining the methylation level of the CG loci detected in steps (b) and (c);
 (f) determining a representation bias level in the set of loci comprising of the profiling-linking loci, CG loci, control loci, and the loci used in the profiling of the DNA sample;
 wherein absence of all loci is indicative of amplification failure; presence of all loci with methylation levels of the analyzed CG loci comparable to methylation reference levels, and a representation bias level comparable to a representation bias reference level is indicative that the DNA is natural; otherwise the DNA is artificial.

8. Bias-Prone Loci

In one aspect, the invention provides a method for determining whether a DNA sample is natural or artificial, the method comprising:
 (a) detecting two or more bias-prone loci in the sample;
 (b) determining a representation bias level in the set of bias-prone loci;
 wherein presence of all loci with a representation bias level comparable to a representation bias reference level is indicative that the DNA is natural; otherwise the DNA is artificial.

9. Bias-Prone and Profile-Linking Loci

In one aspect, the invention provides a method for determining whether a profiled DNA sample is natural or artificial, the method comprising:
 (a) detecting one or more profile-linking loci in the sample;
 (b) detecting two or more bias-prone loci in the sample;
 (c) determining a representation bias level in the set of loci detected in steps (a), (b), and the loci used in the profiling of the DNA sample;
 wherein absence of all loci is indicative of amplification failure; presence of all loci with a representation bias level comparable to a representation bias reference level is indicative that the DNA is natural; otherwise the DNA is artificial.

10. Bias-Prone, Profile-Linking, and Control Loci

In one aspect, the invention provides a method for determining whether a profiled DNA sample is natural or artificial, the method comprising:
 (a) detecting one or more profile-linking loci in the sample;
 (b) detecting two or more bias-prone loci in the sample;
 (c) detecting the one or more control loci in the sample;
 (d) determining a representation bias level in the set of loci detected in steps (a)-(c), and the loci used in the profiling of the DNA sample;
 wherein absence of all loci is indicative of amplification failure; presence of all loci with a representation bias level comparable to a representation bias reference level is indicative that the DNA is natural; otherwise the DNA is artificial.

11. Bias Prone and PCR Stutter

In one aspect, the invention provides a method for determining whether a DNA sample is natural or artificial, the method comprising:
 (a) detecting two or more bias-prone loci in the sample;
 (b) detecting one or more slippage loci in the sample;
 (c) determining a representation bias level in the set of loci detected in steps (a)-(b)
 (d) calculating a stutter level for the slippage loci detected in step (c)
 wherein presence of all loci with a representation bias level comparable to a representation bias reference level, and a stutter level comparable to a stutter reference level is indicative that the DNA is natural; otherwise the DNA is artificial.

12. Bias Prone, Profile-Linking and PCR Stutter

In one aspect, the invention provides a method for determining whether a profiled DNA sample is natural or artificial, the method comprising:

(a) detecting one or more profile-linking loci in the sample;

(b) detecting two or more bias-prone loci in the sample;

(c) detecting one or more slippage loci in the sample;

(d) determining a representation bias level in the set of loci detected in steps (a)-(c), and the loci used in the profiling of the DNA sample;

(e) calculating a stutter level for the slippage loci detected in step (c);

wherein absence of all loci is indicative of amplification failure; presence of all loci with a representation bias level comparable to a representation bias reference level, and a stutter level comparable to a stutter reference level is indicative that the DNA is natural; otherwise the DNA is artificial.

13. Bias Prone, Profile-Linking, Control, and PCR Stutter

In one aspect, the invention provides a method for determining whether a profiled DNA sample is natural or artificial, the method comprising:

(a) detecting one or more profile-linking loci in the sample;

(b) detecting two or more bias-prone loci in the sample;

(c) detecting one or more slippage loci in the sample;

(d) detecting one or more control loci in the sample;

(e) determining a representation bias level in the set of loci detected in steps (a)-(d), and the loci used in the profiling of the DNA sample;

(f) calculating a stutter level for the slippage loci detected in step (c);

wherein absence of all loci is indicative of amplification failure; presence of all loci with a representation bias level comparable to a representation bias reference level, and a stutter level comparable to a stutter reference level is indicative that the DNA is natural; otherwise the DNA is artificial.

14. Mixture Profiles

In one aspect, the invention provides a method for determining, in a mixture containing alleles of more than one individual, whether the alleles of a specific individual correspond to natural DNA, comprising:

(a) detecting one or more methylated or partially methylated alleles of CG loci corresponding to the specific individual;

(b) detecting one or more alleles corresponding to the specivic individual, wherein the alleles are of CG loci that are constitutively unmethylated in natural DNA;

(c) determining the methylation level of the alleles detected in steps (a) and (b);

wherein the presence of all alleles with methylation levels of the analyzed CG loci comparable to methylation reference levels is indicative that the DNA is natural, otherwise the DNA is artificial.

15. Mixture Profiles with Control Loci

In one aspect, the invention provides a method for determining, in a mixture containing alleles of more than one individual, whether the alleles of a specific individual correspond to natural DNA, comprising:

(a) detecting one or more control alleles corresponding to the specific individual in the sample;

(b) detecting one or more methylated or partially methylated alleles of CG loci corresponding to the specific individual;

(c) detecting one or more alleles corresponding to the specific individual, wherein the alleles are of CG loci that are constitutively unmethylated in natural DNA;

(d) determining the methylation level of the alleles detected in steps (b) and (c);

(e) determining a representation bias level in the set of alleles detected in steps (a)-(c), and in the alleles of the specific individual contained in the profile;

wherein the absence of all loci is indicative of amplification failure; presence of all alleles with methylation levels of the analyzed CG loci comparable to methylation reference levels, and with a representation bias level comparable to a representation bias reference level, is indicative that the DNA is natural; otherwise the DNA is artificial.

16. Presence of Long Fragments

In one aspect, the invention provides a method for determining whether a DNA sample is natural or artificial, the method comprising:

(a) detecting the presence or absence of nucleic acid fragments larger than 10 kilobases in the sample;

wherein presence is indicative that the DNA is natural; otherwise the DNA is artificial.

17. Distribution of Fragment Lengths

In one aspect, the invention provides a method for determining whether a DNA sample is natural or artificial, the method comprising:

(a) determining the distribution of nucleic acid fragment lengths in the sample;

(b) determining whether the distribution determined in step (a) is comparable to a reference distribution of nucleic acid fragment lengths;

wherein comparable distributions of nucleic acid fragment lengths of the sample and reference are indicative that the DNA is natural; otherwise the DNA is artificial.

18. Presence of RNA

In one aspect, the invention provides a method for determining whether a DNA sample is natural or artificial, the method comprising:

(a) detecting the presence of RNA in the sample;

wherein presence is indicative that the DNA is natural and absence is indicative that the DNA is artificial.

Loci used in the methods, other than the control loci, can belong to two or more categories. For example, a profile-linking locus can also be a methylated CG locus, and in this case the locus is analyzed twice—once as a profile-linking locus and once as a methylated CG locus. In another example, a locus used for profiling of the DNA sample can also be a bias-prone locus.

In one embodiment, the detection of loci is carried out using amplification of the loci and detection of amplification products. In one embodiment amplification is performed by PCR or real time-PCR. In one embodiment, detection of amplification products is performed by subjecting such products to electrophoresis and detection of electrophoresis products. In another embodiment, amplification and detection are performed in real time-PCR. In one embodiment, detection is performed by detecting preferential hybridization of sequences complementary to the amplified loci (e.g. by a DNA microarray). In one embodiment, one or more detected loci are loci used for profiling of human DNA. In one embodiment, one or more detected loci are CODIS loci. In one embodiment, amplification of loci is performed using primers that were used for profiling of the DNA sample. In one embodiment, amplification of loci is performed using primers that are for profiling CODIS loci. In one embodiment, one or more loci are amplified in a single amplicon with a single pair of primers. For example, a methylated or partially methylated CG locus and a constitutively unmethylated locus are amplified in the same amplicon with a single pair of primers.

In one embodiment, detecting the intensity of a locus is performed by detecting signals whose intensities are correlated to the quantity of products resulting from amplification of that locus. In one embodiment, such signals are relative fluorescence units (rfu) of capillary electrophoresis. In one embodiment, such signals are cycle threshold ($C_T$) of real-time PCR.

In one embodiment, the methylation level is determined for each CG locus separately. In one embodiment, a single methylation level is determined for all methylated or partially methylated CG loci as a group, and another single methylation level is determined for all constitutively unmethylated CG loci as a group. In one embodiment, a single methylation level is determined for all CG loci, including methylated or partially methylated, and constitutively unmethylated, together as a single group. In one embodiment, the methylation level is a number representing the intensity of signal obtained from the methylated variants. In one embodiment, the methylation level is a number between 0 and 1, representing the fraction of methylated variants, wherein 0 represents completely unmethylated and 1 represents completely methylated. In one embodiment, the methylation level is a number equal to or greater than 0, representing the ratio of signal corresponding to methylated or constitutively unmethylated CG loci to the signal corresponding to constitutively unmethylated CG loci. In one embodiment, the methylation level is defined as the ratio of intensity of signal of a CG locus or loci to the intensity of signal of a control locus or loci.

In one embodiment, determining the methylation level of a CG locus is performed by: (1) subjecting the DNA sample to sodium bisulfite treatment; (2) amplifying a genomic region that contains the CG locus from the bisulfite-treated DNA; (3) sequencing the amplified product from step 2, and analyzing the signal at the position of the original cytosine in the CG dinucleotide; and (4) determining the methylation level according to the signal analyzed in step 3, wherein the percentage of a 'C' signal corresponds to the fraction of methylated variants, whereas the percentage of a 'T' signal corresponds to the fraction of unmethylated variants (it should be understood in the context of the present invention that when sequencing from the complementary strand, the unmethylated CGs in the original sequence will appear as CA).

In one embodiment, determining the methylation level of a CG locus is performed by: (1) subjecting the DNA sample to sodium bisulfite treatment; (2) amplifying by PCR a genomic region that contains the CG locus from the bisulfite-treated DNA with two sets of primers, wherein one pair is designed to preferentially amplify the methylated version of the bisulfite-treated DNA, and the other pair is designed to preferentially amplify the unmethylated version of the same bisulfite-treated DNA; (3) detecting amplification products from step 2; (4) determining the methylation level according to the intensity of the signal analyzed in step 3, wherein the percentage of the signal corresponding to the methylation-specific primer pair corresponds to the fraction of methylated variants.

In one embodiment, determining the methylation level is performed by: (1) subjecting the DNA sample to digestion with a methylation-sensitive endonuclease (e.g. HpaII, HhaI, AciI, BstUI, HpyCH4); (2) amplifying the CG loci; (3) detecting amplification products from step 2; (4) determining the methylation level according to the intensity of the signal analyzed in step 3, wherein the methylation level is the ratio of signal corresponding to methylated or partially methylated CG loci to the signal corresponding to constitutively unmethylated CG loci.

In one embodiment, a methylation reference level is the corresponding methylation level obtained from natural DNA. The present inventive methods are not limited to checking for methylation levels from natural DNA every time a sample is to be analyzed and profiled. For example a reference level can be obtained at any point in time by subjecting several natural DNA samples to the methylation assay and then using the average score as the reference level for natural DNA.

In one embodiment, a representation bias level is calculated according to the following formula: 1/(((mean intensity of control loci multiplied by the mean intensity of CG loci) divided by mean intensity of the profile linking loci as measured in the verification reaction) divided by (mean intensity of the loci used in profiling of the sample divided by the mean intensity of the profile linking loci as measured in the profiling reaction)). In one embodiment, a representation bias reference level is the corresponding representation bias level obtained from natural DNA. In one embodiment, a stutter reference level is the corresponding stutter level obtained from natural DNA.

In one embodiment, methylation levels are considered to be comparable if the difference between their Euclidean distance and the average Euclidean distance of methylation levels of normal DNA samples is less than two standard deviations of the distribution of Euclidean distances of methylation levels of normal DNA samples.

In one embodiment, representation bias levels are considered comparable if the difference between their Euclidean distance and the average Euclidean distance of representation bias levels of normal DNA samples is less than two standard deviations of the distribution of Euclidean distances of representation bias levels of normal DNA samples.

In one embodiment, stutter levels are considered comparable if the difference between their Euclidean distance and the average Euclidean distance of stutter levels of normal DNA samples is less than two standard deviations of the distribution of Euclidean distances of stutter levels of normal DNA samples.

In one embodiment, the representation bias level is the ratio of the maximal to the minimal intensities of loci. In one embodiment, the representation bias level is the ratio of the standard deviation to the mean of all intensities of loci.

In one embodiment, the representation bias level is the mean deviation of peak heights of the capillary electrophoresis histogram obtained from analysis of the DNA sample, based on a linear regression of the analyzed peaks. The linear regression may be calculated for example using the Least Squares method ("Linear Regression (Lecture Notes in Statistics)" (Vol 175) section 2.2, pages 36-47 by Jürgen Groβ, Springer, 1st ed. (2003)). Calculating the linear regression allows for correction of the "ski-slope" effect which is seen in some capillary electrophoresis histograms as a result of sample overload, DNA degradation and other factors, and which causes the smaller amplicons to be amplified preferentially over larger amplicons. Since different fluorescent dyes have different intensities, the linear regression may be calculated separately for each dye. The calculation may be performed as follows:

1. For each fluorescent dye color (e.g. NED) of the capillary electrophoresis histogram
    i. Separate superimposed alleles at homozygous loci: for each homozygous locus, convert the single genotyped peak that corresponds to both alleles into two identical peaks with the same size as the original peak, and with a height equal to half the height of the original peak.

ii. Calculate a linear regression of all peaks corresponding to alleles.

iii. For each peak corresponding to an allele, calculate the normalized degree of deviation of the peak from the linear regression. This may be performed, for example, by the following non-limiting option.

i. Obtain the y-value of the linear regression at x, where x is the size of the peak.

ii. Calculate the normalized deviation of the peak height from the linear regression, equal to |peak height−value from c1|/(value from c1).

iii. Alternatively, calculate |peak height−value from c1|$^2$/(value from c1).

The representation bias level is defined as equal to the mean of the normalized deviation of the peak height.

1. In one embodiment, the stutter levels for a set of slippage loci is calculated from data obtained from a capillary electrophoresis run of amplification products by the following algorithm: From the raw data, find all local maxima and term them "peaks". A local maximum is a point $(X\ Y)_i$ in which the Y value is greater than the Y value of both the previous (i−1) data pair and the next (i+1) data pair (optionally use a smoothing method in order to reduce the number of maxima). Define the peak height as the Y value of the peak. Define the peak size as the X value of the peak.

2. Term all peaks that have Y values greater than a predetermined threshold "Putative alleles" (e.g. a threshold of 50 relative fluorescence units).

3. For each putative allele, obtain the "Maximum expected stutter value". The maximum expected stutter value represents the highest fraction of a stutter band that can be expected in in vivo generated DNA. The maximum expected stutter value is determined empirically based on multiple capillary electrophoresis runs of different samples and is different for each locus. (For example, for the D3S1358 locus, the maximum allowed stutter value in the GeneMapper software is 0.11).

4. Determine which putative alleles are true alleles. Examine all putative alleles, starting from the smallest size. For each examined putative allele, determine whether a putative allele exists at a predefined interval that is approximately one repeat unit larger than the putative allele that is examined (e.g. at [+3.25 bases, +4.75 bases]). If no putative allele is found at the designated region, term the examined putative allele "Allele". Otherwise: term the putative allele that is found in the designated region "The associated putative allele of the examined putative allele". Calculate the ratio of the height of the examined putative allele to the height of the associated putative allele of the examined putative allele. If this ratio is greater than the maximum expected stutter value of the examined putative allele, term the examined putative allele "Allele".

5. Determine stutter peaks. For each allele, inspect a predefined interval that is approximately one repeat unit smaller than the examined allele (e.g. [−4.75 bases, −3.25 bases]). Identify the highest peak in the interval. If the highest peak in the interval is not termed as "Allele", term the the peak "−1 stutter associated with the examined allele".

6. Calculating stutter levels. Calculate the size of the −1 stutter fraction, defined as the height of the −1 stutter peak divided by the height of its associated allele peak. Alternatively, the stutter level is defined as the area of the −1 stutter peak divided by the area of its associated allele peak.

In one embodiment, determining the presence of the non-genomic sequences is by cloning of the nucleic acids from the test sample, and sequencing the cloned molecules.

In one embodiment, determining whether distributions of nucleic acid fragment lengths are comparable comprises: (i) determining the probability that both distributions represent random samplings from the same source;

wherein, a probability less than about 0.05 indicates that the nucleic acids from the sample are artificial, and wherein a probability that is equal to or larger than about 0.05 indicates that the nucleic acids from the test sample are natural.

In one embodiment, determining the distribution of nucleic acid fragment lengths in the nucleic acids comprises:

(i) subjecting nucleic acids from a test sample to size fractionation; and (ii) detecting the fragment lengths and their corresponding intensitiesfor the nucleic acids;

In one embodiment, detecting RNA in the sample is by RT-PCR of one or more transcribed loci. In one embodiment, the DNA sample is from a biological sample selected from a group consisting of: blood, saliva, hair, semen, urine, feces, skin, epidermal cell, buccal cell, and bone. In a particular embodiment, the sample is a forensic sample. In one embodiment, the sample is derived from a human source.

In another aspect, the invention provides a kit for verifying that a DNA profile obtained from a sample represents natural DNA, the kit comprising two or more reagents selected from the group consisting of:

(a) primers for amplifying one or more profile-linking loci in the sample;

(b) primers for amplifying one or more methylated or partially methylated CG loci in the sample;

(c) primers for amplifying one or more CG loci in the sample, wherein the CG loci are known to be constitutively unmethylated in natural DNA;

(d) one or more methylation-sensitive restriction endonucleases;

(e) DNA polymerase enzyme;

(f) reagents for restriction and PCR;

and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:

(a) primers for profile-linking locus PL1: PL1forward—ttcgttctaaactatgacaagtgt (SEQ ID NO: 1); PL1reverse—ggtcaggctgactatggagtt (SEQ ID NO: 2).

(b) primers for constitutively methylated CG locus NT18: NT18forward—gctcggtgccaagcagctc (SEQ ID NO: 3); NT18reverse—ggagctgatgcaggctcttcc (SEQ ID NO: 4).

(c) primers for constitutively unmethylated CG locus SW14: SW14forward—gtggcgccatcttcggtaaa (SEQ ID NO: 5); SW14reverse—cgttaacaaagaccaagcagcgta (SEQ ID NO: 6).

(d) HpaII methylation-sensitive restriction endonuclease (e) DNA polymerase enzyme (f) reagents for restriction and PCR and instructions for using the kit to assay a DNA sample.

In another aspect, the invention provides a kit for verifying that a DNA profile obtained from a sample represents natural DNA, the kit comprising two or more reagents selected from the group consisting of:

(a) primers for amplifying one or more control loci in the sample;

(b) primers for amplifying one or more profile-linking loci in the sample;

(c) primers for amplifying one or more methylated or partially methylated CG loci in the sample;

(d) primers for amplifying one or more CG loci in the sample, wherein the CG loci are known to be constitutively unmethylated in natural DNA;

(e) one or more methylation-sensitive restriction endonucleases;

(f) DNA polymerase enzyme;

(g) reagents for restriction and PCR;

and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:

(a) primers for control locus CL1: CL1forward—agagag-gttgaaaggttttggtt (SEQ ID NO: 7); CL1reverse—tgagactca-gggcactgagc (SEQ ID NO: 8).

(b) primers for profile-linking locus PL1: PL1forward—ttcgttctaaactatgacaagtgt (SEQ ID NO: 1); PL1reverse—ggtcaggctgactatggagtt (SEQ ID NO: 2).

(c) primers for constitutively methylated CG locus NT18: NT18forward—gctcggtgccaagcagctc (SEQ ID NO: 3); NT18reverse—ggagctgatgcaggctcttcc (SEQ ID NO: 4).

(d) primers for constitutively unmethylated CG locus SW14: SW14forward—gtggcgccatcttcggtaaa (SEQ ID NO: 5); SW14reverse—cgttaacaaagaccaagcagcgta (SEQ ID NO: 6).

(e) HpaII methylation-sensitive restriction endonuclease (f) DNA polymerase enzyme (g) reagents for restriction and PCR and instructions for using the kit to assay a DNA sample.

In another aspect, the invention provides a kit for verifying that a DNA profile obtained from a sample represents natural DNA, the kit comprising two or more reagents selected from the group consisting of:

(a) primers for amplifying one or more profile-linking loci in the sample;

(b) primers for amplifying two or more bias-prone loci in the sample;

(c) DNA polymerase enzyme;

(d) reagents for restriction and PCR;

and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:

(a) primers for profile-linking locus PL1: PL1forward—ttcgttctaaactatgacaagtgt (SEQ ID NO: 1); PL1reverse—ggtcaggctgactatggagtt (SEQ ID NO: 2).

(b) primers for bias-prone loci BPL1 and BPL2: BPL1forward—acgtgacgatggagacaggag (SEQ ID NO: 9); BPL1reverse—cccagagctgaatgcagtagg (SEQ ID NO: 10); BPL2forward—gtggcgccatcttcggtaaa (SEQ ID NO: 5); BPL2reverse—cgttaacaaagaccaagcagcgta (SEQ ID NO: 6).

(c) DNA polymerase enzyme (d) reagents for PCR and instructions for using the kit to assay a DNA sample.

In another aspect, the invention provides a kit for verifying that a DNA profile obtained from a sample represents natural DNA, the kit comprising two or more reagents selected from the group consisting of:

(a) primers for amplifying one or more control loci in the sample;

(b) primers for amplifying one or more profile-linking loci in the sample;

(c) primers for amplifying two or more bias-prone loci in the sample;

(d) DNA polymerase enzyme;

(e) reagents for restriction and PCR;

and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:

(a) primers for control locus CL1: CL1forward—agagag-gttgaaaggttttggtt (SEQ ID NO: 7); CL1reverse—tgagactca-gggcactgagc (SEQ ID NO: 8).

(b) primers for profile-linking locus PL1: PL1forward—ttcgttctaaactatgacaagtgt (SEQ ID NO: 1); PL1reverse—ggtcaggctgactatggagtt (SEQ ID NO: 2).

(c) primers for bias-prone loci BPL1 and BPL2: BPL1forward—acgtgacgatggagacaggag (SEQ ID NO: 9); BPL1reverse—cccagagctgaatgcagtagg (SEQ ID NO: 10); BPL2forward—gtggcgccatcttcggtaaa (SEQ ID NO: 5); BPL2reverse—cgttaacaaagaccaagcagcgta (SEQ ID NO: 6).

(d) DNA polymerase enzyme (e) reagents for PCR and instructions for using the kit to assay a DNA sample.

In another aspect, the invention provides a kit for verifying that a DNA profile obtained from a sample represents natural DNA, the kit comprising two or more reagents selected from the group consisting of:

(a) primers for amplifying one or more profile-linking loci in the sample;

(b) primers for amplifying two or more bias-prone loci in the sample;

(c) primers for amplifying one or more slippage loci;

(d) DNA polymerase enzyme;

(e) reagents for restriction and PCR;

and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:

(a) primers for profile-linking locus PL1: PL1forward—ttcgttctaaactatgacaagtgt (SEQ ID NO: 1); PL1reverse—ggtcaggctgactatggagtt (SEQ ID NO: 2).

(b) primers for bias-prone loci BPL1 and BPL2: BPL1forward—acgtgacgatggagacaggag (SEQ ID NO: 9); BPL1reverse—cccagagctgaatgcagtagg (SEQ ID NO: 10); BPL2forward—gtggcgccatcttcggtaaa (SEQ ID NO: 5); BPL2reverse—cgttaacaaagaccaagcagcgta (SEQ ID NO: 6).

(c) primers for slippage loci SL1 SL2: SL1forward—acacgggcaagagtaagactcca (SEQ ID NO: 11); SL1reverse—ttcgggtgggggcaagggatc (SEQ ID NO: 12); SL2forward—taagaataatcagtatgtgacttgg (SEQ ID NO: 13); SL2reverse—atacataggatggatggatagatg (SEQ ID NO: 14).

(d) DNA polymerase enzyme (e) reagents for PCR and instructions for using the kit to assay a DNA sample.

In another aspect, the invention provides a kit for verifying that a DNA profile obtained from a sample represents natural DNA, the kit comprising two or more reagents selected from the group consisting of:
(a) primers for amplifying one or more control loci in the sample;
(b) primers for amplifying one or more profile-linking loci in the sample;
(c) primers for amplifying two or more bias-prone loci in the sample;
(d) primers for amplifying one or more slippage loci;

(e) DNA polymerase enzyme
(f) reagents for PCR
and instructions for using the kit to assay a DNA sample.

In one embodiment, the slippage loci are STRs. In one embodiment, the primers for amplifying the loci in the sample are CODIS STR primers. In one embodiment, the primers for amplifying one or more methylated or partially methylated loci are selected from the primers in Table 1:

TABLE 1

| Type | Name | Sequence | SEQ ID NO: |
| --- | --- | --- | --- |
| Control | CL1forward | agagaggttgaaaggttttggtt | 7 |
| Control | CL1reverse | tgagactcagggcactgagc | 8 |
| Profile-linking | PL1forward | ttcgttctaaactatgacaagtgt | 1 |
| Profile-linking | PL1reverse | ggtcaggctgactatggagtt | 2 |
| Constitutively methylated CG locus | NT18forward | gctcggtgccaagcagctc | 3 |
| Constitutively methylated CG locus | NT18reverse | ggagctgatgcaggctcttcc | 4 |
| Constitutively unmethylated CG locus | SW14forward | gtggcgccatcttcggtaaa | 5 |
| Bias-prone locus | BPL1forward | acgtgacgatggagacaggag | 9 |
| Bias-prone locus | BPL1reverse | cccagagctgaatgcagtagg | 10 |
| Bias-prone locus | BPL2forward | gtggcgccatcttcggtaaa | 5 |
| Bias-prone locus | BPL2reverse | cgttaacaaagaccaagcagcgta | 6 |
| Slippage locus | SL1forward | acacgggcaagagtaagactcca | 11 |
| Slippage locus | SL1reverse | ttcgggtgggggcaagggatc | 12 |
| Slippage locus | SL2forward | taagaataatcagtatgtgacttgg | 13 |
| Slippage locus | SL2reverse | atacataggatggatggatagatg | 14 |

(e) DNA polymerase enzyme;
(f) reagents for restriction and PCR;
and instructions for using the kit to assay a DNA sample.

One or more of the primers may be fluorescently labeled. In one embodiment, the kit further comprises reagents for PCR amplification, e.g., the reagents for PCR amplification may comprise a buffer and a thermostable polymerase.

In one embodiment, the kit comprises of the following ingredients:
(a) primers for control locus CL1: CL1forward—agagaggttgaaaggttttggtt (SEQ ID NO: 7); CL1reverse—tgagactcagggcactgagc (SEQ ID NO: 8).
(b) primers for profile-linking locus PL1: PL1forward—ttcgttctaaactatgacaagtgt (SEQ ID NO: 1); PL1reverse—ggtcaggctgactatggagtt (SEQ ID NO: 2).
(c) primers for bias-prone loci BPL1 and BPL2: BPL1forward—acgtgacgatggagacaggag (SEQ ID NO: 9); BPL1reverse—cccagagctgaatgcagtagg (SEQ ID NO: 10); BPL2forward—gtggcgccatcttcggtaaa (SEQ ID NO: 5); BPL2reverse—cgttaacaaagaccaagcagcgta (SEQ ID NO: 6).
(d) primers for slippage loci SL1 SL2: SL1forward—acacgggcaagagtaagactcca (SEQ ID NO: 11); SL1reverse—ttcgggtgggggcaagggatc (SEQ ID NO: 12); SL2forward—taagaataatcagtatgtgacttgg (SEQ ID NO: 13); SL2reverse—atacataggatggatggatagatg (SEQ ID NO: 14).

In one embodiment, the methylated, partially methylated, and constitutively unmethylated loci used are chosen from the sequences that are shown in the Sequences section elsewhere in this specification.

In one embodiment, the one or more methylation-sensitive restriction endonucleases are selected from the group consisting of: HpaII, HhaI, AciI, BstUI, HpyCH4, McrBc

BRIEF DESCRIPTION OF THE FIGURES

FIG. 2A-C demonstrates DNA profiles of artificial mock forensic samples. FIG. 2A (1-3) shows the DNA profile that was obtained from sample 1 (genuine blood sample of individual A on cotton). FIG. 2B (1-3) shows the DNA profile that was obtained from sample 2 (genuine blood sample of individual B on cotton). FIG. 2C (1-3) shows the DNA profile that was obtained from sample 3 (fake blood sample on cotton, composed of red blood cells of individual A mixed with in vitro generated copies of DNA from individual B).

DETAILED DESCRIPTION

Figure 1:
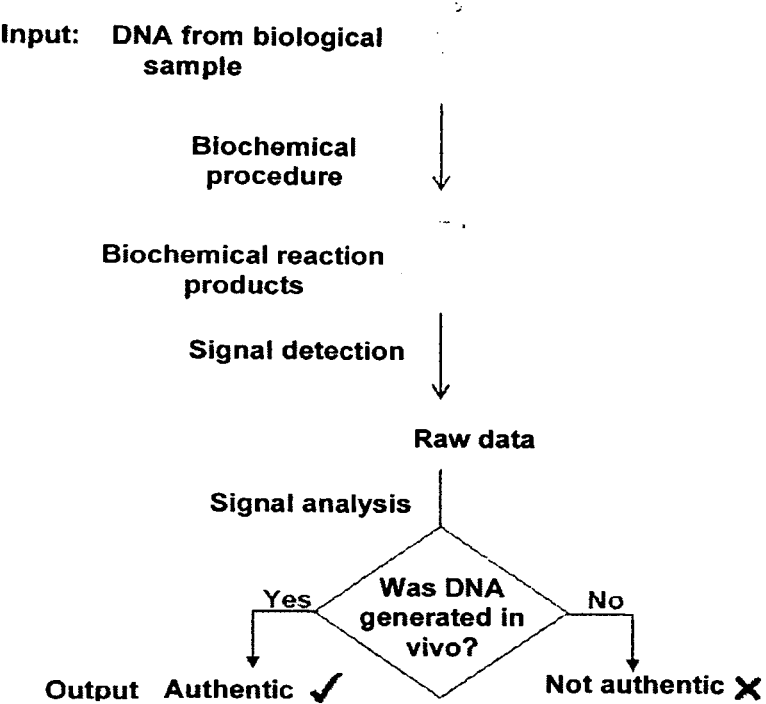
FIG. 1 demonstrates a general scheme of the DNA authentication procedure.

DNA samples are often profiled for identification of their specific source (i.e. the specific individual). Such DNA samples may be susceptible to contamination by artificial DNA, i.e. DNA that was synthesized in vitro. Thus, in one aspect, the invention provides methods for distinguishing between natural and artificial DNA. In another aspect the invention provides methods for verifying that the DNA profiles represent natural DNA. In one embodiment, the invention provides methods for verifying that a DNA profile is of natural DNA, originating from human subjects rather than of artificial DNA that was synthesized by techniques such as PCR, cloning in prokaryotic systems, Whole Genome Amplification (WGA), etc.

Any and all of the embodiments described in the Summary section exemplify various embodiments of the present invention. In an illustrative embodiment, the invention also provides methods to verify that profiles of DNA samples are of human subjects in the context of various types of tissues (e.g. blood, saliva, etc.), as those found in crime scenes. For DNA profiling, the DNA samples obtained from blood, saliva etc., found in crime scenes, are amplified with a panel of STR markers, such as CODIS. Although STR-based profiling has enormous discriminatory power (each person is considered to have a unique profile), it cannot differentiate between a natural DNA sample found at the scene of the crime and an artificial DNA sample that was produced, for example, using PCR, cloning, or Whole Genome Amplification (WGA). The DNA profile obtained from such artificial DNA is indistinguishable from the profile of natural DNA using the typical methods in the art. Furthermore, an artificial DNA can reproduce any specific DNA profile that can be found in crime scenes. Since DNA profiles from crime scenes are used as evidence in court of law for indictment, there is a need to develop methods for verifying that a forensic DNA profile is of natural DNA.

The inventors discovered that "normal" DNA profiles (i.e. which have no anomalies in any analyzed locus such as additional alleles, allelic imbalances, out of range peak heights) can be obtained not only from natural DNA, but also from artificial DNA that was synthesized by different in vitro methods. The inventors investigated different methods for synthesizing artificial DNA and characterized different DNA species that upon profiling can generate a normal profile:

Chemically Synthesized Oligonucleotides

Synthesized oligonucleotides can be synthesized with the same sequence as CODIS alleles or other alleles that are used for profiling.

Products of PCR Amplification of Target Sequences

PCR amplification products that upon profiling can yield a normal profile include, for example, PCR-amplified human CODIS alleles or other alleles that are used for profiling. These products may be amplified from a template of natural DNA or from an artificial template such as, for example, synthesized oligonucleotides. The amplification of such alleles can be performed in multiple singleplex reactions, or in a single multiplex reaction.

Products of Rolling Circle Amplification (RCA) of Circular Target Sequences

Any circular target can be amplified in an isothermal reaction using RCA. When the targets correspond to CODIS alleles or other alleles that are used for profiling, the products of amplification can, upon profiling, yield a normal profile.

Products of Molecular Cloning

Molecular cloning enables the production of very large quantities of target sequences. A common example of molecular cloning is inserting a desired human sequence (e.g. a CODIS allele or a different allele that is used for profiling) into a cloning vector or plasmid (e.g. pGEM-T). By cloning an array of such alleles, a "CODIS allele library", consisting of individual cloned alleles, can be created. For example, one element in the library may consist of a microcentrifuge tube with trillions of copies of allele 11 (with 11 repeat units) of locus D8S1179, while another element contains allele 12 (with 12 repeat units) of D8S1179 (and likewise for the other CODIS loci). The inventors discovered that, for example, a library containing 425 clones corresponding to all known CODIS alleles (including all rare micro-variants) is sufficient to generate any desired CODIS profile, and a much smaller library is sufficient to generate the CODIS profiles of the vast majority of the population. For assembling a desired profile from the library, alleles corresponding to the profile are combined in a single tube. Profiling of such a sample yields a normal profile.

Assembly of DNA Fragments and/or Products Synthesized by Different Methods

DNA fragments and/or products that were generated by different methods can be assembled together. The DNA fragments can include, for example, chemically synthesized oligonucleotides, products of PCR amplification of target sequences, products of RCA, and products of molecular cloning. The assembly can be achieved by different molecular biology techniques such as, for example, annealing, ligation, polymerization, or by a combination of them. The process of assembly may also include steps of breaking or degrading DNA molecules (e.g. by restriction endonucleases or exonucleases, mechanical shearing, hydrolysis etc.).

Products of PCR-Based Whole Genome Amplification (WGA) and Similar Techniques

PCR-based WGA techniques include, for example, primer extension preamplification (PEP)-PCR and degenerate oligonucleotide primed (DOP)-PCR. In addition, similar techniques include, for example, T7-based linear amplification of DNA (TLAD), ligation mediated PCR (LMP)-based WGA methods, and combinations of these methods. Commercial kits employing such techniques include, for example, the Genomeplex (Sigma) kit that utilizes Adaptor-Ligation PCR. WGA represents a method in which nanogram quantities of genomic DNA are amplified in just a few hours to microgram quantities, and the amplified products contain a representation of the entire genome.

Products of Multiple Displacement Amplification (MDA) and Restriction and Circularization-Aided Rolling Circle Amplification (RCA-RCA).

MDA is a recently developed isothermal WGA in which nanogram quantities of genomic DNA are amplified overnight, or in just a few hours, to microgram quantities, and the amplified products contain a representation of the entire genome. The Repli-G (Qiagen), and GenomiPhi (GE Healthcare) commercial kits utilize this method.

Mixtures of Artificial DNA Fragments and/or Products Synthesized by Different Methods Mixtures of artificial DNA fragments and/or products synthesized by different methods can yield a normal profile. The mixture can consist of for example, chemically-synthesized oligonucleotides, products of PCR amplification of target sequences, products of RCA of circular target sequences, products of molecular cloning, assembled DNA fragments, products of PCR-based WGA, products of MDA, and products of RCA-RCA.

Artificial DNA Fragments and/or Products that were Methylated In Vitro

Artificially created DNA fragments and/or products synthesized by different methods (for example, by PCR, molecular cloning etc.) can be methylated in vitro following their synthesis. This can be achieved, for example, by Sss1 methylase.

Mixtures of Natural and Artificial DNA

The inventors also discovered that mixtures of natural and artificial DNA can also yield normal profiles, and in the case where the artificial component of such a mixture is dominant, the resulting profile represents only the artificial element in the mixture, without any trace of the natural element (i.e. a single contributor profile). Therefore, for example, a mixture containing a small amount of natural DNA of individual A and a large amount of artificial DNA with the profile of individual B will, upon profiling, produce a normal, single contributor profile that is identical to the profile of individual B.

Some of the methods for synthesizing artificial DNA require only basic biological know-how and equipment, and can be performed quickly, with little financial expense. For example, by performing an over-night reaction in a water-bath at 30° C., using a commercial kit for MDA, virtually unlimited amounts of artificial DNA can be duplicated from minute amounts of a natural DNA source. Furthermore, in vitro synthesis methods allow the manufacturing of DNA samples with all possible profiles, and in some methods (e.g. molecular cloning), this can be achieved even without any natural DNA as template. Once artificial DNA is synthesized, it can accidentally contaminate, or deliberately be incorporated into natural biological tissues such as blood or saliva. In the forensic setting, such contaminated tissues might cause a problem because they can pass the entire forensic procedure as regular specimens, yet upon profiling, they yield the DNA profile of their artificial element.

Because the profiles obtained from artificial DNA may be identical to the profiles obtained from natural DNA of individuals, it is important to identify samples that contain artificial DNA and to verify that profiles of DNA samples are indeed of natural DNA, in order to verify the integrity for the entire assay. In the context of some embodiments, DNA profiles from crime scenes are used as evidence in court of law for indictment; therefore, the assurance that such profiles are of genuine (i.e. natural) DNA is of utmost importance.

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein.

In practicing the present invention, many conventional techniques in molecular biology and recombinant DNA are used. These techniques are explained in, e.g., *Current Protocols in Molecular Biology*, Vols. I-III, Ausubel, Ed.

(1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybrikation*, Hames & Higgins, Eds. (1985); *Transcription and Translation*, Hames & Higgins, Eds. (1984); Perbal, *A Practical Guide to Molecular Cloning*, the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

The present technology is described herein using several definitions, as set forth throughout the specification. Unless defined otherwise, all technical and scientific terms used herein generally have the same meaning as commonly understood by one of ordinary skill in the art to which this invention belongs. As used herein, unless otherwise stated, the singular forms "a," "an," and "the" include plural reference. Thus, for example, a reference to "a nucleic acid" is a reference to one or more nucleic acids.

As used herein, the term "allele" is intended to be a genetic variation associated with a segment of DNA, i.e., one of two or more alternate forms of a DNA sequence occupying the same locus.

The term "artificial DNA" or "artificial nucleic acid" as used herein refers to a nucleic acid which is synthesized by various in vitro methods. Such in vitro generated nucleic acids include, but are not limited to, 1. Chemically synthesized oligonucleotides
2. Products of PCR amplification of target sequences
3. Products of Rolling circle amplification (RCA) of circular target sequences
4. Products of molecular cloning (e.g. plasmids cloned in *E. coli*)
5. DNA fragments assembled from other DNA fragments that were generated by any of methods 1-4, or a combination of them. Such assembly being achieved by any of the following methods (or a combination of them): annealing, ligation, polymerization. The process of assembly may also include steps of breaking DNA molecules (e.g. by restriction endonucleases, mechanical shearing etc.)
6. Products of PCR-based Whole genome amplification (WGA), and/or ligation mediated PCR (LMP)-based WGA methods, including primer extension preamplification (PEP)-PCR, degenerate oligonucleotide primed (DOP)-PCR, T7-based linear amplification of DNA (TLAD), Adaptor-Ligation PCR. The Genomeplex (Sigma) commercial kit utilizes Adaptor-Ligation PCR.
7. Products of WGA by Multiple displacement amplification (MDA) and Restriction and Circularization-Aided Rolling Circle Amplification (RCA-RCA). The Repli-G (Qiagen), and GenomiPhi (GE Healthcare) commercial kits utilize this method.
8. A mix of products from any of 1-7
9. Products from any of 1-8 in which all or some products were methylated in vitro following their synthesis (e.g. by Sss1 Methylase).
10. Products from any of 1-8 mixed with natural DNA
11. Products from 9 mixed with natural DNA The term "biological sample" or "test sample" as used herein, refers to, but is not limited to, any biological sample derived from a subject. The sample suitably contains nucleic acids. In some embodiments, samples are not directly retrieved from the subject, but are collected from the environment, e.g. a crime scene or a rape victim. Examples of such samples include fluids, tissues, cell samples, organs, biopsies, etc. Suitable samples are blood, plasma, saliva, urine, sperm, hair, etc. The biological sample can also be blood drops, dried blood stains, dried saliva stains, dried underwear stains (e.g. stains on underwear, pads, tampons, diapers), clothing, dental floss, ear wax, electric razor clippings, gum, hair, licked envelope, nails, paraffin embedded tissue, post mortem tissue, razors, teeth, toothbrush, toothpick, dried umbilical cord. Genomic DNA can be extracted from such samples according to methods known in the art.

The term "capillary electrophoresis histogram" as used herein refers to a histogram obtained from capillary electrophoresis of PCR products wherein the products were amplified from genomic loci with fluorescent primers.

The term "CG locus" refers to a genomic sequence that contains one or more CG dinucleotides.

The term "constitutively-methylated" as used herein means methylated at a level of at least 80% (i.e. at least 80% of the DNA molecules methylated) in DNA of cells of tissues including blood, saliva, semen, epidermis, nasal discharge, buccal cells, hair, nail clippings, menstrual excretion, vaginal cells, urine, and feces.

The term "partially-methylated" as used herein means methylated at a level between 20-80% (i.e. between 20-80% of the DNA molecules methylated) in DNA of cells of tissues including blood, saliva, semen, epidermis, nasal discharge, buccal cells, hair, nail clippings, menstrual excretion, vaginal cells, urine, and feces.

The term "constitutively-unmethylated" as used herein means methylated at a level less than 20% (i.e. less than 20% of the DNA molecules methylated) in DNA of cells of tissues including blood, saliva, semen, epidermis, nasal discharge, buccal cells, hair, nail clippings, menstrual excretion, vaginal cells, urine, bone, and feces. The methods provided herein have been demonstrated to distinguish methylated and unmethylated forms of nucleic acid loci in various tissues and cell types including blood, saliva, semen, epidermis, nasal discharge, buccal cells, hair, nail clippings, menstrual excretion, vaginal cells, urine, bone, and feces.

The term "profile-linking" as used herein means a genomic locus that was used for profiling of the DNA sample.

The term "bias-prone" as used herein means genomic loci whose representation bias is greater in artificial DNA in relation to natural DNA.

The term "slippage" as used herein means a genomic locus that is prone to DNA polymerase slippage.

The terms "determining," "measuring," "assessing," "assaying", and "evaluating" are used interchangeably to refer to any form of quantitative or qualitative measurement, and include determining if a characteristic, trait, or feature is present or not. Assessing may be relative or absolute. "Assessing the presence of" includes determining the amount of something present, as well as determining whether it is present or absent.

The term "forensics" or "forensic science" as used herein refers to the application of a broad spectrum of methods aimed to answer questions of identity being of interest to the legal system. For example, the identification of potential suspects whose DNA may match evidence left at crime scenes, the exoneration of persons wrongly accused of crimes, identification of crime and catastrophe victims, or establishment of paternity and other family relationships.

The term "locus" (plural—loci) refers to a position on a chromosome of a gene or other genetic element. Locus may also mean the DNA at that position. A variant of the DNA sequence at a given locus is called an allele. Alleles of a locus are located at identical sites on homologous chromosomes.

The term "natural DNA" or "natural nucleic acid" as used herein refers to, but is not limited to, nucleic acid which originates directly from the cells of a subject without modification or amplification.

The term "nucleic acid" as used herein refers to, but is not limited to, genomic DNA, cDNA, hnRNA, mRNA, rRNA, tRNA, fragmented nucleic acid, and nucleic acid obtained from subcellular organelles such as mitochondria. In addition, nucleic acids include, but are not limited to, synthetic nucleic acids or in vitro transcription products.

The term "nucleic-acid based analysis procedures" as used herein refers to any identification procedure which is based on the analysis of nucleic acids, e.g. DNA profiling.

The term "Relative Copy Number" (RCN), as used herein refers to the ratio of the copy number of a locus/allele to the copy number of a reference locus/allele.

The term "polymerase chain reaction (PCR) stutter" as used herein refers to PCR byproducts, obtained along with the main PCR product. These "stutter" byproducts are usually shorter by multiples of the repeated unit produced in the course of PCR amplification of STR sequences. The mechanism by which these artifacts are formed is understood, but it represents an intrinsic limitation of the PCR technology and therefore no effective remedy has been found to eliminate these spurious products (Olejniczak M, Krzyzosiak W J., *Electrophoresis.* 2006 October; 27(19): 3724-34). The term "−1 stutter" as used herein refers to a stutter byproduct that is one repeat unit smaller than its associated allele. Similarly, "+1 stutter" refers to a stutter byproduct that is one repeat unit larger than its associated allele. The term '−1 stutter fraction' refers to the height (or area) of the −1 stutter peak divided by the height (or area) of the true allele peak. Similarly, "+1 stutter fraction" refers to the height (or area) of the +1 stutter peak divided by the height (or area) of the true allele peak.

The term "Restriction and Circularization-Aided Rolling Circle Amplification (RCA-RCA)" refers to a whole genome amplification procedure which retains the allelic differences among degraded amplified genomes while achieving almost complete genome coverage. RCA-RCA utilizes restriction digestion and whole genome circularization to generate genomic sequences amenable to rolling circle amplification.

The term "STR primers" as used herein refers to any commercially available or made-in-the-lab nucleotide primers that can be used to amplify a target nucleic acid sequence from a biological sample by PCR. There are ~1.5 million non-CODIS STR loci. In addition to published primer sequences, STR primers may be obtained from commercial kits for amplification of hundreds of STR loci (for example—ABI Prism Linkage Mapping Set-MD10—Applied Biosystems), and for amplification of thousands of SNP loci (for example—Illumina BeadArray linkage mapping panel). The term "CODIS STR primers" as used herein refers to STR primers that are designed to amplify any of the thirteen core STR loci designated by the FBI's "Combined DNA Index System", specifically, the repeated sequences of TH01, TPOX, CSF1PO, VWA, FGA, D3S1358, D5S818, D7S820, D13S317, D16S539, D8S1179, D18S51, and D21S11, and the Amelogenin locus.

The term "representation bias" as used herein refers to differences in copy-number between different genomic loci in the nucleic acid sample in question.

STR Analysis and Forensic Testing

Methods for DNA fingerprinting include Restriction Fragment Length Polymorphism (RFLP), Amplified Fragment Length Polymorphism (AFLP), short tandem repeat (STR) analysis. In one aspect, the methods for distinguishing natural from artificial DNA are used in the context of STR analysis. STR analysis is the most prevalent method of DNA fingerprinting used today. The polymorphisms displayed at each STR region are by themselves very common, typically each polymorphism is shared by around 5-20% of individuals. When looking at multiple loci, it is the unique combination of these polymorphisms in an individual that makes this method discriminating as an identification tool. The more STR regions that are tested in an individual, the more discriminating the test becomes.

Different STR-based DNA profiling systems are in use in different countries. In North America, systems which amplify the CODIS 13 core loci are almost always used, while in the UK the SGM+system, which is compatible with The National DNA Database is used. Whichever system is used, many of the STR regions under test are the same. These DNA profiling systems are based around multiplex reactions, whereby many STR regions are tested simultaneously.

Capillary electrophoresis is performed by electro-kinetically injecting the DNA fragments into a capillary, filled with polymer. The DNA is pulled through the tube by the application of an electric field, separating the fragments such that the smaller fragments travel faster through the capillary. The fragments are then detected using fluorescent dyes that were attached to the primers used in PCR. This allows multiple fragments to be amplified and run simultaneously, also known as multiplexing. Sizes are assigned using labeled DNA size standards that are added to each sample, and the number of repeats is determined by comparing the size to an allelic ladder, a sample that contains all of the common possible repeat sizes. Although this method is expensive, larger capacity machines with higher throughput are being used to lower the cost/sample and reduce backlogs that exist in many government crime facilities.

Gel electrophoresis acts using similar principles as CE, but instead of using a capillary, a large polyacrylamide gel is used to separate the DNA fragments. An electric field is applied, as in CE, but instead of detection being performed at a single location in the capillary, the entire gel is scanned into a computer, and all fragments are detected simultaneously. This produces an image showing all of the bands corresponding to different repeat sizes and the allelic ladder. This approach does not require the use of size standards, since the allelic ladder is run alongside the samples and serves this purpose. Visualization can either be through the use of fluorescently tagged dyes in the primers or by silver staining the gel prior to scanning.

In the U.S.A., there are 13 core loci that are currently used for discrimination in CODIS. Because these loci are independently assorted (having a certain number of repeats at one locus does not change the likelihood of having any number of repeats at any other locus), the product rule for probabilities can be applied. This has resulted in the ability to generate match probabilities of one in a quintillion or more. The CODIS is the FBI-funded computer system that solves crimes by searching DNA profiles developed by federal, state, and local crime laboratories.

A record in the CODIS database, known as a CODIS profile, consists of a sample identifier, an identifier for the laboratory responsible for the profile, and the results of the DNA analysis (known as the DNA profile). Other than the DNA profile, CODIS does not contain any personal identity information—the system does not store names, dates of birth, social security numbers, etc.

In its original form, CODIS consisted of two indexes: the Convicted Offender Index and the Forensic Index. The Convicted Offender Index contains profiles of individuals convicted of crimes; state law governs which specific crimes are eligible for CODIS. The Forensic Index contains profiles developed from biological material found at crime-scenes. In the past several years, CODIS has added several other indexes, including: an Arrestee Index, a Missing or Unidentified Persons Index, and a Missing Persons Reference Index.

CODIS has a matching algorithm that searches the various indexes against one another according to strict rules that protect personal privacy. For identifying suspects in rape and homicide cases, CODIS searches the Forensic Index against itself and against the Offender Index. A Forensic to Forensic match provides an investigative lead that connects two or more previously unlinked cases. A Forensic to Offender match actually provides a suspect for an otherwise unsolved case. It is important to note that the CODIS matching algorithm only produces a list of candidate matches. Each candidate match is confirmed or refuted by a Qualified DNA Analyst.

CODIS databases exist at the local, state, and national levels. This tiered architecture allows crime laboratories to control their own data—each laboratory decides which profiles it will share with the rest of the country. As of 2006, approximately 180 laboratories in all 50 states in the US participate in CODIS. The national level, the National DNA Index System (NDIS), are operated by the FBI at an undisclosed location As of May 2007, 177,870 forensic profiles and 4,582,516 offender profiles have been accumulated, making it the largest DNA databank in the world, surpassing the United Kingdom's National DNA Database, which consisted of an estimated 3,976,090 profiles as of June 2007. As of the same date, CODIS has produced over 49,400 matches to requests, assisting in more than 50,343 investigations.

The growing public approval of DNA databases has seen the creation and expansion of many states' own DNA databanks. California currently maintains the third largest DNA databank in the world. Political measures such as California Proposition 69 (2004), which increased the scope of the databank, have already met with a significant increase in numbers of investigations aided.

In order to decrease the number of irrelevant matches at NDIS, the Convicted Offender Index requires all 13 CODIS STRs to be present for a profile upload. Forensic profiles only require 10 of the STRs to be present for an upload.

The CODIS profile is created by genotyping 13 STR loci, plus two additional genomic loci located on chromosomes X, Y—for determination of sex. The CODIS profile consists of a vector of 26 numbers (representing the allelic values of the maternal and paternal alleles of the 13 STR loci), and the letters XX or XY (representing male or female). Each profile has an associated "frequency", which represents the chance for a randomly picked person to have that profile. The frequency of the profile is the product of all the individual allelic frequencies.

Methods for Distinguishing Between Natural and Artificial DNA Samples.

In one aspect, the present invention provides a method for distinguishing between natural and artificial DNA samples. A general scheme of the invention is as follows: the method accepts as input a DNA sample. The DNA undergoes a procedure including one or more biochemical steps followed by signal detection. In the last step of the procedure, the signal is analyzed to determine whether the DNA is natural or artificial. In another aspect, the present invention provides a method for verifying that a DNA profile is of natural DNA. A general scheme of the invention is as follows: the method accepts as an input a DNA sample that underwent profiling (e.g. with Identifiler). The DNA sample undergoes a verification procedure which includes one or more biochemical steps followed by signal detection. In the last step of the entire procedure, data from both profiling and verification of the DNA sample are analyzed. The signal analysis determines whether the profile obtained from the DNA sample represents natural (in vivo) or artificial (in vitro) DNA. When the verification procedure determines that a DNA sample is artificial, there may be no need to profile the sample. Therefore, the invention can also be useful for avoiding unnecessary profiling reactions. The invention also includes an internal validation step that can detect failure of amplification due to problems such as insufficient amount of template DNA, presence of PCR inhibitors, etc.

In various aspects, the methods of the present invention concern the verification that DNA profiles represent natural DNA. The methods are employed on a DNA sample in question, for example, DNA from a blood sample found at a crime scene. The isolation of nucleic acids (e.g. DNA) from a biological sample may be achieved by various methods known in the art (e.g. see Sambrook et al, (1989) *Molecular Cloning: A Laboratory Manual,* 2nd ed. Cold Spring Harbor, N.Y.).

Distinguishing between natural and artificial DNA, or the determination whether a DNA profile represents natural DNA, may be accomplished using various strategies, including those described in the following sections.

Methylation

Methylation in the human genome occurs in the form of 5-methyl cytosine and is confined to cytosine residues that are part of the sequence CG (cytosine residues that are part of other sequences are not methylated).

Some CG dinucleotides in the human genome are methylated, and others are not. In addition, methylation is cell and tissue specific, such that a specific CG dinucleotide can be methylated in a certain cell and at the same time unmethylated in a different cell, or methylated in a certain tissue and at the same time unmethylated in different tissues. Since methylation at a specific locus can vary from cell to cell, when analyzing the methylation status of DNA extracted from a plurality of cells (e.g. from a forensic sample), the signal can be mixed, showing both the methylated and unmethylated signals in varying ratios. The methylation status of different genomic loci has been investigated and published (for example, see Eckhardt F et al. DNA methylation profiling of human chromosomes 6, 20 and 22. *Nature Genetics* 2006, 38:1359-1360). Some genomic regions have been shown to be mostly methylated, some have been shown to be mostly unmethylated, and some regions have been shown to be mostly methylated in certain tissues but mostly unmethylated in other tissues. The inventors discovered that in some genomic regions all CG loci are constitutively methylated. These regions are provided in Table 1 and in the section herein entitled Sequences. The inventors also discovered that in some genomic regions all CG loci are partially methylated. These regions are provided in Table 1 and in the section herein entitled Sequences. The inventors also discovered that in some genomic regions all CG loci are constitutively unmethylated. These regions are provided in Table 1 and in the section herein entitled Sequences. The inventors also discovered contiguous genomic regions containing constitutively methylated, partially methylated, and constitutively unmethylated CG loci. These regions are provided in Table 1 and in the section herein entitled Sequences. There are several different methods for determining the methylation level of genomic loci. Examples of methods that are commonly used are bisulfite sequencing, methylation-specific PCR, and methylation-sensitive endonuclease digestion. Further, various data sources are available for retrieving or storing DNA methylation data and making these data readily available to the public, for example MetDB.

Exemplary methods for determining the methylation level of nucleic acids include, but are not limited to the following methods:

Bisulfite Sequencing.

Bisulfite sequencing is the sequencing of bisulfite treated-DNA to determine its pattern of methylation. The method is based on the fact that treatment of DNA with sodium bisulfite results in conversion of non-methylated cytosine residues to uracil, while leaving the methylated cytosine residues unaffected. Following conversion by sodium bisulfite, specific regions of the DNA are amplified by PCR, and the PCR products are sequenced. Since in the polymerase chain reaction uracil residues are amplified as if they were thymine residues, unmethylated cytosine residues in the original DNA appear as thymine residues in the sequenced PCR product, whereas methylated cytosine residues in the original DNA appear as cytosine residues in the sequenced PCR product.

Methylation Specific PCR.

Methylation specific PCR is a method of methylation analysis that, like bisulfite sequencing, is also performed on bisulfite-treated DNA, but avoids the need to sequence the genomic region of interest. Instead, the selected region in the bisulfite-treated DNA is amplified by PCR using two sets of primers that are designed to anneal to the same genomic targets. The primer pairs are designed to be "methylated-specific" by including sequences complementing only unconverted 5-methylcytosines, or conversely "unmethylated-specific", complementing thymines converted from unmethylated cytosines. Methylation is determined by the relative efficiency of the different primer pairs in achieving amplification.

It should be understood in the context of the present invention that methylation specific PCR determines the methylation level of CG dinucleotides in the primer sequences only, and not in the entire genomic region that is amplified by PCR. Therefore, CG dinucleotides that are found in the amplified sequence but are not in the primer sequences are not part of the CG locus.

Methylation-Sensitive Endonuclease Digestion.

Digestion of DNA with methylation-sensitive endonucleases represents a method for methylation analysis that can be applied directly to genomic DNA without the need to perform bisulfite conversion. The method is based on the fact that methylation-sensitive endonucleases digest only unmethylated DNA, while leaving methylated DNA intact. Following digestion, the DNA can be analyzed for methylation level by a variety of methods, including gel electrophoresis, and PCR amplification of specific loci.

In the procedure based on methylation-sensitive endonuclease digestion, each CG locus is comprised of one or more CG dinucleotides that are part of recognition sequence(s) of the methylation-sensitive restriction endonuclease(s) that are used in the procedure. CG dinucleotides that are found in the amplified genomic region, but are not in the recognition sequence(s) of the endonuclease(s) are not part of the CG locus.

In one embodiment, the one or more CG loci that are detected are partially methylated in natural DNA, but would be unmethylated in artificial DNA. Partial methylation would be expected to result in a mixture of T and C at the position being interrogated. Hybridization would be observed to both the T specific probes/primers and the C specific probes/primers, similar to detection of a heterozygous SNP. Relative amounts of hybridization may be used to determine the relative amount of methylation. Alternatively, both C and T would be observed upon bisulfite sequencing. Alternatively, fluorescent signals corresponding to amplification products of methylated or partially methylated CG loci can be detected.

Control Loci

Any genomic locus may be used as a control locus, other than those loci that are used for other purposes in the procedure (e.g. profile-linking loci). If the in vitro generated DNA sample consists only of loci used in the assay, except for the control loci, then all other genomic loci will be absent from the sample. Therefore, the attempt to amplify any additional locus will fail in such in vitro generated DNA samples, but not in in vivo generated DNA samples. Accordingly, the absence of control loci from the test sample indicates that the DNA was synthetically constructed.

A person skilled in the art needs no special guidelines for selection of control loci, as any loci will be appropriate for this purpose. If, however, the set of control loci is meant not only for distinguishing between natural and artificial DNA but also for DNA profiling, then the usual guidelines for selection of profiling loci (e.g. polymorphic in the human population, having relatively low mutation rates, neutral, non-phenotypic, each locus present on a separate chromosome) may be employed.

Therefore, in accordance with the present invention, the presence or absence of a set of genomic loci may be determined using various methods. In one embodiment, each locus in the set of loci is amplified by PCR and the presence of amplification products is detected by gel or capillary electrophoresis. Various amplification methods can be used to amplify DNA loci, including PCR (Saiki et al., *Science.* 1985, 230: 1350-1354), transcription based amplification (Kwoh et al., *Am Biotechnol Lab.* 1990, 8(13):14-25) and strand displacement amplification (SDA) (Walker et al., *Proc Natl Acad Sci* USA. 1992 1; 89(1):392-6). In a suitable embodiment, the nucleic acid sample is subjected to PCR amplification using primer pairs specific to each locus in the set.

Representation Bias

Natural DNA generally has a smaller representation bias in relation to WGA DNA. However, the pattern of representation bias in different types of WGA-DNA is different, such that in a specific set of loci there may be increased bias in one WGA type, but not in another. In the methods described here the loci used for representation bias analysis may be chosen as follows. In one embodiment, the analysis may be performed on a set of STR loci used for DNA profiling, such as the SGM+ or Identifiler loci. In accordance with the above, analysis is performed on the same capillary electrophoresis histogram that is used for profiling. In another embodiment, random genomic loci are tested for representation bias in natural and in artificial DNA, and those loci that show a high representation bias in artificial DNA are selected. The inventors discovered specific genomic loci that show increased representation bias in artificial DNA in relation to natural DNA loci. Such useful loci and primers are presented in Table 1 and the Sequences section elsewhere herein.

PCR Stutter

The present inventors discovered that artificial DNA that was synthesized by PCR or by any PCR-based WGA method (e.g. DOP-PCR) has increased stutter levels in relation to natural DNA in stutter-prone loci, such as repetitive elements. Furthermore, the present inventors discovered that artificial DNA that was synthesized by PCR or by any PCR-based WGA method (e.g. DOP-PCR) has increased stutter levels in relation to natural DNA in STR loci that are commonly used for profiling, such as the STR loci used in PowerPlex16, PowerPlexES, Identifiler, YFiler. Stutter-prone loci can be chosen from a large number of repetitive genetic elements such as STRs.

Non Genomic Sequences

The present inventors found and characterized non-genomic sequences, including primers, primer dimers, and additional adenine nucleotides (in DNA generated by PCR-based methods), plasmid sequences (in DNA generated by cloning methods), non-genomic sequences ligated to ends of genomic sequences (e.g. in ligation-mediated PCR), non-genomic sequences created by non-template polymerization (e.g. in MDA), in artificially synthesized DNA samples.

The presence of such non-genomic sequences can be detected by assays which are well-known in the art, for example, by cloning of the nucleic acids from the test sample into bacteria, and sequencing the cloned molecules.

Distribution of Nucleic Acid Fragment Lengths

Non-degraded, in vivo generated DNA that is extracted from biological samples by standard procedures typically consists of a distribution of fragments of varying lengths, from about 500 base pairs (bps) up to more than 10,000 bps. In contrast, DNA generated in vitro may consist of either small fragments only (e.g. DNA generated by PCR), or fragments with a relatively uniform size distribution (e.g. cloned DNA).

The distribution of fragment lengths may be determined by assays which are well-known in the art, for example, gel electrophoresis and detection of size-fractionated molecules.

RNA

Pure in vitro generated DNA does not contain RNA. However, it should be noted that if a contaminated sample contains some biological material (e.g. red blood cells extracted from fractionated blood), then some residual RNA may be present in the contaminated sample. However, this RNA will most likely not be compatible with the in vitro generated DNA that is found in the sample. This incompatibility can be detected by genotyping a set of transcribed STRs (e.g. RT-PCR followed by capillary electrophoresis).

Systems for Performing the Methods of the Invention

In another aspect, the invention provides a system for distinguishing between natural and artificial DNA, or for verifying that a DNA profile represents natural DNA. The system may comprise an input device in data communication with a processor, which is in data communication with an output device.

The input device is used for entry of data including the presence or amount of one or more target loci in the sample; one or more constitutively methylated or partially methylated loci in the sample; one or more constitutively unmethylated loci in the sample; non-genomic sequences in the sample; PCR stutter in the sample; and/or RNA in the sample. The processor may comprise software for computing a representation bias in the sample. The processor may also comprise software for determining whether the DNA sample in question is natural or artificial, or whether a DNA profile represents natural or artificial DNA.

The data output device, in data communication with the processor, receives the determination from the processor and provides the determination of whether the sample is natural or artificial to the system operator. The output device can consist of, for example, a video display monitor or a printer.

EXAMPLES

The present methods and kits, thus generally described, will be understood more readily by reference to the following examples, which are provided by way of illustration and are not intended to be limiting of the present methods and kits.

Example 1

Materials and Methods

Collection of Biological Tissues.

Samples of blood, dry saliva stains on absorbent paper, skin scrapings, hair, and smoked cigarette butts were collected from volunteers. Informed consent was obtained from all participants recruited into the study. DNA from these samples was extracted and quantified as described below.

In Vitro Synthesis of DNA.

The set of 10 STRs included in the Profiler Plus® kit (Applied Biosystems) were amplified from 1 ng of natural DNA, either by singleplex PCR amplification of all 10 loci (performed as described below), or by simultaneous amplification of all loci in a single reaction using the Profiler Plus® kit.

For construction of the CODIS allele library, individual alleles of CODIS STRs and the hTERT locus were amplified from pooled DNA (Control Human Genomic DNA of the GenomePlex WGA2 kit, Sigma Aldrich) by separate PCR reactions. Amplified fragments were purified (QIAquick PCR purification kit, QIAGEN), and cloned into the pGEM-T-Easy vector (Promega). Plasmid DNA was purified by the QIAprep Spin Miniprep kit (QIAGEN), and groups of clones were genotyped simultaneously using the PowerPlex16 kit (Promega).

Whole genome amplification was performed with the Repli-g Midi kit (QIAGEN) using 10 ng of natural DNA as template.

Generation of Mock Forensic Samples.

For generating artificial touch DNA samples, in vitro synthesized DNA was applied directly to the surface of the object and allowed to dry. For generating artificial blood samples, red blood cells were isolated from whole blood by centrifugation (1500 g, 10 min), and mixed with in vitro synthesized DNA. Drops of the red blood cell-DNA mix were dripped from a height of 1 m and allowed to dry. For generating artificial saliva samples, saliva extract (containing no cells) was isolated from the top phase of centrifuged natural saliva (1500 g, 10 min), and mixed with in vitro synthesized DNA. The saliva extract-DNA mix was applied directly to the surface of the object and allowed to dry. A detailed description of all samples is provided in Table 3.

TABLE 2

Descriptions of mock forensic samples

| # | DNA origin | Sample description |
|---|---|---|
| 1 | In vivo | 30 µl drops of blood from donor 'N240', dripped on the floor from a height of 1 m |
| 2 | In vivo | 30 µl drops of blood from donor 'N283', dripped on the floor from a height of 1 m |
| 3 | In vivo | 30 µl drops of blood from donor 'N346', dripped on the floor from a height of 1 m |
| 4 | In vivo | 30 µl drops of blood from donor 'N219', dripped on the floor from a height of 1 m |
| 5 | In vivo | 50 µl saliva from donor 'N270', applied to the inner surface of a ski mask |
| 6 | In vivo | 50 µl saliva of donor 'N283', applied to the inner surface of a ski mask |
| 7 | In vivo | 50 µl saliva of donor 'N229', applied to the inner surface of a ski mask |
| 8 | In vivo | Skin scrapings of donor 'N270' |
| 9 | In vivo | Skin scrapings of donor 'N243' |
| 10 | In vivo | Skin scrapings of donor 'N223' |
| 11 | In vitro | Artificial blood with WGA-synthesized DNA of 'N283' and red blood cells from 'N227': 10 ng of DNA were extracted from a single hair of donor 'N283' and amplified in vitro to ~10 µg by WGA. Red blood cells were isolated from the blood of donor 'N227' by centrifugation. The artificial DNA was mixed with the red blood cells and 30 µl drops of this artificial blood were dripped on the floor from a height of 1 m (FIG. 2C). |
| 12 | In vitro | Artificial blood with WGA-synthesized DNA of 'N226' and red blood cells from 'N227': 10 ng of DNA were extracted from a single hair of donor 'N226' and amplified in vitro to ~10 µg by WGA. Red blood cells were isolated from the blood of donor 'N227' by centrifugation. The artificial DNA was mixed with the red blood cells and 30 µl drops of this artificial blood were dripped on the floor from a height of 1 m |
| 13 | In vitro | Artificial blood with PCR-amplified DNA of 'N222' and red blood cells from 'N283': 1 ng of DNA was extracted from a cigarette butt smoked by donor 'N222' and amplified by PCR at 10 CODIS loci using the Profiler Plus ® kit. Amplified products were combined with a dilution of artificial hTERT fragments generated by PCR amplification of Quantifiler™ standard DNA. Red blood cells were isolated from the blood of donor 'N283' by centrifugation. The artificial DNA was mixed with the red blood cells and 30 µl drops of this artificial blood were dripped on the floor from a height of 1 m |
| 14 | In vitro | Artificial blood with a cloned DNA profile of 'N400' and red blood cells from 'N283': The artificial profile of donor 'N400' was assembled from a library of cloned CODIS and hTERT alleles. Red blood cells were isolated from the blood of donor 'N283' by centrifugation. The artificial DNA was mixed with the red blood cells and 30 µl drops of this artificial blood were dripped on the floor from a height of 1 m |
| 15 | In vitro | Artificial saliva with WGA-synthesized DNA of 'N400' and saliva extract from 'N270': 10 ng of DNA were extracted from a saliva stain on absorbent paper used by donor 'N400', and amplified in vitro to ~10 µg by WGA. Saliva extract containing no cells was isolated from the saliva of donor 'N270' by centrifugation. The artificial DNA was mixed with the saliva extract and 50 µl of this artificial saliva were applied to the inner surface of a ski mask |
| 16 | In vitro | Artificial saliva with PCR-amplified DNA of 'N222' and saliva extract from 'N283': 1 ng of DNA was extracted from a cigarette butt smoked by donor 'N222' and amplified by PCR at 10 CODIS loci using the Profiler Plus ® kit. Amplified products were combined with a dilution of artificial hTERT fragments generated by PCR amplification of Quantifiler™ standard DNA. Saliva extract containing non cells was isolated from the saliva of donor 'N283' by centrifugation. The artificial DNA was mixed with the saliva extract and 50 µl of this artificial saliva were applied to the inner surface of a ski mask |
| 17 | In vitro | Artificial saliva with a cloned DNA profile of 'Male N400' and saliva extract from 'N270': The artificial profile of non-existent 'Male N400' was assembled from a library of cloned CODIS and hTERT alleles. Saliva extract containing no cells was isolated from the saliva of donor 'N270' by centrifugation. The artificial DNA was mixed with the saliva extract and 50 µl of this artificial saliva were applied to the inner surface of a ski mask (FIG. 2B). |
| 18 | In vitro | Artificial touch DNA sample with WGA-synthesized DNA of 'N400': 10 ng of DNA were extracted from a saliva stain on absorbent paper used by donor 'N400' and amplified in vitro to ~10 µg by WGA. 50 µl of diluted WGA products were applied to the external surface of the action of a handgun |
| 19 | In vitro | Artificial touch DNA sample with PCR-amplified DNA of 'N222': 1 ng of DNA was extracted from a cigarette butt smoked by donor 'N222', and amplified by PCR at 10 CODIS loci using the Profiler Plus ® kit. Amplified products were combined with a dilution of artificial hTERT fragments generated by PCR amplification of Quantifiler™ standard DNA. 50 µl of diluted PCR products were applied to the external surface of the action of a handgun (FIG. 2A). |
| 20 | In vitro | Artificial touch DNA sample with a cloned DNA profile of 'N400': The artificial profile of 'N400' was assembled from a library of cloned CODIS and hTERT alleles. 50 µl of diluted cloned fragments were applied to on the external surface of the action of a handgun |
| | Negative control | Empty swab |

Identification and Collection of Mock Forensic Samples.

Stains were identified as human blood using the HEXAGON OBTI kit (BLUESTAR), and as saliva using Phadebas® Amylase test (Phadebas). Samples of blood and touch DNA were collected with a sterile cotton swab, dampened with distilled water. Saliva samples were composed of cut-out portions of the ski-mask fabric.

DNA Extraction and Quantification.

DNA extraction from all samples was performed according to an organic extraction protocol (Sambrook, Molecular Cloning: A Laboratory Manual (2nd ed.), Cold Spring Harbor Laboratory Press, New York, 1989). DNA quantification was performed using the Quantifiler® Human DNA quantification kit (Applied Biosystems). Real-time PCR was performed on a StepOne™ system (Applied Biosystems).

DNA Profiling, Capillary Electrophoresis and Signal Analysis.

STR loci were amplified using the Profiler Plus® (Applied Biosystems) and PowerPlex16 (for preparing the CODIS allele library; Promega) kits using a GeneAmp® PCR System 9700 (Applied Biosystems). Amplification products were run on an ABI 310 Genetic Analyzer (Applied Biosystems) according to the manufacturer's instructions. The resulting electropherograms were analyzed using GeneMapper ID-X analysis software (Applied Biosystems).

Bisulfate Conversion and Methylation Analysis.

Bisulfite conversion was performed with the EpiTect™ kit (Qiagen). Converted DNA was amplified by PCR at the set of loci described in Table 2. In each PCR, 1/10 of the EpiTect™ products was used as template and the reaction was performed as described below. Amplified fragments were purified using the QIAquick PCR purification kit (QIAGEN) and sequenced.

on allele frequencies in the US Caucasian population (Butler et al., Allele frequencies for 15 autosomal STR loci on U.S. Caucasian, African American, and Hispanic populations. *J Forensic Sci* 48 (2003) 908-911). This probability was multiplied by $3.5 \cdot 10^9$ (approximate male population) to yield the approximate probability that there exists a person with the 'male N400' profile (excluding close relatives of 'N400').

Example 2

Profiles of In Vivo- and In Vitro-Synthesized DNA are Indistinguishable

To demonstrate that DNA can be synthesized in vitro such that its profile will be indistinguishable from that of DNA of in vivo origin, we profiled a natural DNA sample and compared it to corresponding profiles from DNA that was synthesized in vitro by three different methods. Natural DNA was extracted from a saliva sample of female donor 'N400' and genotyped using the Profiler Plus® and GeneMapper ID-X (Applied Biosystems); (FIG. 1A). The GeneMapper ID-X software assigns a color-coded bar above each locus, representing the quality of the genotype at that locus. Green bars represent a good quality genotype without anomalies (i.e. no extra peaks, no allelic imbalance, rfu within a predetermined range), while yellow and red bars represent poorer quality genotypes. The entire profile is also assigned a similar color coded score, where green represents a "perfect" score without anomalies in any locus. The profile obtained from the saliva of donor 'N400' was perfect, as expected of high quality DNA.

TABLE 3

Set of loci used for DNA authentication

| Name | Location | Type | Primer sequences (5' -> 3')[a] | SEQ ID NO: | # CpGs |
|---|---|---|---|---|---|
| FGAref | Chr. 4 | Reference | F = TTAAACTCACAAATTAAACTATAACC | 15 | |
| | | | R = GAGTGATTTGTTTGTAATTGTTAGTAA | 16 | |
| NT18 | Chr. 17 | Methylated | F = TGGGAAGGGTTTTAGTATTAAAAG | 17 | 12 |
| | | | R = CTTCAACAAAATCAACATTTTACTAC | 18 | |
| ADD6 | Chr. 2 | Methylated | F = ATGAGGTGATGAGGAAGGGGT | 19 | 11 |
| | | | R = ATTCTCAACCCAAACTCCTTTCA | 20 | |
| MS53 | Chr. 4 | Non-methylated | F = CACCCTTTAAAAATTTTCCTTAAA | 21 | 6 |
| | | | R = ATTGTGAGAAGAGGAAGTTAAAAGT | 22 | |
| SW14 | Chr. 7 | Non-methylated | F = GGTGAGGGAGGAAGGGATAG | 23 | 17 |
| | | | R = TTAATCCCACTTCCAATCCACT | 24 | |

[a]Primers for FGAref are Bisulfite-specific;
other primers will amplify both converted and non-converted DNA

PCR.

All PCRs (except for profiling) were performed in a total volume of 50 µl with 0.2 µM each primer, 0.2 mM each dNTP, 5 U AmpliTaq Gold (Applied Biosystems), and 5 µl 10×PCR Buffer containing 15 mM MgCl$_2$ (Applied Biosystems). Amplification was performed in a GeneAmp® PCR System 9700 (Applied Biosystems). The PCR program used was: 95° C. for 11 min, followed by 35 cycles of 94° C. for 1 min, 59° C. for 1 min, 72° C. for 1 min, and followed by a final extension step of 60° C. for 45 min.

Probability of "Non-Existent" Profile.

The probability that a random unrelated male has the Profiler Plus® profile of 'male-N400' was calculated based Next, we produced three types of in vitro synthesized DNA with the same genotype as 'N400'. For the first sample the 10 Profiler Plus® STRs were amplified in separate PCRs using 1 ng of natural 'N400' DNA (extracted from a cigarette butt smoked by 'N400') as template for each reaction. The PCR products, representing over a billion-fold amplification of the template DNA, were combined, diluted, and profiled (FIG. 1B). The second sample was generated by multiple displacement amplification (MDA), an isothermal WGA method in which nanogram quantities of genomic DNA are amplified overnight to microgram quantities, and the amplified products contain a representation of the entire genome (Dean et al., Comprehensive human genome amplification using multiple displacement amplification. *Proc Natl Acad Sci USA* 99 (2002) 5261-5266). Ten nanograms of natural 'N400' DNA (obtained from a saliva stain on absorbent paper used by 'N400') were used as template for MDA, and a dilution of the products was used for profiling (FIG. 1C). For the third sample, a "CODIS allele library" was constructed, consisting of individual alleles of CODIS STRs cloned into plasmids. In the library each element is a microcentrifuge tube with trillions of copies of a single allele (for example, one element is allele 11 of locus D8S1179, while another is allele 12 of D8S1179, and likewise for the other CODIS loci). The alleles in the CODIS library originated from PCR amplification of commercial pooled human DNA (which contains multiple alleles at each locus), and none of them originated from the DNA of 'N400'. For assembling the third sample, equal quantities of alleles corresponding to the alleles of 'N400' were picked from the library, combined in a single tube, diluted, and profiled (FIG. 1D). In contrast to the first two methods (PCR and WGA) which required at least a minute amount of natural 'N400' DNA as template, for construction of the cloned profile of 'N400' no such template DNA was required (only a priori knowledge of her profile was required). Furthermore, a similar library containing 425 clones corresponding to all known CODIS alleles (including all rare micro-variants) is sufficient to generate any desired profile, while a much smaller library is sufficient to generate the profiles of the vast majority of the human population. In order to demonstrate the possibility to create any desired profile, we used the library to assemble a profile of a non-existent person, which we term 'male N400'. This profile is identical to that of 'N400', with the exception of the Amelogenin locus, in which its genotype is XY instead of XX (FIG. 1E). We calculated that the probability that a male unrelated to 'N400' has a profile identical to that of 'male N400' is $7.95 \cdot 10^{-12}$, and consequently the probability that there does not exist in the world population an unrelated male with an identical profile is greater than 99.99%.

The genotypes of all in vitro synthesized 'N400' samples were identical to the genotype obtained from the natural 'N400' DNA, and all profiles were perfect according to GeneMapper ID-X analysis.

Example 3

The Current Forensic Procedure Fails to Distinguish Between Natural and Artificial DNA Evidence Generation of Artificial DNA Evidence.

Figures 1, 2A:
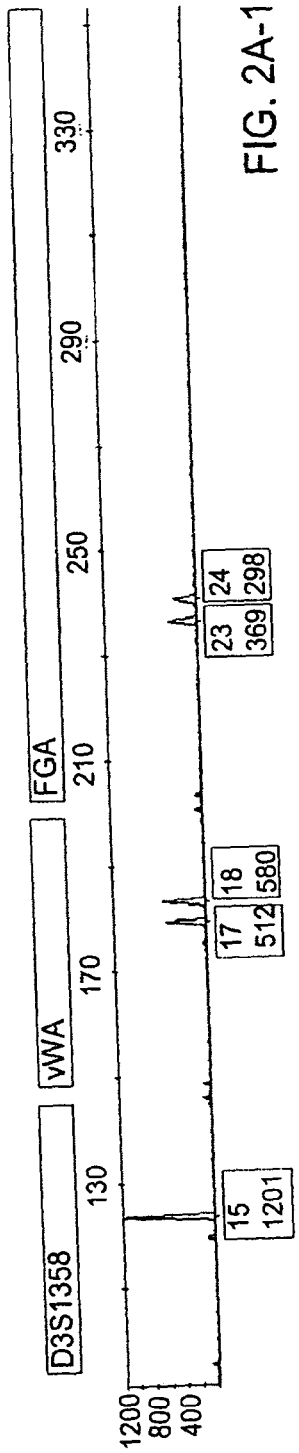
Figures 2, 2A:
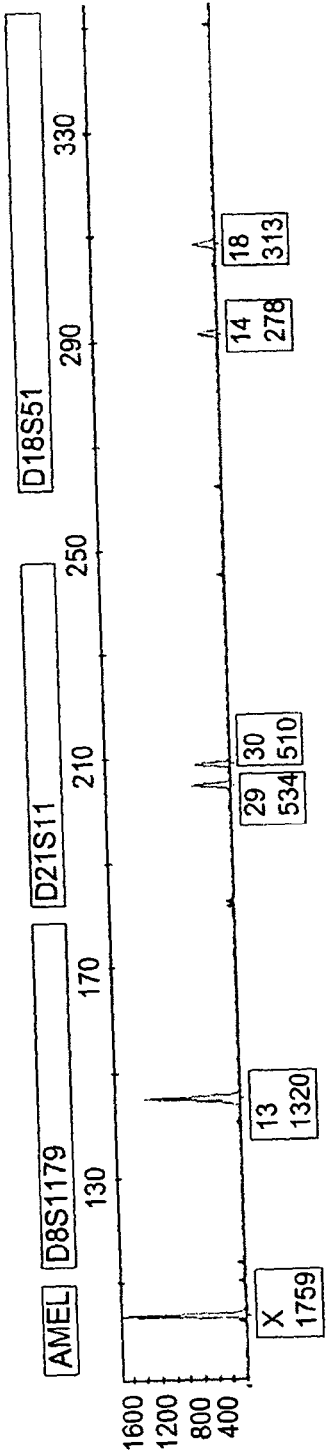
Figures 2, 2A, 3:
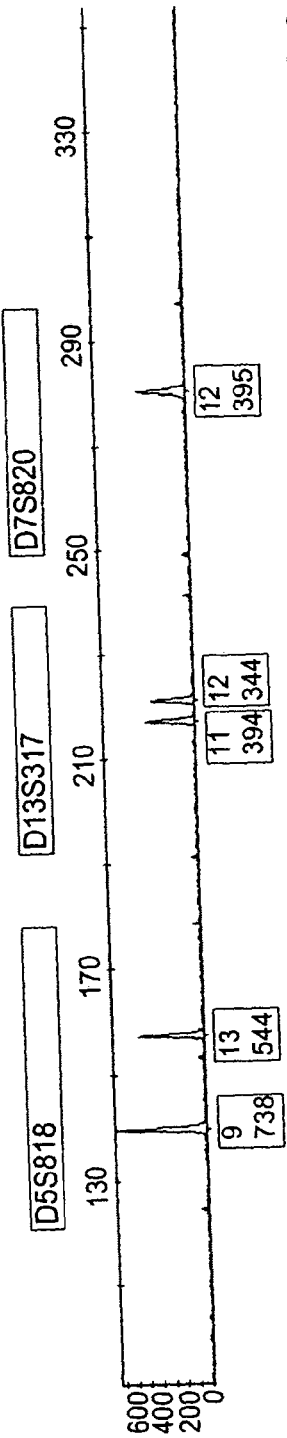
Figures 1, 2B:
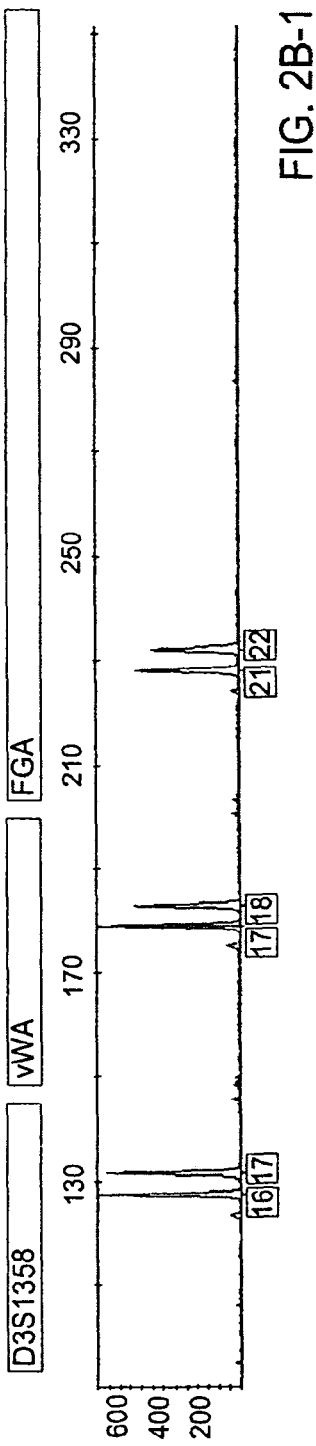
Figures 2, 2B:
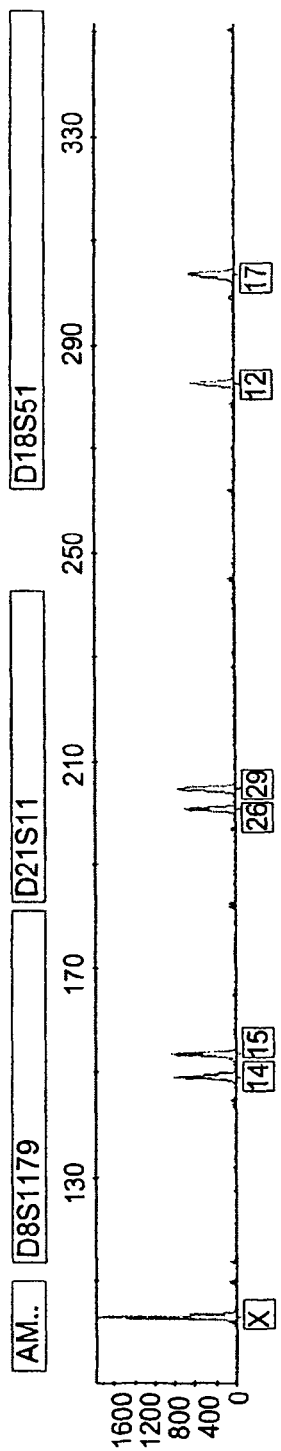
Figures 2, 2B, 3:
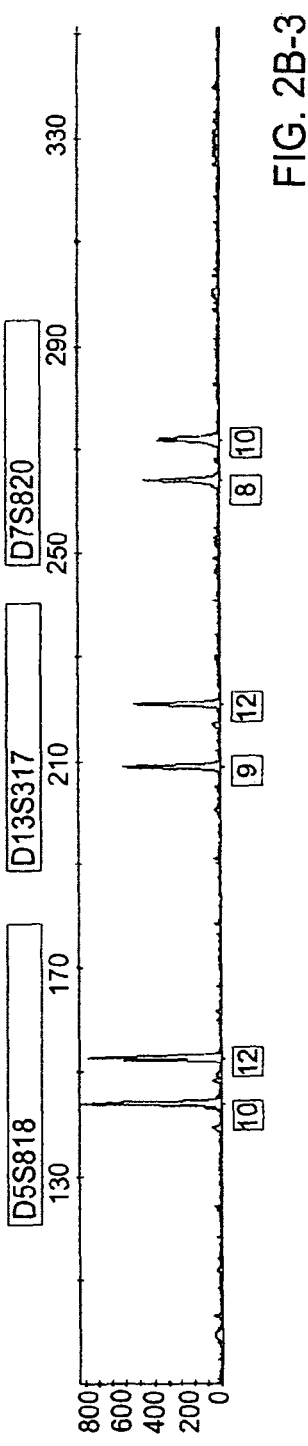
Figure 3:
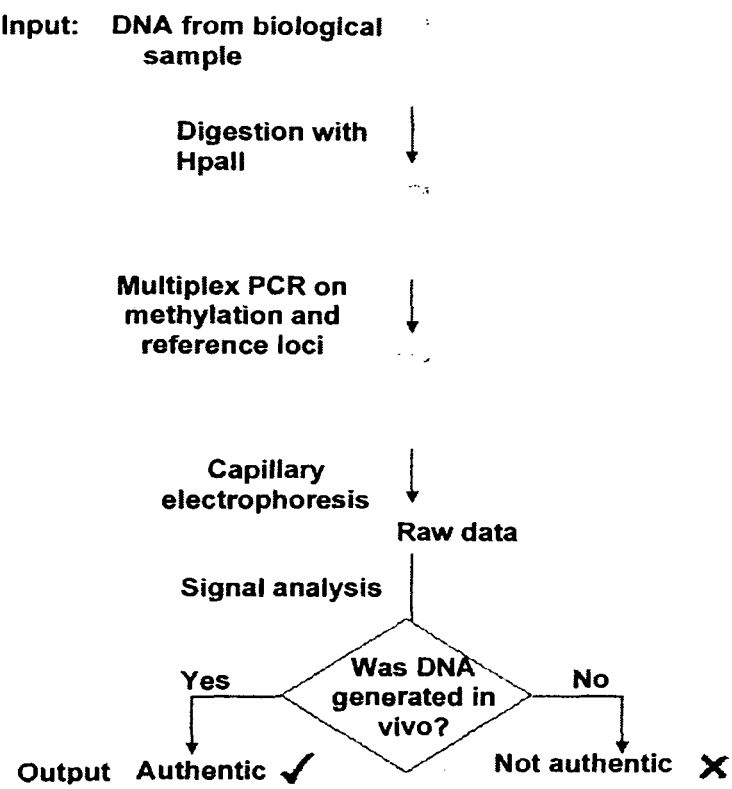
FIG. 3 demonstrates a specific implementation of the DNA authentication procedure, based on analysis of methylation of HpaII digested DNA.

We created 10 mock forensic samples with artificial DNA, of types that may be found in crime scenes, and subjected three of these samples to analysis through the complete forensic procedure (the rest of the samples are discussed in section 3.4). These three samples contained artificial DNA that was synthesized using different methods: a handgun sample with PCR amplified DNA, a ski-mask with DNA fragments from the cloned allele library, and bloodstains with DNA synthesized by WGA (FIG. 2A-C). The handgun sample was created by applying artificial DNA of female donor 'N222' to the external surface of the action. The artificial DNA contained a mix of PCR amplified CODIS and hTERT (the target of the Quantifiler™ kit that is often used for forensic DNA quantification) fragments. For generation of the CODIS fragments, 1 ng of natural DNA was extracted from a cigarette butt smoked by 'N222', amplified at 10 CODIS loci by a single PCR reaction using the Profiler Plus® kit, and the products were diluted. The hTERT fragment was obtained by diluting a Quantifiler™ PCR reaction in which the standard DNA of the kit was used as template (the hTERT locus, as opposed to CODIS loci, is not polymorphic and therefore any human DNA can be used as template). The resulting combination of 11 amplified fragments (10 CODIS and hTERT) is not a full representation of the DNA of 'N222', but rather includes a very small fraction (less than 0.01%) of the genome. Nevertheless, this small fraction is sufficient for "passing" forensic DNA quantification and profiling, as natural DNA, since the forensic procedure is based on analysis of this small set of loci.

The artificial DNA for the ski-mask sample (FIG. 2B) was created by combining a cloned profile of 'male N400' (assembled from the CODIS allele library, as described above), and a cloned hTERT fragment. In order to create an artificial saliva sample, natural saliva from donor 'N270' was centrifuged, and the supernatant, containing the amylase enzyme (which is the target of the Phadebas® assay—see below) but without cells, was mixed with a dilution of the artificial cloned DNA. This mixture was applied to the inner surface of the ski-mask fabric, around the mouth orifice.

The artificial DNA for the bloodstain sample (FIG. 2C) was created by WGA: 10 ng of natural DNA of male donor 'N283' that were extracted from a single hair were used as template for a WGA reaction using the Repli-g Midi kit, yielding 10 µg amplified artificial DNA. In contrast to the handgun and ski-mask samples, the artificial DNA in this sample contained a representation of the entire genome of 'N283', and not only CODIS loci. In order to create an artificial blood sample, the natural blood of female donor 'N227' was centrifuged and the red blood cell fraction (containing no nuclei) was isolated and mixed with a dilution of the artificial WGA DNA. Drops of this artificial blood were dripped from a height of 1 meter onto the floor and allowed to dry.

Analysis of Artificial DNA Evidence.

The three samples were processed according to the routine forensic procedure performed in crime scenes. Samples were collected from the external surface of the handgun action (with a sterile swab, dampened by distilled water), from the ski-mask fabric (a portion of the wool around the mouth orifice), and from the bloodstains (with a sterile swab dampened by distilled water). A portion of the ski-mask sample was tested for presence of saliva using the Phadebas® assay, and the results were positive (data not shown), due to the presence of amylase in the supernatant of the natural saliva extract. A portion of the bloodstain sample was tested for the presence of human blood DNA using the HEXAGON OBTI assay, and the results were positive (data not shown), due to the presence of hemoglobin in the red blood cells. DNA was extracted from all three samples by organic extraction, and quantification was performed with the Quantifiler™ kit. One nanogram of DNA from each sample was used for genotyping with Profiler Plus®. The capillary electropherograms were analyzed with GeneMapper ID-X, and the resulting profiles are depicted in FIG. 2D (partial profiles). The genotypes of all three samples were identical to the genotypes of the artificial DNA that was used in their production. Furthermore, in the artificial saliva and blood samples there were no observable traces of natural DNA from the saliva and blood donors (whose partial profiles are shown in FIGS. 2E and 2F, respectively), and all artificial profiles received a perfect GeneMapper ID-X score, consistent with a single contributor.

Independent Analysis of Artificial Blood Evidence.

In order to check whether the profiling results obtained in our laboratory were dependant on our specific setup, we sent a duplicate swab of the artificial blood sample to a leading forensic DNA laboratory for analysis. The procedures employed by this laboratory have been validated according to standards established by the Scientific Working Group on DNA Analysis Methods (SWGDAM) and adopted as US Federal Standards. DNA was extracted from the sample in the laboratory using the EZ1 DNA Investigator Kit (QIAGEN), and quantified using a proprietary real time PCR assay (both extraction and quantification methods were different than those employed in our lab). Genotyping was performed with Profiler Plus® and COfiler® (Applied Biosystems). The report received from the laboratory states that "The DNA profile obtained from sample 2S09-002-001 [the artificial blood swab] is consistent with a male contributor", and the profiling results, both in Profiler Plus® and COfiler® were identical to the genotype of the artificial DNA of donor 'N283', with "No Edits" (i.e. no anomalies found in any of the analyzed loci; see report in Text S3).

These results demonstrate that artificial DNA can easily be applied to surfaces of objects or incorporated into genuine human tissues, thereby creating artificial forensic evidence that, after undergoing the entire forensic casework procedure, yields perfect profiles.

Example 4

DNA Authentication Assay

Authenticating the in vivo source of forensic DNA samples requires a method that is able to distinguish between in vitro synthesized and in vivo generated DNA. Distinguishing between the two types of DNA is possible because all current methods for in vitro synthesis/amplification of DNA generate products that are different than in vivo generated DNA in their composition and/or chemical properties. However, since there are many different methods for in vitro synthesis/amplification of DNA, and since each method generates different types of products, finding a single method which can differentiate between the two types of DNA can be challenging.

A simple approach for this purpose could have been establishing the extent of genomic coverage in the DNA sample, or more specifically, determining the existence or absence of non-CODIS loci. Artificial DNA samples that are synthesized by PCR or molecular cloning generally contain only a small set of loci (CODIS alleles and perhaps the hTERT locus or similar targets for DNA quantification), and do not contain other non-CODIS loci, which represent the vast majority of the genome. PCR amplification of non-CODIS loci will therefore fail in such samples and this simple approach can be useful for exposing artificial DNA that was synthesized by such methods. However, such an approach cannot differentiate between natural DNA and artificial DNA that was synthesized by WGA, since such DNA contains a representation of all genomic loci, similarly to natural DNA. Therefore this approach alone cannot differentiate between natural and all types of artificial DNA.

We developed a DNA authentication assay that differentiates between natural and all types of artificial DNA based on analysis of methylation patterns. Methylation is an epigenetic chemical modification of DNA, occurring in mammals in the form of a methyl group ($—CH_3$) that is enzymatically added to the C5 position of cytosine in some CpG dinucleotides (Mirand and Jones. DNA methylation: the nuts and bolts of repression. *J Cell Physiol.* 213 (2007) 384-390). DNA methylation is believed to inhibit gene expression in animal cells, probably by affecting chromatin structure (Hashimshony et al., The role of DNA methylation in setting up chromatin structure during development. *Nat. Genet.* 34 (2003) 187-192). In the human genome 70-80% of all CpGs are methylated, while unmethylated CpGs are grouped in clusters called "CpG islands" (Bird, DNA methylation patterns and epigenetic memory. *Genes Dev.* 16 (2002) 6-21). The authentication assay is based on the fact that unlike in vitro synthesized DNA which is completely unmethylated, in vivo generated DNA contains loci that are completely and consistently methylated and other loci that are completely and consistently unmethylated.

In one embodiment of the assay, DNA from a forensic sample in question is treated with sodium bisulfite, which converts all unmethylated cytosines to uracils, while leaving the methylated cytosines unaffected (Frommer et al., A genomic sequencing protocol that yields a positive display of 5-methylcytosine residues in individual DNA strands. *Proc Natl Acad Sci USA* 89 (1992) 1827-1831) (in subsequent PCR, uracils are amplified as if they are thymines, resulting in conversion of the sequence "CG" to "TG" in unmethylated but not in methylated CpG dinucleotides). Following bisulfite conversion, the DNA is amplified by PCR at a set of loci, containing one reference CODIS locus (FGAref), and four non-CODIS loci (NT18, ADD6, MS53, SW14). These loci were chosen because NT18 and ADD6 are consistently methylated, while MS53 and SW14 are consistently unmethylated in human tissues such as blood, saliva and epidermis (the source of touch DNA). The primers for amplification of this set of loci were designed to enable detection of incomplete bisulfite conversion (a major concern in this type of assay) by being completely devoid of cytosines (or guanines, depending on whether the sense or antisense strands are to be amplified). Such primers amplify with equal efficiency both converted and unconverted DNA, thus facilitating detection of incomplete conversion of the DNA upon sequencing. Following PCR, the presence or absence of amplicons is determined. This can be achieved by electrophoresis of PCR products, or alternatively, by real time PCR. Complete absence of amplicons (including FGAref) indicates a problem in the procedure due to PCR inhibitors, insufficient template, etc. Successful amplification of the CODIS reference locus (FGAref) with concomitant failure of amplification of the non-CODIS loci indicate that the DNA is artificial and was synthesized by one of the methods that generate only a subset of genomic loci (e.g. PCR or cloning of CODIS loci). Successful amplification of all loci indicates that the DNA contains a full representation of the genome and is either natural DNA or artificial DNA synthesized by WGA. Differentiation between these two types of DNA is achieved by sequencing the four non-CODIS amplicons and analysis of their methylation pattern. The DNA is determined to be of in vivo origin if its methylation pattern is consistent with that of in vivo generated DNA (i.e. complete methylation of all CpGs in NT18 and ADD6 alongside with complete non-methylation of all CpGs in MS53 and SW14), otherwise it is determined to be of in vitro origin.

Demonstration of the DNA Authentication Assay.

We applied the DNA authentication assay to 20 mock forensic samples, 10 with natural DNA, 10 with artificial DNA, and a negative control sample without DNA (Table 1). Following DNA extraction, all samples were treated with sodium bisulfite and amplified at the four non-CODIS loci and the FGAref locus (FIG. 3). All samples with natural DNA showed successful amplification of all loci, and the FGAref amplicon was present in all samples, both natural and artificial (but not in the negative control sample). Samples 13, 14, 16, 17, 19, 20 which contain artificial DNA synthesized by PCR or molecular cloning, failed to amplify the four non-CODIS loci, since the DNA in these samples contains only CODIS loci. These samples were therefore determined to be non-authentic and were not processed further. The remaining artificial DNA samples (11, 12, 15, 18) contained WGA-synthesized DNA and in these sample all loci amplified successfully, similar to natural DNA.

Figure 4A:
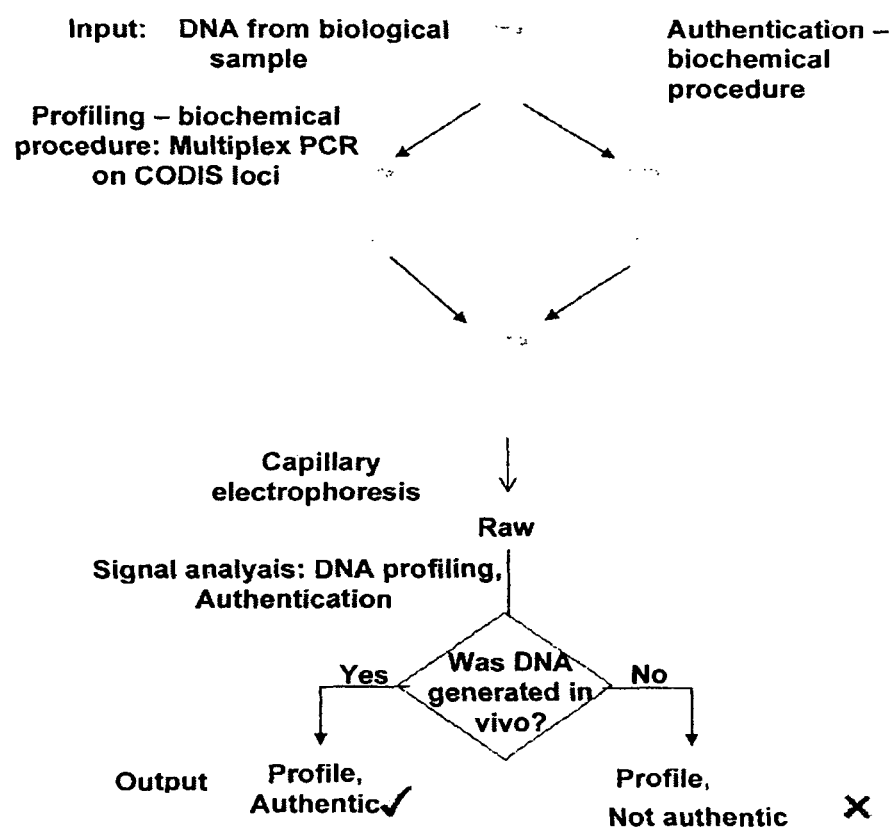
FIG. 4A demonstrates a joint DNA profiling and authentication scheme.
Figure 4B:
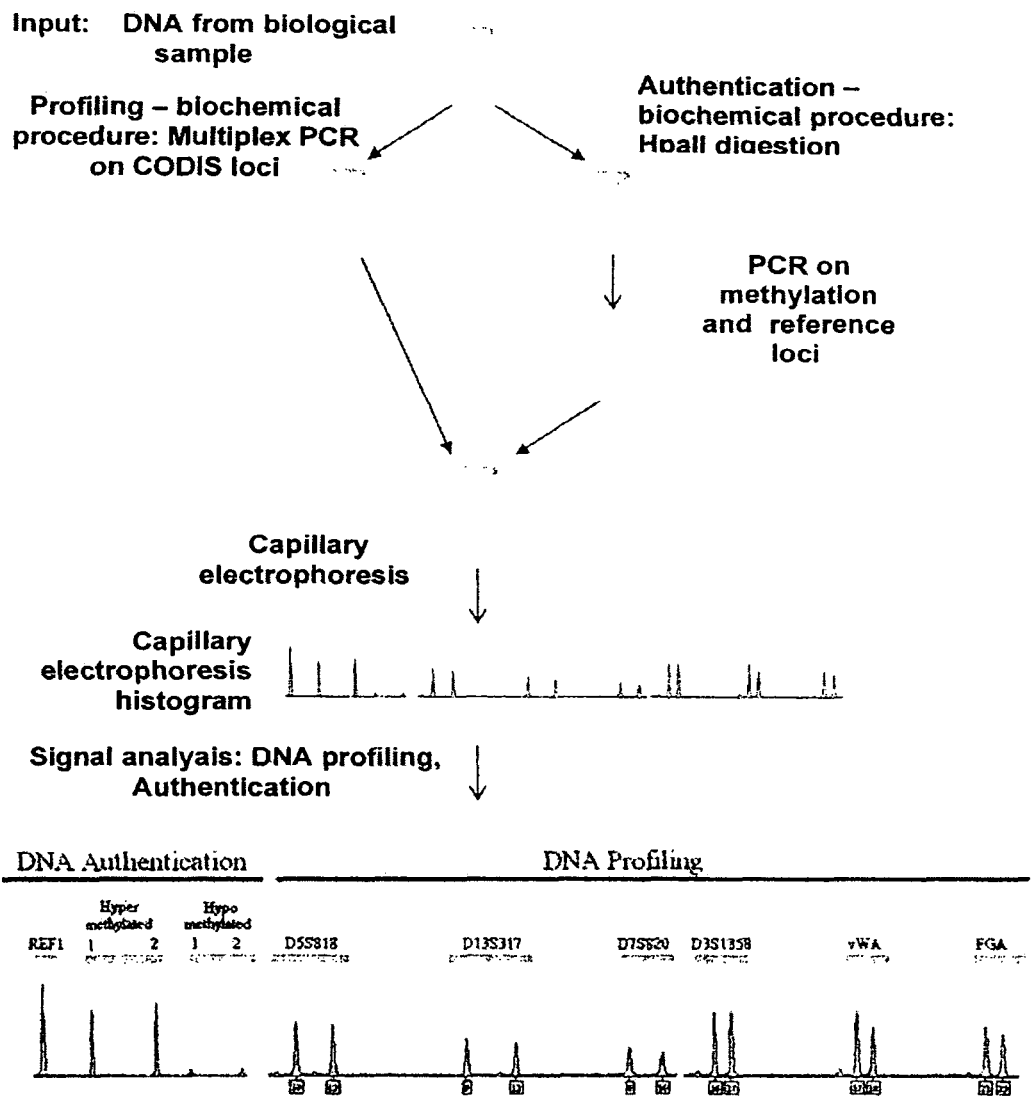
FIG. 4B depicts a scheme of a joint DNA profiling and authentication procedure employing an HpaII based methylation assay. The left portion of the output histogram contains authentication loci and the right portion of the output histogram contains profiling loci. Color-coded bars are depicted above each analyzed locus. Bars in the authentication region represent results that indicate that the DNA sample was generated in vivo.
Figures 5A, 5B:
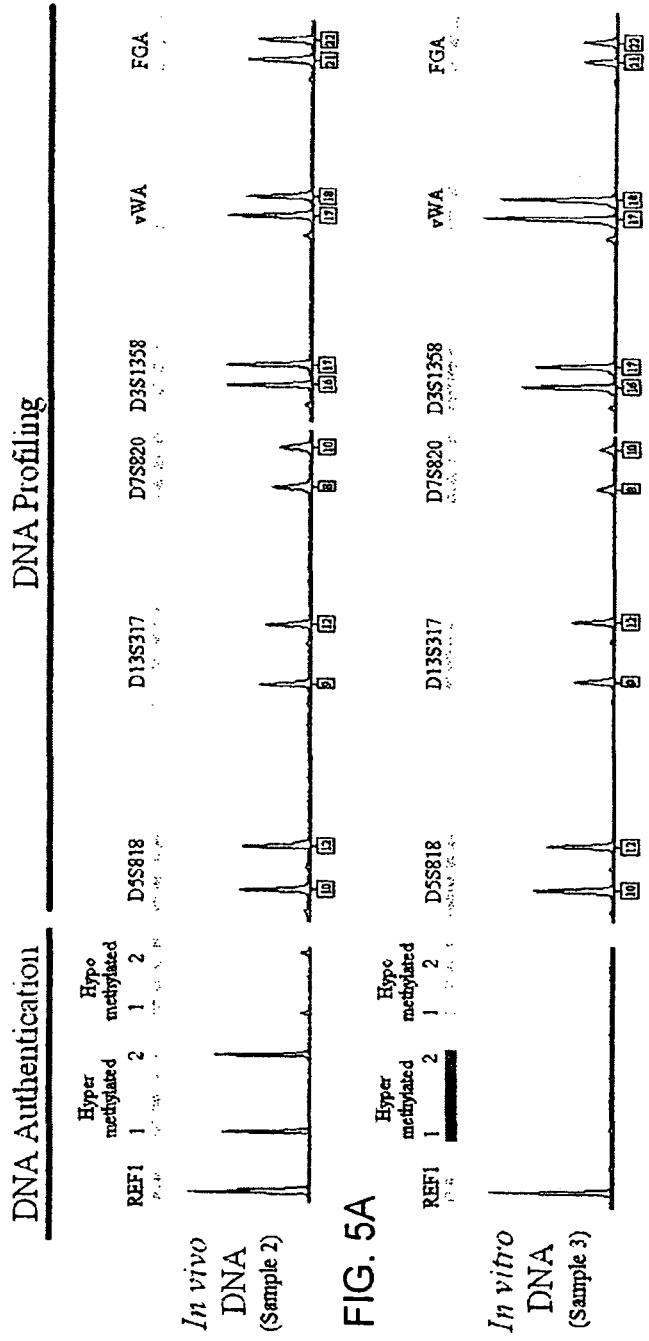
FIGS. 5A and 5B depict examples of DNA profiles combined with results of DNA authentication for the capillary electrophoresis histograms of samples 2 and 3. 5A represents in vivo generated DNA and 5B represents in vitro generated DNA.
Figure 6A:
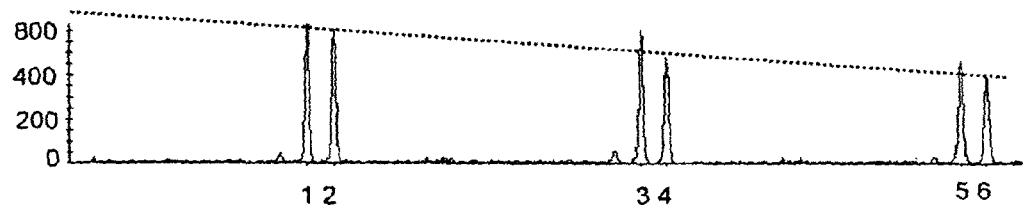
FIG. 6A-D demonstrates the calculation of the representation bias based on a linear regression of capillary electrophoresis histogram peaks. 6A and 6B represent in vivo generated DNA, and 6C, 6D represents in vitro generated DNA.
Figure 6B:
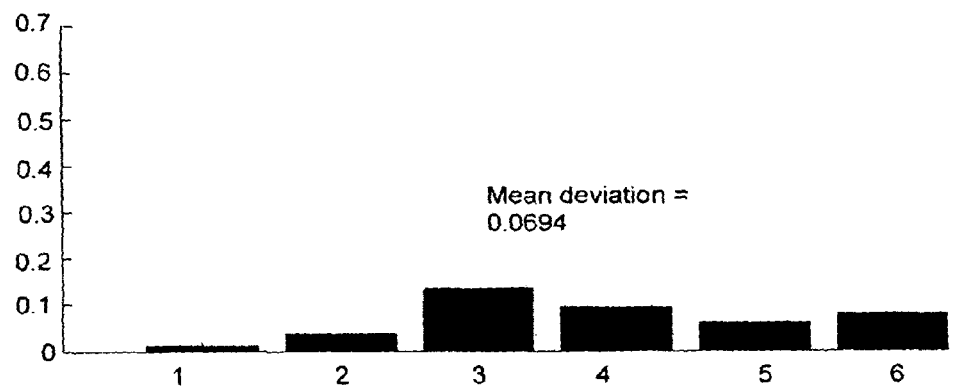
Figure 6C:
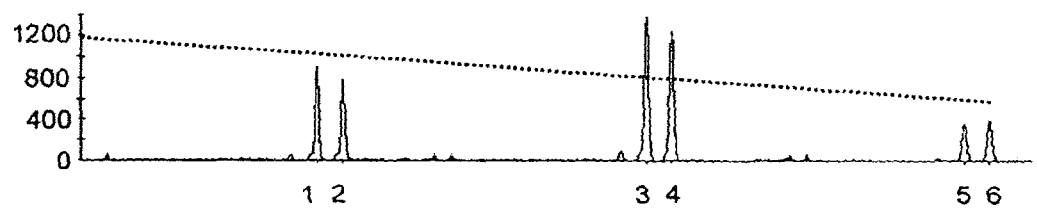
Figure 6D:
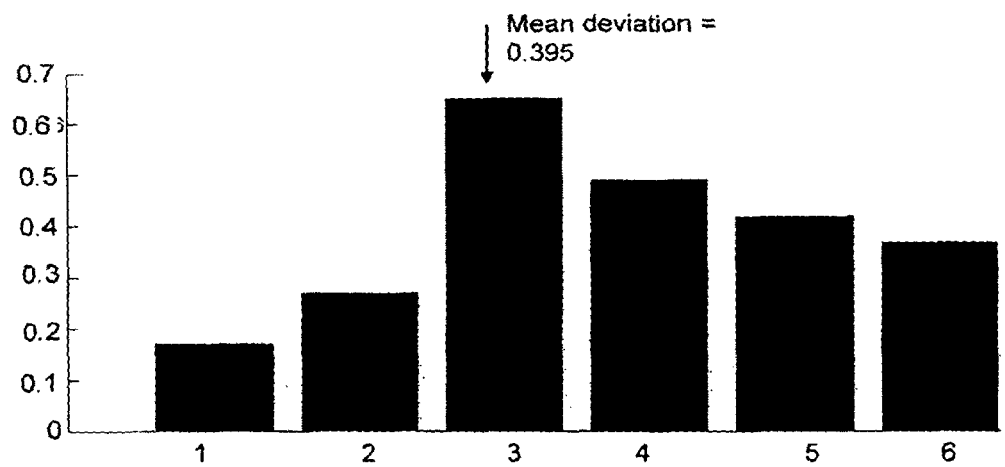
Figure 7:
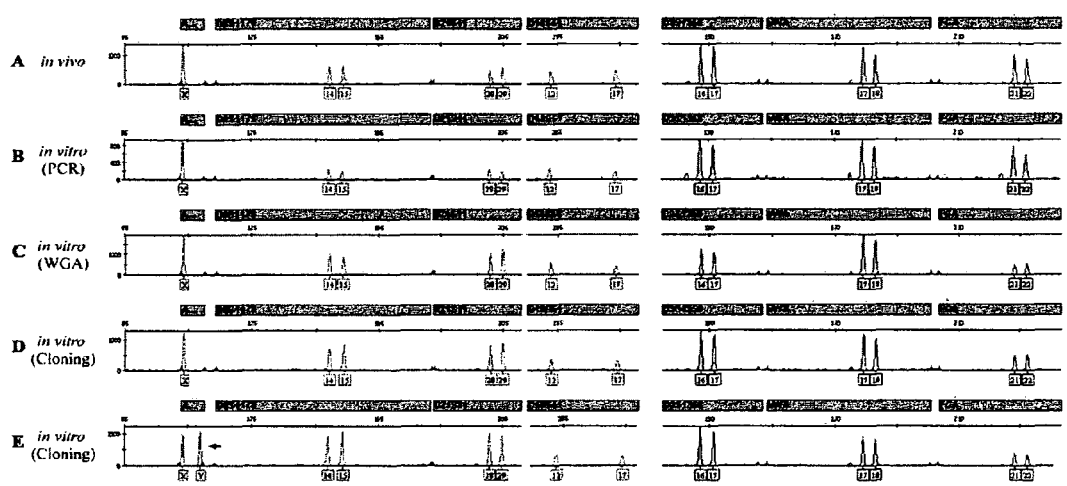
FIG. 7 shows profiles of in vivo- and in vitro-synthesized DNA. A. Profile of natural DNA obtained from the saliva of female donor 'N400'. B-D. Profiles identical to that of 'N400' obtained from DNA that was synthesized in vitro by three different methods: PCR (B), WGA (C), and assembly from a library of cloned CODIS alleles (D). E. Profile identical to that of 'male-N400', which is identical to the profile of 'N400' at all loci, except for the Amelogenin locus. This profile was created by adding a cloned Y allele (indicated by arrow) to the mix used to generate the profile in (D).
Figure 8:
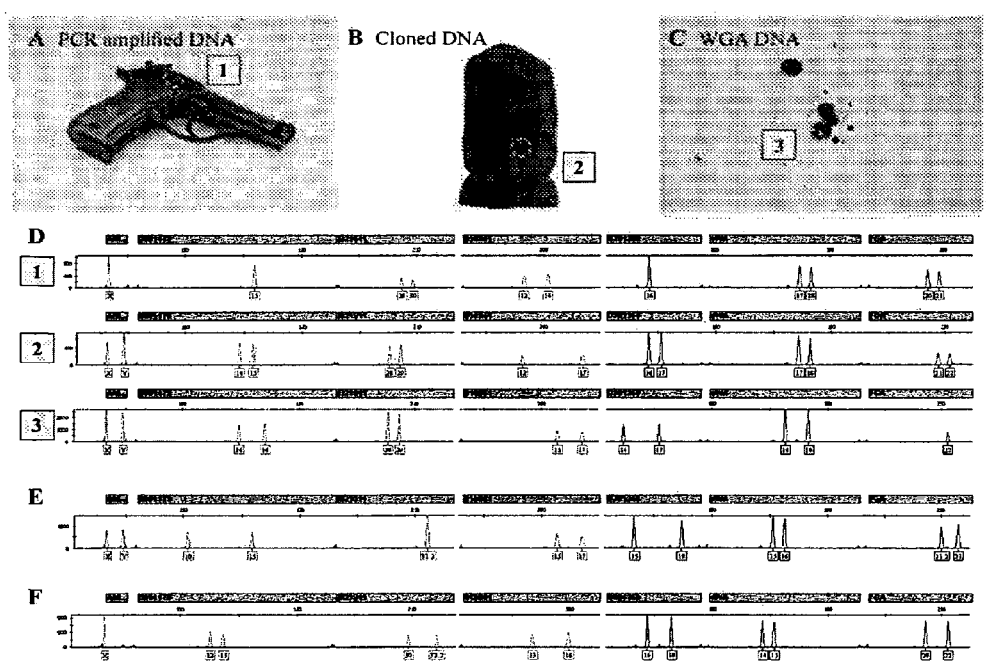
FIG. 8 shows mock forensic samples with artificial DNA. A. Handgun with PCR amplified DNA with the profile of N222 applied to the external surface of its action. B. Ski-mask with artificial saliva applied to its inner surface. The artificial saliva contained an extract of natural saliva from N270 (without DNA) and DNA fragments with the profile of 'male N400' assembled from the cloned CODIS allele library. C. Artificial bloodstains containing red blood cells from natural blood of N227 and artificial 'N283' DNA generated by WGA. In A-C, yellow circles depict the areas from which samples were taken for analysis. D. Profiles of the three artificial samples. All three profiles received a "perfect" GeneMapper ID-X score, and are identical to the genotypes of the artificial DNA that was used in their production. No traces of DNA from the saliva extract and red blood cells are visible in the profiles from the ski-mask and bloodstains (see E and F). E. Profile of donor N270, whose saliva extract was used in manufacturing the ski-mask sample. F. Profile of donor N227, whose red blood cells were used in manufacturing the bloodstain.
Figure 9:
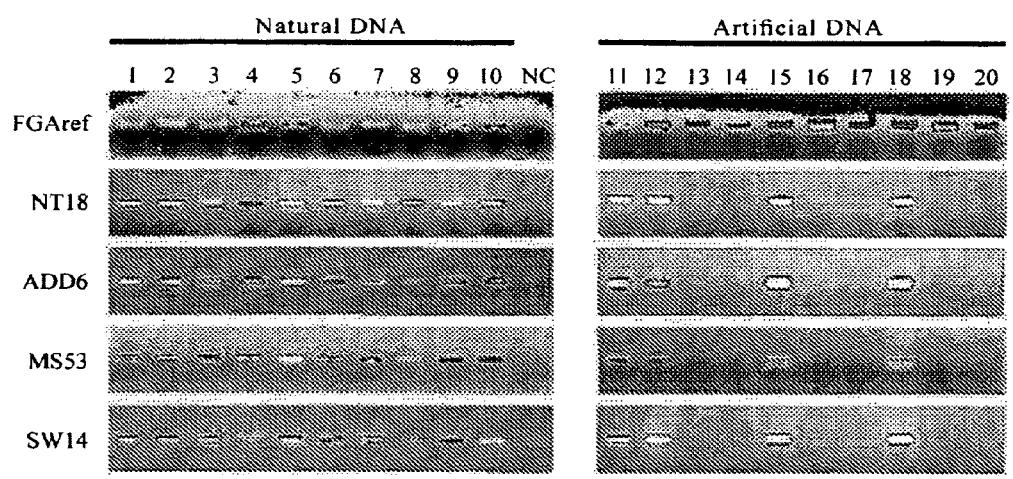
FIG. 9 shows amplification products in natural and artificial mock forensic samples. Aliquots of PCR products were run on a 2% Agarose gel. The FGAref locus is amplified in all samples (both natural and artificial), but not in the negative control sample. Non-CODIS loci are amplified in all natural (1-10) and in WGA-based artificial samples (11, 12, 15, 18), but are absent in PCR- and cloning-based artificial samples (13, 14, 16, 17, 20).
Figure 10:
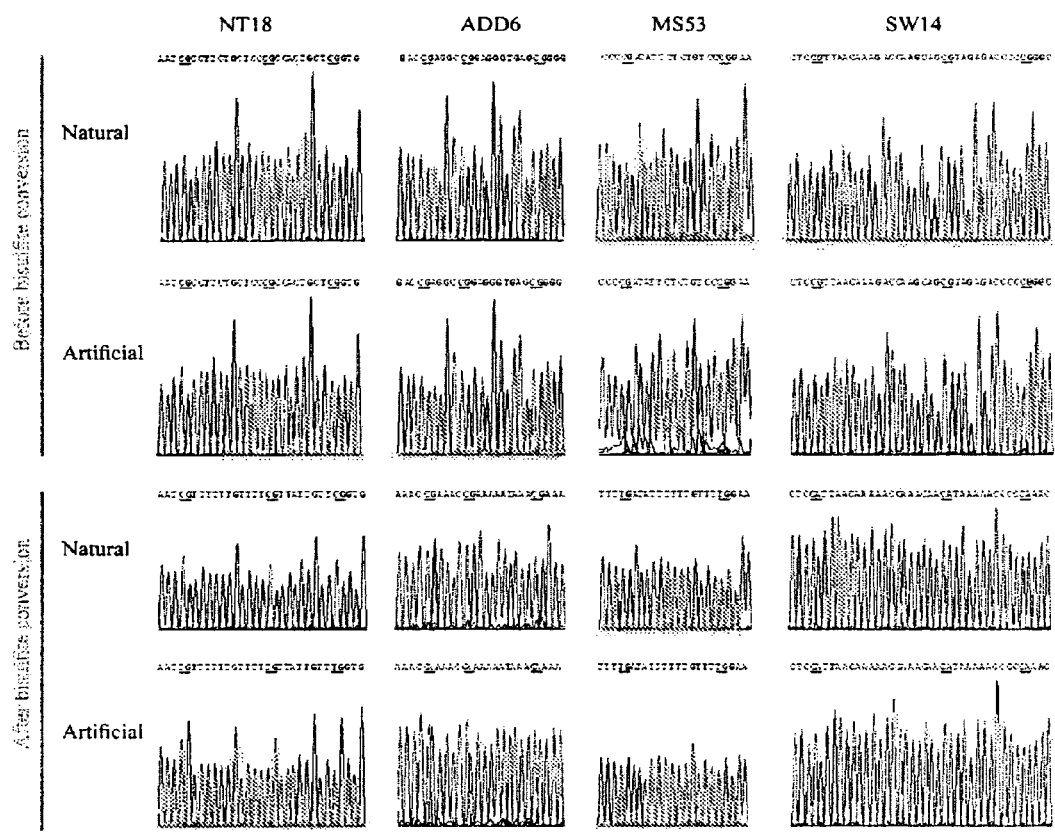
FIG. 10 shows the results of a methylation analysis of natural (SEQ ID NOS 51-54 and 59-62, respectively, in order of appearance) and artificial samples (SEQ ID NOS 55-58 and 63-66, respectively, in order of appearance). Partial sequences of DNA from natural and artificial blood samples (samples 2 and 11, respectively) at non-CODIS loci (CpG dinucleotides are underlined). The sequences of unconverted DNA are identical at all loci, demonstrating that natural and artificial samples cannot be distinguished on the basis of sequence alone. Following bisulfite conversion, the differential methylation pattern of natural vs. artificial DNA is exposed: natural DNA is methylated at NT18 and ADD6, and unmethylated at MS53 and SW14, while artificial DNA is unmethylated at all four loci.
Figure 11:
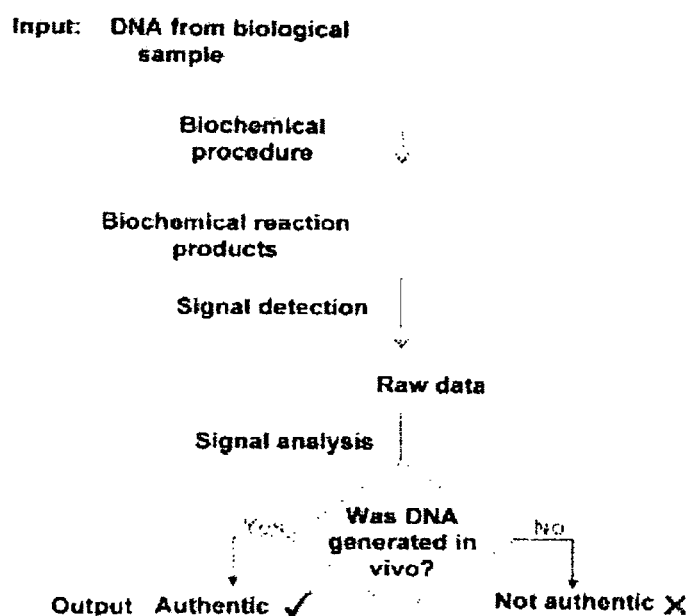
FIG. 11 is a schematic flow-chart of one series of embodiments for determining the presence of artificial DNA in a sample.

The natural and WGA-synthesized DNA samples were processed further by sequencing at the four non-CODIS loci and analysis of the methylation status at all CpG positions (Table 3). All natural DNA samples showed complete methylation of all 12 CpG positions in NT18, complete methylation of all 11 CpG positions in ADD6, no methylation in any of the 6 CpG positions in MS53, and no methylation in any of the 17 CpG positions in SW14. In contrast, all WGA-synthesized samples showed no methylation in any of the CpG positions of NT18, ADD6, MS53, and SW14, reflecting the complete lack of methylation in these samples (FIG. 4 shows partial sequences in a natural and an artificial sample). Based on this methylation analysis, the 10 natural samples were determined to be authentic, and the four WGA-synthesized samples were determined to be non-authentic. Therefore the assay was successful in determining the correct status of all 20 samples (Table 3).

source DNA, only requiring knowledge of the 26 numbers that make up the desired profile.

Once source DNA from a person or knowledge of his/her profile is obtained, the actual manufacturing of the artificial sample is simple and straightforward. Generating large amounts of artificial DNA can be performed overnight, using basic laboratory equipment and commercial kits, requires only basic knowledge in molecular biology, and little financial expense. There is a very large and growing number of people with the necessary expertise and access to the required equipment, such as scientists, research students, lab technicians in hospitals, pharmaceutical or biotech companies, etc. Moreover, since commercial molecular biology services are becoming widespread and DNA with any sequence can be ordered online, manufacturing an artificial DNA sample does not require much more than a personal computer and link to the internet.

Authentication is Necessary for Preventing False DNA Matches.

The DNA profiles of millions of people are registered in rapidly growing national databases, and the current trend around the world is to include more and more profiles in

TABLE 4

DNA authentication results on natural and artificial mock forensic samples

| | Sample | FGAref | Methylated CpG positions [a] | | | | |
|---|---|---|---|---|---|---|---|
| # | Source of DNA | amplified | NT18 | ADD6 | MS53 | SW14 | Decision |
| 1 | In vivo (blood) | Yes | 12/12 | 11/11 | 0/6 | 0/17 | Authentic |
| 2 | In vivo (blood) | Yes | 12/12 | 11/11 | 0/6 | 0/17 | Authentic |
| 3 | In vivo (blood) | Yes | 12/12 | 11/11 | 0/6 | 0/17 | Authentic |
| 4 | In vivo (blood) | Yes | 12/12 | 11/11 | 0/6 | 0/17 | Authentic |
| 5 | In vivo (saliva) | Yes | 12/12 | 11/11 | 0/6 | 0/17 | Authentic |
| 6 | In vivo (saliva) | Yes | 12/12 | 11/11 | 0/6 | 0/17 | Authentic |
| 7 | In vivo (saliva) | Yes | 12/12 | 11/11 | 0/6 | 0/17 | Authentic |
| 8 | In vivo (skin) | Yes | 12/12 | 11/11 | 0/6 | 0/17 | Authentic |
| 9 | In vivo (skin) | Yes | 12/12 | 11/11 | 0/6 | 0/17 | Authentic |
| 10 | In vivo (skin) | Yes | 12/12 | 11/11 | 0/6 | 0/17 | Authentic |
| 11 | In vitro (WGA) | Yes | 0/12 | 0/11 | 0/6 | 0/17 | Non-authentic |
| 12 | In vitro (WGA) | Yes | 0/12 | 0/11 | 0/6 | 0/17 | Non-authentic |
| 13 | In vitro (PCR) | Yes | No amp. | No amp. | No amp. | No amp. | Non-authentic |
| 14 | In vitro (Cloning) | Yes | No amp. | No amp. | No amp. | No amp. | Non-authentic |
| 15 | In vitro (WGA) | Yes | 0/12 | 0/11 | 0/6 | 0/17 | Non-authentic |
| 16 | In vitro (PCR) | Yes | No amp. | No amp. | No amp. | No amp. | Non-authentic |
| 17 | In vitro (Cloning) | Yes | No amp. | No amp. | No amp. | No amp. | Non-authentic |
| 18 | In vitro (WGA) | Yes | 0/12 | 0/11 | 0/6 | 0/17 | Non-authentic |
| 19 | In vitro (PCR) | Yes | No amp. | No amp. | No amp. | No amp. | Non-authentic |
| 20 | In vitro (Cloning) | Yes | No amp. | No amp. | No amp. | No amp. | Non-authentic |
| 21 | Negative Control | No | No amp. | No amp. | No amp. | No amp. | No decision [b] |

[a] Number of methylated CpG positions out of total number of CpG positions in each locus. No amp. = No amplicon observed; Bold indicates results inconsistent with DNA of in vivo origin.
[b] "No decision" is outputted when there is no amplification in any of the loci. Possible reasons may be insufficient/degraded template DNA, PCR inhibitors, etc.

These results demonstrate the ease at which artificial DNA evidence can be produced, and that such evidence "passes" the current forensic procedure as genuine. The fact that an independent forensic laboratory, which provides services to United States law enforcement agencies, analyzed our artificial blood sample yielding a perfectly normal, single contributor DNA profile—attests to the problem.

In this case the artificial DNA was designed to have the profile of donor 'N283', and was amplified from a minute amount of DNA extracted from a single hair of 'N283'. Similarly, we produced artificial samples of DNA amplified from a cigarette butt and a dry saliva stain on absorbent paper. Such common everyday objects, which can be used to obtain source DNA for producing artificial samples, can be obtained from practically anyone. Even this constraint is removed when considering the possibility to produce artificial evidence using the "cloned CODIS allele library", since any profile can be assembled without the need for them, not only of convicted offenders, but also of arrestees. Profiles from casework samples are routinely searched against these databases (e.g. by automatic software such as CODIS), and when an identical profile is found, a DNA "match" is made, making the identified person a suspect in the case and usually leading to his arrest (Bond and Hammond, The value of DNA material recovered from crime scenes. *J Forensic Sci.* 53 (2008) 797-80). The suspect is then expected to explain how his/her DNA was found at the crime scene, and failure to provide a satisfactory explanation will lead to indictment. The weight of such DNA evidence in the courtroom today is very strong, and is considered key to the conviction and exoneration of suspects (Jobling and Gill, Encoded evidence: DNA in forensic analysis, *Nat. Rev. Genet.* 5 (2004) 739-51). In some jurisdictions, DNA evidence alone can lead to conviction without the requirement of any corroborating evidence (Levitt, Forensic databases: benefits and ethical and social costs. *Br. Med. Bull.* 83 (2007)

235-248). However, even when supporting evidence is required by law, there is little doubt that the presence of DNA evidence from a crime scene against a defendant places him/her at a dire position.

The combination of the ease at which artificial DNA samples can be manufactured, with the fact that a registered DNA profile found at a crime scene will automatically lead to a database "match", and the heavy weight of DNA evidence in the courtroom, creates a problematic situation which we believe should be addressed by the forensic community by adopting a DNA authentication assay for casework samples.

SNP Based Profiling Approaches are Also Susceptible to Fabrication.

Recently, alternatives to STR based profiling have been proposed, primarily single nucleotide polymorphism (SNP) based approaches, in which sequence variants are used for generating a "profile" (Sobrino et al., SNPs in forensic genetics: a review on SNP typing methodologies. *Forensic Sci Int* 154 (2005) 181-194). SNP based approaches may be advantageous over STR profiling, since they perform better on degraded DNA samples, and they are easily detected using an automated high-throughput system Butler et al., STRs vs. SNPs: thoughts on the future of forensic DNA testing. *Forensic Sci. Med. Pathol.* 3 (2007) 200-205; K. Babol-Pokora and J. Berent, SNP-minisequencing as an excellent tool for analysing degraded DNA recovered from archival tissues. *Acta Biochim. Pol.* 55 (2008) 815-819; Nakahara et al., Automated SNPs typing system based on the Invader assay. *Leg Med* (Tokyo), 2009). Similar to STR based profiling, SNP based approaches are also susceptible to fabrication by the methods described here. Even if a very large number of SNPs are to be used in profiling, this will not effectively deal with the problem of WGA-based fabrication, since WGA produces a full representation of the genome, and therefore is expected to produce a perfect "SNP profile".

Integrating DNA Authentication into the Forensic Procedure.

The DNA authentication assay described here can be used to distinguish between natural and artificial DNA, regardless of the method used for producing the artificial DNA. Since the assay employs bisulfite sequencing, a procedure that is relatively labor intensive, time consuming, and requiring specific expertise, it may be best suited as a service provided by dedicated labs to the forensic community. However, in order to reduce costs and possible backlogs, and to reduce the risks of errors related to lengthening of the chain of custody, it may be advantageous to develop an integrated DNA authentication assay that will be performed in existing forensic laboratories, as part of the regular forensic procedure.

Other Approaches to DNA Authentication.

Analysis of methylation patterns represents only one of several possible approaches that can be used for DNA authentication. Alternative methods may be based on analysis of stutter products, representation bias, distribution of DNA fragment sizes, and presence of non-genomic sequences. Stutter products are artifacts caused by slippage of the DNA polymerase on repeated sequences (Shinde et al., Taq DNA polymerase slippage mutation rates measured by PCR and quasi-likelihood analysis: $(CA/GT)_n$ and $(A/T)_n$ microsatellites. *Nucleic Acids Res.* 31 (2003) 974-980), and are expected to be found in higher percentages in pre-amplified artificial DNA. Representation bias refers to differences in copy number between different genomic loci that are an inherent consequence of in vitro amplification of DNA (Lasken et al., Whole genome amplification: abundant supplies of DNA from precious samples or clinical specimens. *Trends Biotechnol.* 21 (2003) 531-535). Analysis of the distribution of fragment sizes can also reveal the origin of the DNA: in natural DNA, the distribution has an expected stereotypical pattern (which is a function of the extraction method used and the extent of degradation), different from the patterns observed in various types of in vitro synthesized DNA. Non genomic sequences such as primer dimers, plasmid sequences, artificial oligonucleotide linkers, etc., are not expected to be found in natural DNA (with the possible exception of bacterial sequences), but are expected to be found in various types of in vitro synthesized DNA.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

SEQUENCES

Constitutively Methylated Loci:

NT_010718.15

(SEQ ID NO: 25)

cccagaaggcatgtgggctggctcaataaaatattaagcagctctttccaacgatgtggctgatggtttgtgtggtt gttagagagcccaggagacaggcagaaaggaaggcatgtgaccggatcacaatcatcagctctctgctgtcctcttt -continued gggaagggttttagtattaaaaggacatttattctcattaatgcaaaattaaggagttttaaaagcttttacaacct agactccctctgagaggttagccttgacaccctaatcgccttctgctcccgccactgctcggtgccaagcagctccc acggccccggcgggtctgatgatagccggacaggagggaggaaggggaggaggaagagcctgcatcagctcctacga ttgcccagccccatcctgggagtgattaaacggtgcatcaccaaatgccagtcccactgacaggcaggtcaccgtgc acttcagggcactctaaattgccgactctccatgtagag

AF216671

(SEQ ID NO: 26)

2281 aattgcaagt ccattagaga cctgggcttc tgacctgata ctgccaccta ctatctctat 2341 ttccttgagc tagttctgta acctttcaa ttctcagtgt tctcctcttc aaaatgggga 2401 tcatagtctc tgactcataa ataggaagat aaataaattc atccaaggaa aaaagcatgg 2461 tacccagcaa ataggaagca cttcattaag tgtttgctat tattattact ttttttttt 2521 ttttttttgag atagagtctc tctctgttgc ccaggttgga gtgcaattgt gcaatcttgc 2581 ctcactgcac cctccacctc ccggtttcaa gtgattctcc tgcttcagcc tcccaaatag 2641 ctgggatcac aggcacgcac caccgtgccc agctagctaa ttttttgtatt tttagtagag 2701 acatggtttt gccatgttgg tcaggccggt ctcaaactcc tgacctcagg tgatccaaag 2761 tggatcctca gctcccaaa gtgctggaat tacagccgtg agccaccgca cccagcctgt 2821 tattactatt actatcatta ttgctcctcc tcctcctata ctacagcaag agcgcttgaa Partially Methylated Loci:

NW_92770

(SEQ ID NO: 27)

157861 ctcttccttc actctctccc ttcctctctc tttctattct cctcccctcc tcctgtaaa 157921 agctaccacc tcatcctggg caccctggtt atatcaactt cagctatgag gtaattttc 157981 tctttactaa ttttgaccat tgtttgcgtt aacaatgccc tgggctctgt aaagaatagt 158041 gtgttgattc tttatcccag atgtttctca agtggtcctg attttacagt tcctaccacc 158101 agcttcccag tttaagctct gatggttggc ctcaagcctg tgtcgtccca gcagcctccc 158161 gcctggccac tctgactcag tctgtcctcc taaatatggc cgtaagctta cccatcatga

NT_011896

(SEQ ID NO: 28)

3661 cttcctgagc agtggttcat gaatgaataa acttacagcc atatttagga ggaaagagtc 3721 aatccgaatg gtcaggcagg agggtgctgg agcaacacag gcttgaggcc aaccatcaga 3781 gcttaaactg ggaagctgat ggtaggaact gtaaaattgg gaccacttga gaaccacttt 3841 tatttgggat gaagaatcca cccactattc tttacagagc caggggact gctaatgcaa 3901 acagtgatca aaattagtaa agagaaaaat tacctcatag ctgaagttga tataaccagg 3961 gtgcccagga tgaggtggta gctttttatag ggaggagggg aggagaagag aaagagagag 4021 gaagggagag tgtgaaggaa gggaagagag agtaagagat taagtcaata tgcaattgtt

X14720

(SEQ ID NO: 29)

11641 cagctgggat gtggagtggt gtgaggagtg gccacagggg agcagaggag gtggcagaag 11701 ccggaggtaa aggtgtctta aagtgagaaa gaataactgc atcttaacct attgggaggt 11761 cattgtaaag aggagagtga tggggtcaga ttgtacagag gaggcacttc gtggtggtca 11821 ggagcacaca ctccagggca gtgttccaac ctgagtctgc caaggactag caggttgcta 11881 accaccctgt gtctcagttt tcctacctgt aaaatgaaga tattaacagt aactgccttc 11941 atagatagaa gatagataga ttagatagat agatagatag atagatagat agatagatag -continued

```
       12001 atagatagat aggaagtact tagaacaggg tctgacacag gaaatgctgt ccaagtgtgc
       12061 accaggagat agtatctgag aaggctcagt ctggcaccat gtgggttggg tgggaacctg
```

AC010136                                                                  (SEQ ID NO: 30)
```
       66781 cgttcatttc ttcctagcac ttagaactgt ttcttgttga tacatttgct ggcttcttcc
       66841 ctgtctcacc ccttttccta ccagaatgcc agtcccagag gcccttgtca gtgttcatgc
       66901 ctacatccct agtacctagc atggtacctg caggtggccc ataatcatga gttattcagt
       66961 aagttaaagg attgcaggag ggaaggaagg acggaaggaa ggaaggaagg aaggaaggaa
       67021 ggaaggaagg aaggaaggaa ggaaggcagg caggcaggca ggcaggcagg caaggccaag
       67081 ccatttctgt ttccaaatcc actggctccc tcccacagct ggattatggg ccagtaggaa
       67141 ttgccatttt cagggttttg ctgtcactgt agtcaggacc atgaagtctt taggcacctc
       67201 cactccacac accccctggt gagagctccc atctccctgt tctgaaacag ctccccaata
```

AC099539                                                                  (SEQ ID NO: 31)
```
       77521 ttggaaggct gagatgggag gatcacttga ggccaggagt ttaagacaag gctggggaac
       77581 acagcgagac cccatctctt aaaaaaaaaa attagccgga catggtggct catgcctata
       77641 atcccaggta cttgggaggc tgaggcagga ggactgcttg agcccaggag tttgaggctg
       77701 tagtgagcta tgattccccc actgcagtcc aatctgggtg acagagcaag accctgtctc
       77761 atagatagat agatagatag atagatagat agatagatag atagatagat agatagacag
       77821 atagatacat gcaagcctct gttgatttca tgagtataag agatgccccc aaaggcacag
       77881 ggaatacaca ccacagaaaa atagatccct gggcagaagt gggcaagtga atatggccag
       77941 catgcccatt ctggagcagt gccctggcag ctgcagtcct cacctgggaa tagcttttcc
```

NT_006576                                                                 (SEQ ID NO: 32)
```
     1282681 acaatggcac aatctcagct cactgcagcc tccgcctcct gggttcaagt gattctcctg
     1282741 cctcagcctc ccaagtagct gggattacag gcacacacca ccatgcccag ctaattttg
     1282801 tattttagt acagataggg tttcaccatg ttggtcaggc tggtctcaaa ctcctgacct
     1282861 caggtgatcc acctgcctca gcttcccaaa gtgctgggat taccggcgtg agccaccgca
     1282921 cctggccgtc aacacacaat taatcttaa acacaaacct gcatattggc tgaccacgtg
     1282981 cacctgcaaa acccttacct cccaccccca ggaagagggg gttctcgtcc ccacctctca
     1283041 ttcccacccct tgaaattgcg aagaggatta taggtaacct gcaggcaccc tcgccagagc
     1283101 gtctgtgctt ccagacactt ctccccattg ccggcaaccc ggctccactg ccgcgcccag
     1283161 cctcctctgt tcactgctct ggcctcggcg cctggaaacc gcgtgtccat caaaacgtga
     1283221 aggtgaacct cgtaagttta tgcaaactgg acaggaggga gagcagaggc agagatcacc
     1283281 gtgtccactc gacgtcctga gcgaaaagcc acgtgtgccc acgtgacgat ggagacagga
     1283341 ggaccagggc tctgcctgcc ccctttctg agccccact gcattcagct ctggggcctg
     1283401 ggccctcgac ggccaccacc tcctcacctg ggctcctgcg cagccaagcg cagtcccgca
     1283461 cgctcatctt ccacgtcagc tcctgcagcg agagcttggc atgcttcccc agggagatga
     1283521 acttcttggt gttcctgagg aagcggcgtt cgttgtgcct ggagcccag aggcctgggg
     1283581 gcaccagccg gcgcaggcag gcccgcacga agccgtacac ctgccagggg ctgctgtgct
     1283641 ggcggagcag ctgcaccagg cgacgggggt ctgtgtcctc ctcctcgggg ccgccacag
     1283701 agccctgggg cttctcccgg gcacagacac cggctgctgg ggtgaccgca gctcgcagcg
     1283761 ggcagtgcgt cttgaggagc accccgtagg ggcactgcgc gtggttccca agcagctcca
```

-continued

```
1283821 gaaacagggg ccgcatttgc cagtagcgct gggcaggcg ggcaacctg cggggagtcc 1283881 ctggcatcca gggcctggaa cccagaaaga tggtctccac gagcctccga gcgccagtca
```

AC008512 (SEQ ID NO: 33)
```
  80521 agggaatttt ctaactttga actacacaac acgcctttcc tctgaagtga agctggttaa 80581 ctttcaccat attttcttgt ttctttacct ttaactttga gctattaggc atgggagagg 80641 gagagggtct ggcttacccc ctcattttga aaatacatgg gagaaaataa tacatagcca 80701 catttgtaat tttctaattc aaaggagtat ataattatgt aataatttta aaattaaata 80761 ctgagacatg catatgcttt taaagcttct aattaaagtg gtgtcccaga taatctgtac 80821 taataaaagt atattttaat agcaagtatg tgacaagggt gattttcctc tttggtatcc 80881 ttatgtaata ttttgaagat agatagatag atagatagat agatagatag atagatagat 80941 agaggtataa ataaggatac agataaagat acaaatgttg taaactgtgg ctatgattgg 81001 aatcacttgg ctaaaaagca ctaaagcatt cctctgagag agacaattac ttttttgctt 81061 aggaaactac ctcaacagcc tattagcatc tgaaatatga ggtccactat ccagatggga 81121 gaggtttaga aaaagaagac ttatattact ctgtataatg aaatgatgga gtatttggag 81181 ttattcacca gtgctttgag aaaggaattg ggatcctgaa agaggaaact ggaagaagta 81241 gctagaggga gagaacctca caatgtggca catagccagg ctacacagag ggacatgact 81301 atacaggcgt tgtagataac atttccaata atgttgctat aatttaaaga tgtttcctac
```

AC004848 (SEQ ID NO: 34)
```
 103561 aaaacaaaac aaaacaaaat actgaaacca gtgtgaacaa gagttacacg atggaaggca 103621 tcagttttca caccagaagg aataaaaaca ggcaaaaata ccataagttg atcctcaaaa 103681 tatgattgat tttaagcctt atgagataat tgtgaggtct taaatctgaa ggtatcaaaa 103741 actcagaggg aatatatatt cttaagaatt ataacgattc cacatttatc ctcattgaca 103801 gaattgcacc aaatattggt aattaaatgt ttactataga ctatttagtg agattaaaaa 103861 aaactatcaa tctgtctatc tatctatcta tctatctatc tatctatcta tctatctatc 103921 tatctatcgt tagttcgttc taaactatga caagtgttct atcatacect ttatatatat 103981 taaccttaaa ataactccat agtcagcctg accaacatgg tgaaaccccg tctctaaaaa 104041 aaatacaaaa attagctgga tgcagtagca catgcctgta gtcccagcta ctcaggaggc 104101 tgggcagga gaaccacttg acccaagaag cggaggttgc agtgagccga gatcgcacca
```

AF216671 (SEQ ID NO: 35)
```
   2881 ccagatgtag gggagatagc agctggagag cataacagag gcactgacat gtgagcagct 2941 aacgaggcct tttacaagac atctgtgacc acacggccaa gtagaagaaa gccgttaaaa 3001 gcatcaaggt agttaggtaa agctgagtct gaagtaagta aaacattgtt acaggatcct 3061 tggggtgtcg cttttctggc cagaaacctc tgtagccagt ggcgcctttg cctgagtttt 3121 gctcaggccc actgggctct ttctgcccac acggcctggc aacttatatg tatttttgta 3181 tttcatgtgt acattcgtat ctatctgtct atctatctat ctatctatct atctatctat 3241 ctatctatct attccccaca gtgaaaataa tctacaggat aggtaaataa attaaggcat 3301 attcacgcaa tgggatacga tacagtgatg aaaatgaact aattatagct acgtgaaact 3361 atactcatga acacaatttg gtaaaagaaa ctggaaacaa gaatacatac ggttttgac 3421 agctgtacta ttttacattc ccaacaacaa tgcacagggt ttcagtttct ccacatcctt 3481 gtcaacattt gttatttct gggttttga taatagctgt gaaggaaaa taaaaacttg 3541 ggccgggcgc ggtggctcac gcctgtaatc ccagcacttt gggaggccaa ggcgggcaga
```

-continued

```
     3601  tctcaaggtc gggagattga gaccatcctg gctaacatgg tgaaacccca tctctactaa
     3661  aaatacaaaa acaaaaaatt agccgggcgt ggtgacgggc gcggtggcgg gcgcatgtag
     3721  ttccggctac tcgggaggct gaggcaggaa aacagcatca acccgggagg cggcgcttgc
     3781  agtgagccaa gatcgcacca ctgcactcca gcctgggcga cagagcaaga cacggtctca
     3841  aaagaaaaaa agaaaaaaaa aacttggtac cccagttcct tctgccaaaa ggaaacaatt
     3901  aagctgaaag ctgagtcatg caagaagttg ccttttcttt tgtccctaag cagagagcta
     3961  ttaaaagtta tggcaaaaac cgcgattact tttgcaccaa ctaaaataat agctgatgac
     4021  ctaagacatc tctctgcact cactttctgt ctcggctgtg cttttcactc ttcctccttc
     4081  ctccaaatgt taggaaaatg agtccaacaa gaaatacatc cataaagcaa aggcattctg
     4141  gtgactcctg tacacatcat gactgtccac ccaaagcctg gcattgcctc taggaagtcc
```

AL353628.2                                                     (SEQ ID NO: 36)

```
    20401  ttatttgggt aggaaaaaga gtggaggagt tttaactcac agataacagt ctgaaagtac
    20461  aagtggggaa atttgtacat tcattaatat acattatttt caaaacatat tcagagagct
    20521  tgaattgttg gtcaaatctc ctccttcaac ttgggttgag ccataggcag cccaaaaaga
    20581  cagacagaaa gatagataga tgattgattg atagatagat agatagatag atagatagat
    20641  agatagatag ataatgtatt tgtaaataca gataggcgtt agatgggtca gagtccagag
    20701  agtcacggat gcccactaaa gaatgaact  ctcctccaca tcccagactt ctgtgatacc
    20761  atgtccagca acccatccca atattcacat tggctgtagg cagaattacc atttgttcat
    20821  gtcaaaatat ttattgatca tgtgttatat gctagaaatg taactaagtg cttgcaatac
    20881  atcaataaat aatgcagtga acagaagagt cttactatgg cagctttcca atgagtcagc
```

AC024591                                                       (SEQ ID NO: 37)

```
    10321  ggggaactga gaggctactt tttgacccag gaccctaagc ctgtgtacgg agagagcatg
    10381  agctgggtga gctgcttgcc aaggagtggc atctgccctc atcagtggac acaaaaagcc
    10441  ccaggggtta agtggccatg gctgccctca tggctgcacc gggaggatga ctgtgttccc
    10501  actctcagtc ctgccgaggt gcctgacagc cctgcaccca ggagctgggg ggtctaagag
    10561  cttgtaaaaa gtgtacaagt gccagatgct cgttgtgcac aaatctaaat gcagaaaagc
    10621  actgaaagaa gaatcccgaa aaccacagtt cccatttta tatgggagca aacaaaggca
    10681  gatcccaagc tcttcctctt ccctagatca atacagacag acagacaggt ggatagatag
    10741  atagatagat agatagatag agatagatat agatatcatt gaaagacaaa acagagatgg
    10801  atgatagata catgcttaca gatgcacaca caaacgctaa atggtataaa aatggaatca
    10861  ctctgtaggc tgttttacca cctactttac taaattaatg agttattgag tataatttaa
    10921  ttttatatac taatttgaaa ctgtgtcatt aggttttaa gtctatggca tcactttcgc
    10981  ttgtattttt ctattgattt ctttcttt cttttctttt tttgagacag agtctcactc
    11041  tcacccaggc tggagtaccg tggcacgatc ttggctcatt gcaaccacca cctcccgggt
```

AP001534                                                       (SEQ ID NO: 38)

```
    85501  ctactatgga ctaatattag tttggtcttg accagaagaa atccttgtgc gtatttatgt
    85561  tgaaagatga ataacttac tgaaattgtt aatgaagtat tggataagct actttaaaaa
    85621  taacaaaccc gactaccagc aacaacacaa ataaacaaac cgtcagccta aggtggacat
    85681  gttggcttct ctctgttctt aacatgttaa aattaaaatt aacttctctg gtgtgtggag
    85741  atgtcttaca ataacagttg ctactatttc ttttctttt ctctttcttt cctctctctt
    85801  tttctttctt tctttctttc tttctttctt tctttctttc tttctttctt tctttctttc
```

```
                                              -continued
85861   tttctttctt tctgagacaa ggtctcaatt tgtcactcag agtgaagtgc agtggcatga 85921   acatggctca ctgcagcctt aaccttctgg gctcaagaac tcctcctgcc tcagccctgc 85981   aagtagctga gactacaggc acgtgccacc atgcccaact aattttttgta tttttttgta 86041   gagacagggg tctcactgtg ttacccaggc tggtctcaaa ctcctgagct caattgatcc 86101   acctgtctca gcctcccaaa gtgctgggat tacaggtgtg agccatcacg cttggcctat
```

AC008507.7
(SEQ ID NO: 39)
```
155341  tttcttttaa ccttgtactg cagtttaaca catatgcaga aaagtgcaca aatccttagc 155401  gaattttcac aaagtgagca atcctgtata tccagctctc aggtcaagaa acagaacatt 155461  tctaaggctg ggtgaggtgg ctcatgcctg caatcccagc actttggaag actgatgcag 155521  aaagatcact tgagggaagg agttcaagtc tagtctgggc aacatagtga gacctcttct 155581  ctataaaaaa ttttttaaaa ttagccaggc atgttggcac attcctgtag tcctggctac 155641  tcaggaggct ggggcaggaa gatcacttga gcccaggagg ttgaggctgc aaaaagctat 155701  aattgtacca ctgcactcca gcctgggcaa cagaataaga ttctgttgaa ggaaagaagg 155761  taggaaggaa ggaaggaagg aaggaaggaa ggaaggaagg aaggaaggaa ggagagagga 155821  agaaagagag aagattttta ttcgggtaat gggtgcacca aaatatcaga aatcactgct 155881  aaagaactta ttcatgtaac caacaccacc tgttccttaa aaacctattg aaataaaaac 155941  agaaagaaag agagaaagag gaaggaagga aggaaggaaa gaaggaagat tgattcctag 156001  aaccccagga gcctccaag gtcctttttgt tcaccatcca ccatcccttc ctccccccag 156061  tcctggtaac cactattcca acttccaatc ctttggacta gtgccatctg ttttaaact 156121  tcataccaat ggactcatac ggtatgtgct ctggggtctg gtttctgtgt ccagtttcat 156181  gttagttctt gtagcatttt aatcagagcc ggtcacataa tttgtagtgc ccagtgcaaa 156241  atgaaagtgt ggaccatccc ctccaacccc acccccaaca ccattcaaaa gttattaaga 156301  atttcaagat ggcagctgca gagcctaagt cagtcacggg attcttctga gtgcacagcc
```

AP000433
(SEQ ID NO: 40)
```
3841    tctgaatgtc aactcgactg gattaagaga tacctagata gtggtaatgc attctttctg 3901    tgtgtatccg tgaattggtg ggctgagtgg agaaatatctg ccttcaatgt gggcagatgc 3961    cataccgttg gctggggctc agagagaaca aaaaggcaga ggaaaaacaa atttcccctc 4021    tcacttctgg agatggaaca cttttcttct gcttttggac atcagaaatc caagttctct 4081    ggcctttgga ctttgggact tgtgccagca ccctcctggg ttccctggcc tttggcctca 4141    aactgaaggt tacactatca gcttccgttg ttctaagggc ttcagacttg acagccaca 4201    ctgccagctt ccctgattct tcagcttgta gatggtctgt tatgggactt ttctcagtct 4261    ccataaatat gtgagtcaat tccccaagtg aattgccttc tatctatcta tctatctgtc 4321    tgtctgtctg tctgtctgtc tatctatcta tatctatcta tctatcatct atctatccat 4381    atctatctat ctatctatct atctatctat ctatctatct atctatcgtc tatctatcca 4441    gtctatctac ctcctattag tctgtctctg gagaacattg actaatacaa catctttaat 4501    atatcacagt ttaatttcaa gttatatcat accacttcat acattatata aaaccttaca 4561    gtgtttctcc cttctcagtg tttatggcta gtaattttttt actgggtgcc agacactaat 4621    ttttattttg ctaagtggtg aatatttttt atatccttaa aaatattttt gagtgttgat 4681    ctgggtaaag ttaagttcaa tattggaaaa atattgattc ttttgaggat agttatcttc 4741    taattagtct acctgttgcc ccataaatgg catgattttc cactctgtgt gagtcctcga
```

-continued

M64982
(SEQ ID NO: 41)

```
2581  atctatagag ttaaaaagaa aagctcatca gtaagaaaat ccaatatgtt caagtccctt
2641  gattaaggat gttataaaat aattgaaatg caatcaaacc aactattta actccaaatt
2701  acacctttaa aattccaaag aaagttcttc ttctatattt ctttgggatt actaattgct
2761  attaggacat cttaactggc attcatggaa ggctgcaggg cataacatta tccaaaagtc
2821  aaatgcccca taggttttga actcacagat taaactgtaa ccaaaataaa attaggcata
2881  tttacaagct agtttctttc tttcttttt ctcttctt ctttctttct ttctttcttt
2941  ctttctttct ttctttcttt ctttctcctt ccttccttc ttcctttctt ttttgctggc
3001  aattacagac aaatcactca gcagctactt caataaccat attttcgatt tcagaccgtg
3061  ataatcccta caaccgagtg tcagaggatc tgagaagcag aattgaagtc ctgaagcgca
3121  aagtcataga aaaagtacag catatccagc ttctgcagaa aaatgttaga gctcagttgg
3181  ttgatatgaa acgactggag gtaagtatgt ggctgtggtc ccgagtgtcc ttgttttga
3241  gtagaggaa aaggaaggcg atagttatgc actgagtgtc tactatatgc agagaaaagt
```

Ap001752
(SEQ ID NO: 42)

```
29461  tcgcttgaac ccaggagggg gcgactgcag tgagccgaga tcgtgccact gcactccagc
29521  ctgggtgaca gagcgagact ccatctcaaa aaaaaaaaa aaaaacaga atcataggcc
29581  aggcacagtg gctaattgta ccttgggagg ctgagacggg aggatcgaga ccatcctggg
29641  caccatagtg agacccatc tctacaaaaa aaaaaaaaa ttttttta atagccaggc
29701  atggtgaggc tgaagtagga tcacttgagc ctggaaggtc gaagctgaag tgagccatga
29761  tcacaccact acactccagc ctaggtgaca gagcaagaca ccatctcaag aaagaaaaa
29821  aagaaagaaa agaaaagaaa agaaaagaaa agaaaagaaa agaaaagaaa agaaaagaaa
29881  agaaaagaaa aaacgaaggg gaaaaaaga gaatcataaa cataaatgta aaatttctca
29941  aaaaaatcgt tatgaccata ggttaggcaa atatttctta gatatcacaa atcatgacc
30001  tattaaaaaa taataatata gtaagtttca tcaaaactta aaagttctac tcttcaaaag
30061  ataccttata aagaaagtaa aaagacacgc cacaggctaa gagaaagtac ttctaatcac
30121  atatctaaaa aaggacttgt gtccagatta aagaattctt acacatcaat aagacaaccc
30181  aattaaaaat gggcaaaaga tttgaagaga tatttaacca agaaaacat ataaatgtgt
30241  ccgggcgcga tggtaatccc agcactttga gaggccgagg caggcggatc acttgaggtc
30301  aggagtttag gaccagtctg gccaacatgg tgaaaccctg tctctaataa aaatacaaaa
```

Ac027004
(SEQ ID NO: 43)

```
84241  gttttaaaag ccgaatattt taggacaata tatggtaata atcaatcaat ggtttcagcc
84301  ttagttttac tactggtcta ctttgggctt aaagttgacg tctcattgca ttgaaaatta
84361  tttgataaga gaaaataaaa tacatttttac caacatgaaa gggtaccaat aacaagaaaa
84421  ttgtggacag gtgcggtgat tcacgcctgc aatcctagca ctttgggagg ccgatgcagg
84481  tgtattacct gagctcagga gatcaagacc agcctgggca acatggtgaa accccgtctc
84541  tactaaaata caaaaaatta gctgggtgtg gtggtaggca cctgtaatcc cagctactct
84601  ggaggctgaa acaggagaat cacttgaacc caggaggtgg agattgaagt gagccgagat
84661  cacgccattg cactccagcc tgggcgactg agcaagactc agtctcaaag aaaagaaaag
84721  aaaagaaaag aaaattgtaa ggagttttct caattaataa cccaaataag agaattcttt
84781  ccatgtatca atcatgatac taagcacttt acacacatgt atgttatgta atcattatat
84841  catgcatgca aggtaatgag tattattttc ctcatttat aaaagaggaa actgatgttt
```

-continued

```
84901  gaggctactt tgcttaagac cacagaacta gcaaaggaaa agagaagtga atgtatccct
84961  gatccccttt aacacttctt acacagcctc cccacaatgt ccagtattaa cttcataaat
```

V00481                                                              (SEQ ID NO: 44)
```
    1  ctacagtgag ccgaggtcat gccattgcac tccaatctgg gcgacaagag tgaaactccg
   61  tcaaaagaaa gaaagaaaga gacaaagaga gttagaaaga agaaagaga gagagagaga
  121  aaggaaggaa ggaagaaaaa gaaagaaaaa gaaagaaaga gaaagaaaga aagagaaaga
  181  aagaagaaa gaaagaaaga aagaaagaaa gaaagaaaga aaaagaaaga aagaaagaaa
  241  gaaagaaaga aagaaagaaa gaaagaaaga aagaaagaaa ggaaggaaag aaagagcaag
  301  ttactatagc ggtaggggag atgttgtaga aatatatata aacctcctta caccgcggag
  361  accgcgtcag cccagcgagc acagaacctt gtccttgccg ctgcgccttg cgtccgcacc
  421  cgccgccagc tcaccatgga tgatgctatc accgcgctcg tcgtcgtcga caactgctcc
  481  agcatgcgca aggctcccca ggccgtcttc ccctccattg tggggcaccc taggcaccag
```

D00269                                                              (SEQ ID NO: 45)
```
  901  aaatccatcc aaaaaatcca agatggccag aggtccccgg ctgctgcacc cagcccccac
  961  cctactccca cctgccctg cctccctctg ccccagctgc cctagtcagc accccaacca
 1021  gcctgcctgc ttggggaggc agccccaagg cccttcccag gctctagcag cagctcatgg
 1081  tgggggtcc tgggcaaata gggggcaaaa ttcaaagggt atctgggctc tggggtgatt
 1141  cccattggcc tgttcctccc ttatttccct cattcattca ttcattcatt cattcattca
 1201  ttcattcacc atggagtctg tgttccctgt gacctgcact cggaagccct gtgtacaggg
 1261  gactgtgtgg gccaggctgg ataatcggga gcttttcagc ccacaggagg ggtcttcggt
 1321  gcctccttgg gcactcagaa ccttgggctc cctggcacat ttaaaatggg ttttttattta
 1381  tggaccttga ttgaaatgtg gtgtgagttg tagcagtgtc atttccaggt accttctcag
 1441  ggacacaggc gcccctcccc cgtcctcccc cgccctcccc tacctccccc caccaggctc
 1501  cccatcaggc atcccctccc cagggcgccc cggggcccag cctcacaggc tctccgtggc
 1561  ctggaactgc agccccagct gcatcctaca ccccccaccc aagggtaagt aagaggggac
 1621  tctgggaggg gcttctgctg ctcccccttca tgttccacaa ccctggaagc tcaggatgaa
```

M68651                                                              (SEQ ID NO: 46)
```
 1681  caaccccac cttcctctgc ttcactttc accaactgaa atatgccaa aggcaaaaac
 1741  ccatgttccc actggcctgt gggtccccc atagatcgta agcccaggag gaagggctgt
 1801  gtttcagggc tgtgatcact agcacccaga accgtcgact ggcacagaac aggcacttag
 1861  ggaaccctca ctgaatgaat gaatgaatga atgaatgaat gaatgaatga atgaatgttt
 1921  gggcaaataa acgctgacaa ggacagaagg gcctagcggg aagggaacag gagtaagacc
 1981  agcgcacagc ccgacttgtg ttcagaagac ctgggattgg acctgaggag ttcaattttg
 2041  gatgaatctc ttaattaacc tgtgtggttc ccagttcctc ccctgagcgc ccaggacagt
 2101  agagtcaacc tcacgtttga gcgttgggga cgcaaacacg agagtgcttg gtgtgagcac
 2161  acaggaggag tcacgacaca gcagtgtaag agccgccacg agggtcccac acaggggag
```

M25858                                                              (SEQ ID NO: 47)
```
 1321  aatcatataa tcggagaaac ttatttgtac tcgtgaaatt gatcagaaat aaatagaagt
 1381  cctgtagggg agggagatgt ggcttgagaa caattaatgt aaaggaggtc ttagaatgtt
 1441  agcagtagag agaactagag ggatcattta cttcaagccc ctcatttat agacattact
 1501  agtctcctac aatgtgccgg gcactttgcc cttattattt tgtgaactcc tcagactgat
```

```
-continued
1561  cctataaggt agagttccca ccttccagaa gaagaaacag gtctagagga tccaagttga
1621  cttggctgag atgtgaaagc cctagtggat gataagaata atcagtatgt gacttggatt
1681  gatctatctg tctgtctgtc tgtctatcta tctatctatc tatctatcta tctatctatc
1741  tatctatcta tctatccatc tatccatcca tcctatgtat ttatcatctg tcctatctct
1801  atctaaccta tgtatctatt tatcatctat cctgtctcta tctatccttt gtatctatca
1861  tctatcctat ctctatctaa gctatatatc tatttatcat ctatcctcta tcatctatct
1921  atctatctat ctatctatct ctattgtatc tagttatcta tcctatatct atgtatgtat
```

Constitutively Unmethylated Loci:

NT_007914.14

(SEQ ID NO: 48)

GCAGCGCTAGCCGGCAGTATTTCCAAGGCGCAAGTTGCGGAGTTTCTGTTTCCTTTTTCCTCTGGCGAGC

TTTGCGTTCCCTGTGCGCCGGAAGTGATCCCCTGCGTGGCTGGGCTGCTCGGGTTAGATCGTCAGGTGAG

GGAGGAAGGGATAGCCAGCGCGAAGGAAGTGCTGGAGTCGTGTGTTTTGGCTGCGCGTGATCCTGCGTGG

GTCGGGAGGTGTTTCTGTGTAGGTGTCTGGCCCTTTCATCAGTCGTGCGGAGGACCGCGTGATTTCCTTC

CAGTTCTCCTCGGTTTTCAGGTGGTGGCGCCATCTTCGGTAAAGGGTGTCCACCTCTCCCTATGGTGTGG

CTGGCTAGCCCGGGGGTCTCTACGCTGCTTGGTCTTTGTTAACGGAGATGAAGGCAGTAATTTTTCAGTA

ACAGGTTTCAGATATAAGTCCCTTGGTGATGCTAATATTTATGGAGGCCTTACTATGCATTAAGAACTTT

TTTAGAAGTTTAGAAAATGGCAGTGAATAAAGCAGATACAAATCTCTGCTCTAAGGGAGCTTGCATAGTA

ATGAAATTTGAGAAGACAGTGGATTGGAAGTGGGATTAACT

NT_022853

(SEQ ID NO: 49)

cggcccaagcttgacctacaatttgcgcaggcgcagatcctaactttggcgtccctgtgg gcggcctttggtgtgagacgcgtggtattctgggaacgtcggagacggaagttacttcgt ctttagctcctggcgctgctggcttctgggcggttttttgtcttttgatttcaagagttag gagctcgagaaccgtttggcaatatgtacgacgcggatgagggtaggtgaacgctcaaaa cacacgccgtggcggtccatttaagcaggaaagcgttgggaactgattggattgaggatt tggggccttcccatgcgccggctgcacagtccccagccttgttcccacacttaccaggcc gggaacgaaactgggtagggagaggcggagggtgcagggaacatagtgttaatgttcca ggttacgttcactgctgctctctgcactttctcgttccgttagatctgatcctcgtttcc tgtggtgaagtagcgtgcagaatcgtaagataaaattacgttttgaatttgaagcaaaggg cacccttaaaaatttccttaaagccacagtcgacttaacgaatagctcaattgttgag Contiguous Sequence Containing Constitutively Methylated, Partially Methylated, and Constitutively Unmethylated CG Loci:

NT_009237.17

(SEQ ID NO: 50)

Constitutively_methylated>[catctcctaagtaaagaagggaacccacacttgttgagggcctatatagg accatgaactggggacacaaactcaacctcacgatagcactgatgaggcatgttctactaagctcatttacagtga ggaaagagaggaccagccgggcacggtggttcacggctgtaatcccagcactttgggaggccgaggcgggcggatca caaggtcaggatttggagaccaacctggccaagatggtgaaaccccatctctactaaaaatacaaaaattagccggg tgtggtggcgcgcgcctgtactcccagctacctgggaggctgaggcagaagaatcgcttgaacccgggaggcggagg ttgcagtgagccgagatcacgccactgcactccagcctgggcgacagagtgagactccgtctaaaaaaaaaaaaaga -continued aaagaaatcatattctcaacgttggaatcggcctcccagttgcaaatcccaccacaatacaacag]partially_ methylated>[caattacaactctcaactacaattatgtttgcatagagcttcacggtttacaaagcccaggttacg ttttgcaattatcctgtttcacagattaagaagttgaactgaggccgggcgcagtggctcacgtctataatcccagc actttgggaggcggggcgggaggatcacgaggtcaggagttcgagaccagcctggccaacatggtgaaaccctgtc tctactaaaaatacaaaaattagccgggcgtggtggcggacg]constitutively_unmethylated>[cctgt aatcccagctactcaggaggctgaggcaggagaatcgcttgaatccgggaggcggaggttgcagtgaaccgagactc cagcctgggcaataagagtgaaactccgtcttaaaaaaataaataagttgaactgaaagcgtggcctaataagtggc aaggaggaacacttcccccaaatttcttcttcttagtgctttgccagatcagatctgggagatttccccctcccgcc ggc]

What is claimed is:

1. A method for determining whether a DNA sample from a human forensic sample is an artificial sample, comprising:
 (a) obtaining a DNA sample from a human forensic sample;
 (b) subjecting the DNA sample to sodium bisulfite, thereby producing bisulfite-treated DNA;
 (c) amplifying a set of loci of the bisulfite-treated DNA in the presence of primers specific for the set of loci, the set of loci containing a reference Combined DNA Index System (CODIS) locus and a plurality of non-CODIS loci, said plurality of non-CODIS loci comprises:
  (i) one or more first CG loci, each of said first CG loci comprising at least one $C_pG$ dinucleotide being constitutively methylated or partially methylated in natural human DNA; and
  (ii) one or more second CG loci, each of said second CG loci comprising at least one $C_pG$ dinucleotide being constitutively unmethylated in natural human DNA;
 (d) determining the presence or absence of amplification products of the set of loci of the bisulfite-treated DNA after step (c) and determining whether the DNA sample is an artificial sample, wherein
 the presence of said reference CODIS locus in said amplification products and the absence of said plurality of non-CODIS loci in said amplification products indicates that the DNA sample is an artificial DNA sample,
 (2) the presence of both said reference CODIS locus and said plurality of non-CODIS loci in said amplification products indicates that the DNA sample contains a full representation of the genome and is either a natural DNA sample or an artificial DNA sample synthesized by whole genome amplification (WGA), and wherein the determination of the DNA sample is a natural DNA sample or an artificial DNA sample synthesized by WGA is achieved by sequencing said plurality of non-CODIS loci of said amplification products and determining methylation patterns of said first CG loci and the second CG loci of said plurality of non-CODIS loci in the DNA sample by analyzing said amplification products.

2. The method of claim 1 wherein said sequencing non-CODIS loci of said amplification products is performed by bisulfite sequencing.

3. The method of claim 1, wherein said determining the presence or absence of amplification products is by gel electrophoresis.

4. The method of claim 1, wherein the primers are fluorescently-labeled primers and said determining the presence or absence of amplification products is by capillary electrophoresis.

5. The method of claim 1, wherein the primers are fluorescently-labeled primers and said amplifying a set of loci of the bisulfite-treated DNA is performed by real time PCR.

* * * * *

UNITED STATES PATENT AND TRADEMARK OFFICE
CERTIFICATE OF CORRECTION

Page 1 of 1

PATENT NO.      : 9,458,503 B2
APPLICATION NO. : 13/381565
DATED           : October 4, 2016
INVENTOR(S)     : Wasserstrom et al.

It is certified that error appears in the above-identified patent and that said Letters Patent is hereby corrected as shown below:

In the claims

Column 91:
Line 37 (claim 1, line 27), delete "(2)" and insert -- wherein --.

Signed and Sealed this
Thirteenth Day of December, 2016

Michelle K. Lee
*Director of the United States Patent and Trademark Office*